US010240130B2

(12) United States Patent
Xie et al.

(10) Patent No.: US 10,240,130 B2
(45) Date of Patent: Mar. 26, 2019

(54) CDNA CLONE-LAUNCHED PLATFORM FOR HIGH-YIELD PRODUCTION OF INACTIVATED ZIKA VIRUS

(71) Applicant: THE BOARD OF REGENTS OF THE UNIVERSITY OF TEXAS SYSTEM, Austin, TX (US)

(72) Inventors: Xuping Xie, Galveston, TX (US); Chao Shan, Galveston, TX (US); Pei-Yong Shi, Galveston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/897,488

(22) Filed: Feb. 15, 2018

(65) Prior Publication Data

US 2018/0273913 A1  Sep. 27, 2018

Related U.S. Application Data

(60) Provisional application No. 62/459,367, filed on Feb. 15, 2017.

(51) Int. Cl.
| | |
|---|---|
| *A61K 39/00* | (2006.01) |
| *A61K 39/12* | (2006.01) |
| *C07K 14/005* | (2006.01) |
| *C12N 7/00* | (2006.01) |
| *A61K 31/70* | (2006.01) |
| *A61P 31/14* | (2006.01) |

(52) U.S. Cl.
CPC ............... *C12N 7/00* (2013.01); *A61K 39/12* (2013.01); *A61P 31/14* (2018.01); *A61K 2039/5252* (2013.01); *A61K 2039/5254* (2013.01); *A61K 2039/552* (2013.01); *A61K 2039/575* (2013.01); *C12N 2770/24121* (2013.01); *C12N 2770/24122* (2013.01); *C12N 2770/24134* (2013.01); *C12N 2770/24171* (2013.01)

(58) Field of Classification Search
CPC .... A61K 2300/00; A61K 39/12; A61K 39/00; C12N 7/00; C07K 14/005
See application file for complete search history.

(56) References Cited

U.S. PATENT DOCUMENTS

2010/0104598 A1   4/2010   Whitehead et al.

OTHER PUBLICATIONS

Abbink, Peter, et al. "Protective efficacy of multiple vaccine platforms against Zika virus challenge in rhesus monkeys." Science (2016): aah6157.

Atieh, Théreèse, et al. "Simple reverse genetics systems for Asian and African Zika viruses." Scientific reports 6 (2016): 39384.

Avirutnan, Panisadee, et al. "Binding of flavivirus nonstructural protein NS1 to C4b binding protein modulates complement activation." The Journal of Immunology (2011): 1100750.

Brown, W. Clay, et al. "Extended surface for membrane association in Zika virus NS1 structure." Nature structural & molecular biology 23.9 (2016): 865.

Chung, Kyung Min, et al. "West Nile virus nonstructural protein NS1 inhibits complement activation by binding the regulatory protein factor H." Proceedings of the National Academy of Sciences 103.50 (2006): 19111-19116.

Dawes, Brian E., et al. "Research and development of Zika virus vaccines." npj Vaccines 1 (2016): 16007.

Dick, G. W. A., S. F. Kitchen, and A. J. Haddow. "Zika virus (I). Isolations and serological specificity." Transactions of the royal society of tropical medicine and hygiene 46.5 (1952): 509-520.

Dowd, Kimberly A., et al. "Rapid development of a DNA vaccine for Zika virus." Science (2016): aai9137.

World Health Organization. "Acceptability of cell substrates for production of biologicals: report of a WHO study group [meeting held in Geneva from 18 to 19 Nov. 1986]." (1987).

Hamel, Rodolphe, et al. "Biology of Zika virus infection in human skin cells." Journal of virology (2015): JVI-00354.

Heang, Vireak, et al. "Zika virus infection, Cambodia, 2010." Emerging infectious diseases 18.2 (2012): 349.

Kostyuchenko, Victor A., et al. "Structure of the thermally stable Zika virus." Nature 533.7603 (2016): 425.

Kümmerer, Beate M., and Charles M. Rice. "Mutations in the yellow fever virus nonstructural protein NS2A selectively block production of infectious particles." Journal of virology 76.10 (2002): 4773-4784.

Lanciotti, Robert S., et al. "Phylogeny of Zika virus in western hemisphere, 2015." Emerging infectious diseases 22.5 (2016): 933.

Larocca, Rafael A., et al. "Vaccine protection against Zika virus from Brazil." Nature 536.7617 (2016): 474-478.

Lazear, Helen M., et al. "A mouse model of Zika virus pathogenesis." Cell host & microbe 19.5 (2016): 720-730.

Leung, Jason Y., et al. "Role of nonstructural protein NS2A in flavivirus assembly." Journal of virology 82.10 (2008): 4731-4741.

Leventis, Peter A., and Sergio Grinstein. "The distribution and function of phosphatidylserine in cellular membranes." Annual review of biophysics 39 (2010): 407-427.

Lindenbach, Brett D., and Charles M. Rice. "trans-Complementation of yellow fever virus NS1 reveals a role in early RNA replication." Journal of virology 71.12 (1997): 9608-9617.

Lindenbach, Brett D., and Charles M. Rice. "Genetic interaction of flavivirus nonstructural proteins NS1 and NS4A as a determinant of replicase function." Journal of virology73.6 (1999): 4611-4621.

(Continued)

*Primary Examiner* — Barry A Chestnut
(74) *Attorney, Agent, or Firm* — Robin L. Teskin; LeClairRyan PLLC

(57) ABSTRACT

The invention generally relates to the development of variant Zika strains, cDNA clones and mRNA transcripts that contain specific mutations in the Zika ORF, and methods for producing high yields of Zika viruses ("ZIKVs") using these variant cDNA clones, transcripts and strains. The produced ZIKVs can be used for the manufacture of purified inactivated vaccines (PIVs), which may be useful for treating ZIKV-related diseases and for providing immunoprotection against ZIKV.

20 Claims, 9 Drawing Sheets

Specification includes a Sequence Listing.

(56) References Cited

OTHER PUBLICATIONS

Perera-Lecoin, Manuel, et al. "Flavivirus entry receptors: an update." Viruses 6.1 (2013): 69-88.
Petersen, Lyle R., et al. "Zika virus." New England Journal of Medicine 374.16 (2016): 1552-1563.
Rossi, Shannan L., et al. "Characterization of a novel murine model to study Zika virus." The American journal of tropical medicine and hygiene 94.6 (2016): 1362-1369.
Scaturro, Pietro, et al. "Dengue virus non-structural protein 1 modulates infectious particle production via interaction with the structural proteins." PLoS pathogens 11.11 (2015): e1005277.
Schuler-Faccini, Lavinia. "Possible association between Zika virus infection and microcephaly—Brazil, 2015." MMWR. Morbidity and mortality weekly report 65 (2016).
Schwarz, Megan C., et al. "Rescue of the 1947 Zika virus prototype strain with a cytomegalovirus promoter-driven cDNA clone." mSphere 1.5 (2016): e00246-16.
Shan, Chao, et al. "Zika virus: diagnosis, therapeutics, and vaccine." ACS infectious diseases 2.3 (2016): 170-172.
Shan, Chao, et al. "An infectious cDNA clone of Zika virus to study viral virulence, mosquito transmission, and antiviral inhibitors." Cell host & microbe 19.6 (2016): 891-900.
Sirohi, Devika, et al. "The 3.8 Åresolution cryo-EM structure of Zika virus." Science 352.6284 (2016): 467-470.
Tsetsarkin, Konstantin A., et al. "A full-length infectious cDNA clone of Zika virus from the 2015 epidemic in Brazil as a genetic platform for studies of virus-host interactions and vaccine development." MBio 7.4 (2016): e01114-16.
Weger-Lucarelli, James, et al. "Development and characterization of recombinant virus generated from a New World Zika virus infectious clone." Journal of virology 91.1 (2017): e01765-16.
Xie, Xuping, et al. "Membrane topology and function of dengue virus NS2A protein." Journal of virology (2013): JVI-02424.
Xie, Xuping, et al. "Zika virus replicons for drug discovery." EBioMedicine 12 (2016): 156-160.
Youn, Soonjeon, et al. "Evidence for a genetic and physical interaction between the NS1 and NS4B that modulates replication of West Nile virus." Journal of virology (2012): JVI-00157.
Zou, Jing, et al. "Dimerization of flavivirus NS4B protein." Journal of virology (2014): JVI-02782.
Taglietti, M., C. N. Hawkins, and J. Rao. "Novel topical drug delivery systems and their potential use in acne vulgaris." Skin Therapy Lett 13.5 (2008): 6-8.
Wang, Lulan, et al. "From mosquitos to humans: genetic evolution of Zika virus." Cell host & microbe 19.5 (2016): 561-565.
Xie X, et al. "Understanding Zika Virus Stability and Developing a Chimeric Vaccine through Functional Analysis," MBio. Feb. 7, 2017;8(1). pii: e02134-16.
Manzano M, et al. "Identification of cis-acting elements in the 3'-untranslated region of the dengue virus type 2 RNA that modulate translation and replication," J Biol Chem. Jun. 24, 2011;286(25):22521-34.

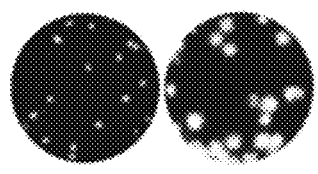
Figure 3D
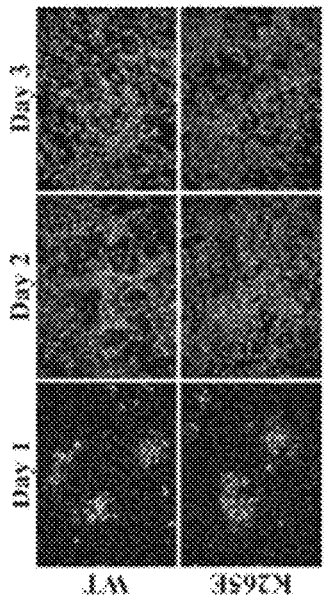
Figure 3C
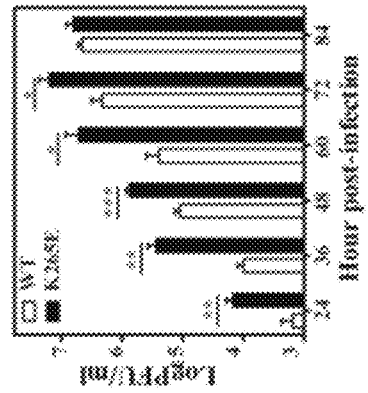
Figure 3E
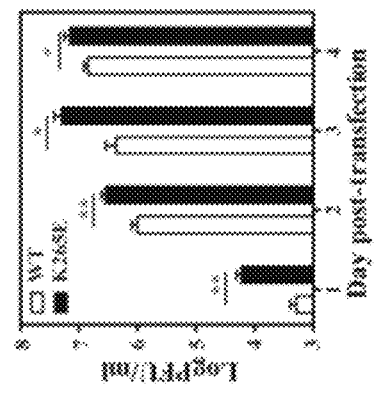
Figure 3F
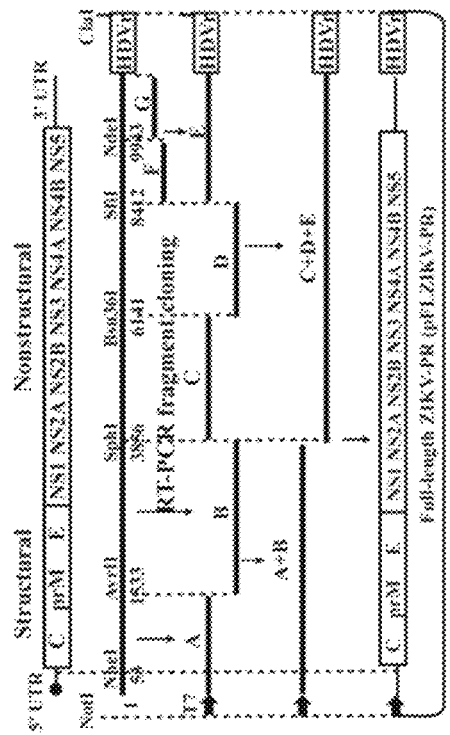
Figure 3A
Figure 3B

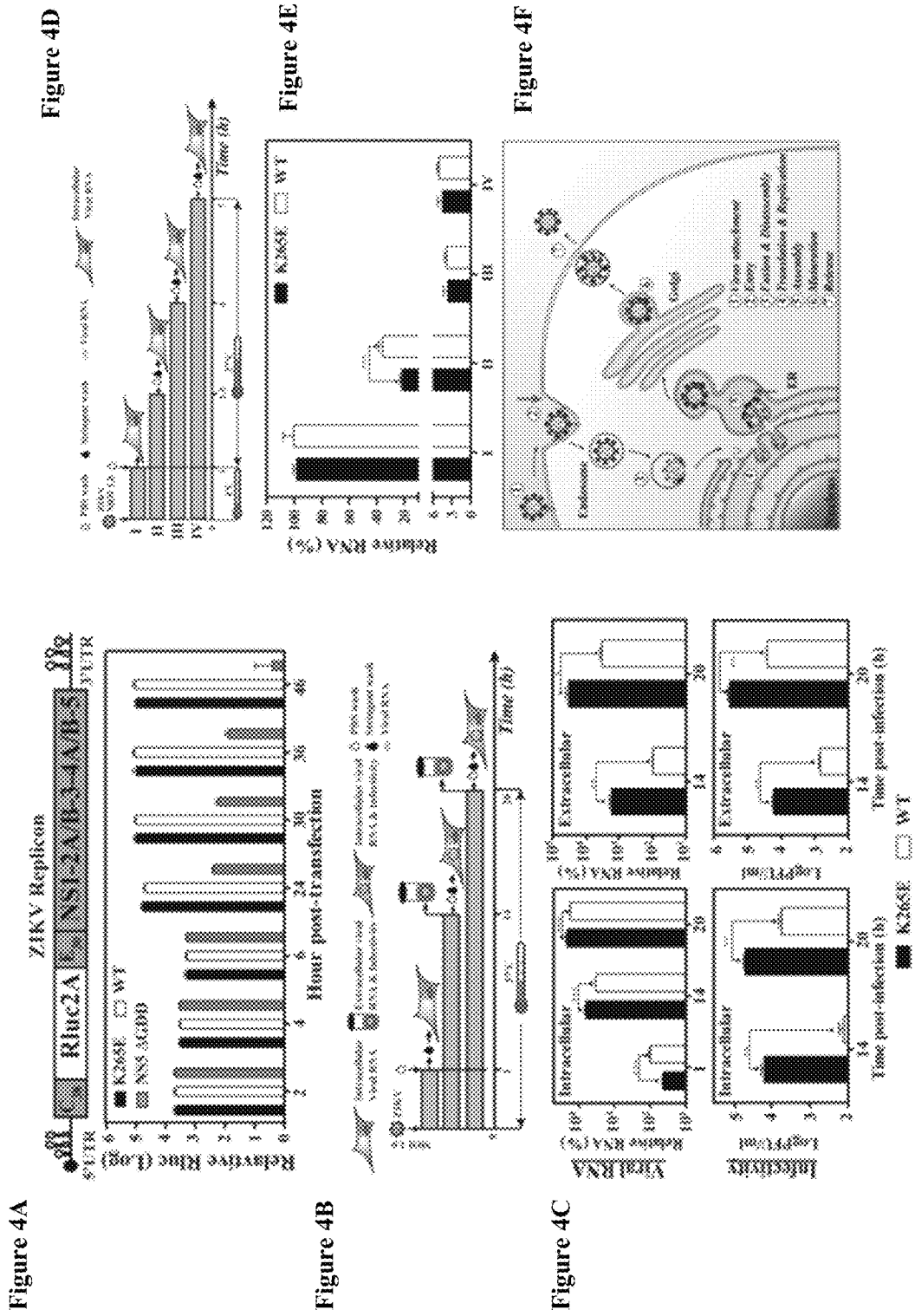

Figure 5A
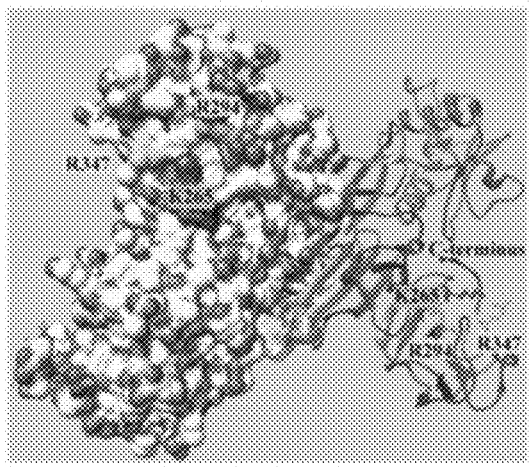
Figure 5B
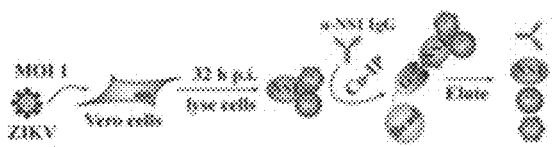
Figure 5C
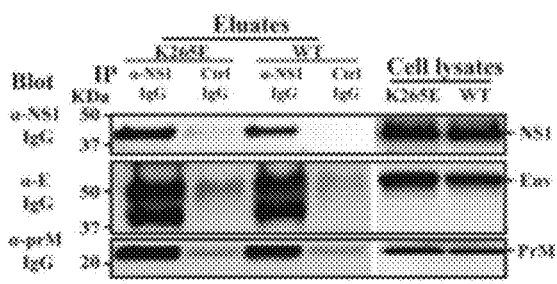
Figure 5D
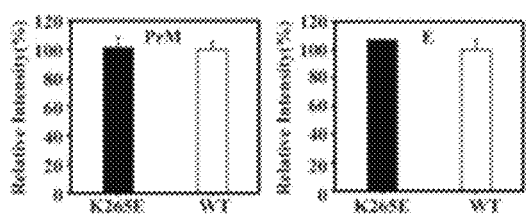
Figure 5E
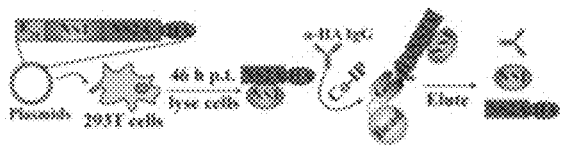
Figure 5F
Figure 5G
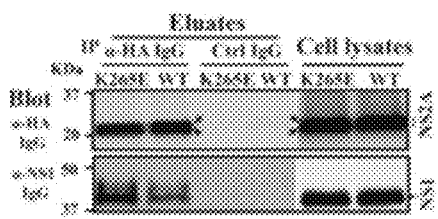

Figure 9A
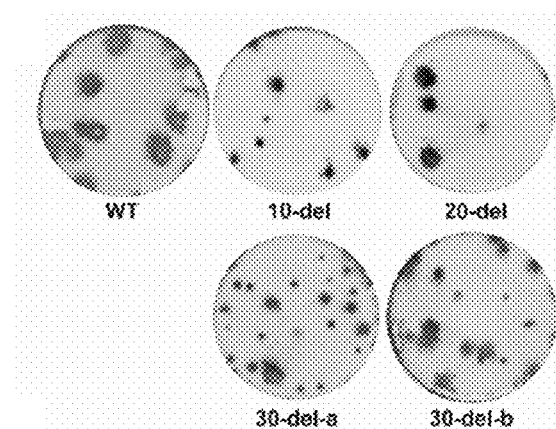
Figure 9B
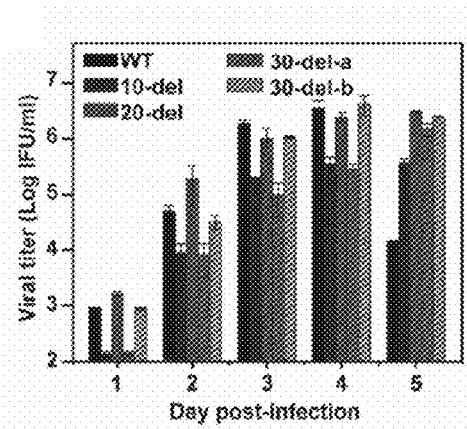
Figure 9C
|   | 10-del | | | 20-del | | | 30-del-a | | | 30-del-b | | |
|---|---|---|---|---|---|---|---|---|---|---|---|---|
|   | I | II | III | I | II | III | I | II | III | I | II | III |
| E | | R283W<br>H219L<br>R283W<br>L441L<br>K443N | H219L<br>R283W<br>L441L<br>K443N | T315I | K443N | K443N | H401Y | H401Y | — | A501T | A501T | A501T |
| NS1 | | R103K | | | W98L | | | | | | | |

SEQUENCE LISTING

```
<160> NUMBER OF SEQ ID NOS: 11

<210> SEQ ID NO 1
<211> LENGTH: 44
<212> TYPE: DNA
<213> ORGANISM: Artificial Sequence
<220> FEATURE:
<223> OTHER INFORMATION: forward primer - P1

<400> SEQUENCE: 1
gatgcggccg caccatgaat ggatctattt cccttatgtg cttg          44

<210> SEQ ID NO 2
<211> LENGTH: 52
<212> TYPE: DNA
<213> ORGANISM: Artificial Sequence
<220> FEATURE:
<223> OTHER INFORMATION: reverse primer - P2

<400> SEQUENCE: 2
taatctggaa catcgtatgg gtaggatccc cgcttcccac tccttgtgag ca     52

<210> SEQ ID NO 3
<211> LENGTH: 11
<212> TYPE: PRT
<213> ORGANISM: influenza virus
```

<400> SEQUENCE: 3

Gly Ser Tyr Pro Tyr Asp Val Pro Asp Tyr Ala
1               5                   10

<210> SEQ ID NO 4
<211> LENGTH: 45
<212> TYPE: DNA
<213> ORGANISM: Artificial Sequence
<220> FEATURE:
<223> OTHER INFORMATION: PCR using primer P1 and P3

<400> SEQUENCE: 4
gacctcgagc taagcgtaat ctggaacatc gtatgggtag gatcc            45

<210> SEQ ID NO 5
<211> LENGTH: 31
<212> TYPE: DNA
<213> ORGANISM: Artificial Sequence
<220> FEATURE:
<223> OTHER INFORMATION: probe with 5'-FAM reporter dye, 3' IBFQ & ZEN
      quenchers
<220> FEATURE:
<221> NAME/KEY: MOD_RES
<222> LOCATION: (1)..(1)
<223> OTHER INFORMATION: linked to FAM
<220> FEATURE:
<221> NAME/KEY: MOD_RES
<222> LOCATION: (10)..(10)
<223> OTHER INFORMATION: linked to Zen
<220> FEATURE:
<221> NAME/KEY: MOD_RES
<222> LOCATION: (31)..(31)
<223> OTHER INFORMATION: linked to 3IABkFQ

<400> SEQUENCE: 5
agcctacctt gacaagcaat cagacactca a                           31

<210> SEQ ID NO 6
<211> LENGTH: 17
<212> TYPE: DNA
<213> ORGANISM: Artificial Sequence
<220> FEATURE:
<223> OTHER INFORMATION: forward primer - ZIKV 1193F

<400> SEQUENCE: 6
ccgctgccca acacaag                                           17

<210> SEQ ID NO 7
<211> LENGTH: 24
<212> TYPE: DNA
<213> ORGANISM: Artificial Sequence
<220> FEATURE:
<223> OTHER INFORMATION: reverse primer - ZIKV 1269R

<400> SEQUENCE: 7
ccactaacgt tcttttgcag acat                                   24

<210> SEQ ID NO 8
<211> LENGTH: 21
<212> TYPE: DNA
<213> ORGANISM: Artificial Sequence
<220> FEATURE:
<223> OTHER INFORMATION: forward primer - M GAPDH-F

<400> SEQUENCE: 8
aggtcggtgt gaacggattt g                                      21

<210> SEQ ID NO 9
<211> LENGTH: 23
<212> TYPE: DNA
<213> ORGANISM: Artificial Sequence
<220> FEATURE:
<223> OTHER INFORMATION: reverse primer - M GAPDH-R

<400> SEQUENCE: 9
tgtagaccat gtagttgagg tca                                          23

<210> SEQ ID NO 10
<211> LENGTH: 10807
<212> TYPE: DNA
<213> ORGANISM: Zika virus
<220> FEATURE:
<221> NAME/KEY: CDS
<222> LOCATION: (108)..(10379)
<300> PUBLICATION INFORMATION:
<308> DATABASE ACCESSION NUMBER: KU955593.1
<309> DATABASE ENTRY DATE: 2016-05-24
<313> RELEVANT RESIDUES IN SEQ ID NO: (1)..(10807)

<400> SEQUENCE: 10

```
agttgttgat ctgtgtgaat cagactgcga cagttcgagt ttgaagcgaa agctagcaac      60
agtatcaaca ggttttattt tggatttgga aacgagagtt tctggtc atg aaa aac      116
                                                   Met Lys Asn
                                                     1 cca aag aag aaa tcc gga gga ttc cgg att gtc aat atg cta aaa cgc      164
Pro Lys Lys Lys Ser Gly Gly Phe Arg Ile Val Asn Met Leu Lys Arg
      5              10                  15 gga gta gcc cgt gtg agc ccc ttt ggg ggc ttg aag agg ctg cca gcc      212
Gly Val Ala Arg Val Ser Pro Phe Gly Gly Leu Lys Arg Leu Pro Ala
 20              25                  30                  35 gga ctt ctg ctg ggt cat ggg ccc atc agg atg gtc ttg gcg att cta      260
Gly Leu Leu Leu Gly His Gly Pro Ile Arg Met Val Leu Ala Ile Leu
                 40                  45                  50 gcc ttt ttg aga ttc acg gca atc aag cca tca ctg ggt ctc atc aat      308
Ala Phe Leu Arg Phe Thr Ala Ile Lys Pro Ser Leu Gly Leu Ile Asn
             55                  60                  65 aga tgg ggt tca gtg ggg aaa aaa gag gct atg gaa ata ata aag aag      356
Arg Trp Gly Ser Val Gly Lys Lys Glu Ala Met Glu Ile Ile Lys Lys
         70                  75                  80 ttt aag aaa gat ctg gct gcc atg ctg aga ata atc aat gct agg aag      404
Phe Lys Lys Asp Leu Ala Ala Met Leu Arg Ile Ile Asn Ala Arg Lys
     85                  90                  95 gag aag aag aga cga ggc aca gat act agt gtc gga att gtt ggc ctc      452
Glu Lys Lys Arg Arg Gly Thr Asp Thr Ser Val Gly Ile Val Gly Leu
100                 105                 110                 115 ctg ctg acc aca gcc atg gca gtg gag gtc act aga cgt ggg aat gca      500
Leu Leu Thr Thr Ala Met Ala Val Glu Val Thr Arg Arg Gly Asn Ala
                120                 125                 130 tac tat atg tac ttg gac aga agc gat gct ggg gag gcc ata tct ttt      548
Tyr Tyr Met Tyr Leu Asp Arg Ser Asp Ala Gly Glu Ala Ile Ser Phe
            135                 140                 145 cca acc aca atg ggg atg aat aag tgt tat ata cag atc atg gat ctt      596
Pro Thr Thr Met Gly Met Asn Lys Cys Tyr Ile Gln Ile Met Asp Leu
        150                 155                 160 gga cac atg tgt gat gcc acc atg agc tat gaa tgc cct atg ctg gat      644
Gly His Met Cys Asp Ala Thr Met Ser Tyr Glu Cys Pro Met Leu Asp
    165                 170                 175 gag ggg gta gaa cca gat gac gtc gat tgt tgg tgc aac acg acg tca      692
Glu Gly Val Glu Pro Asp Asp Val Asp Cys Trp Cys Asn Thr Thr Ser
180                 185                 190
```

-continued

| | |
|---|---|
| act tgg gtt gtg tac gga acc tgc cac cac aaa aaa ggt gaa gca cgg<br>Thr Trp Val Val Tyr Gly Thr Cys His His Lys Lys Gly Glu Ala Arg<br>                      200                      205                  210 | 740 |
| aga tct aga aga gct gtg acg ctc ccc tcc cat tcc act agg aag ctg<br>Arg Ser Arg Arg Ala Val Thr Leu Pro Ser His Ser Thr Arg Lys Leu<br>            215                      220                      225 | 788 |
| caa acg cgg tcg cag acc tgg ttg gaa tca aga gaa tac aca aag cac<br>Gln Thr Arg Ser Gln Thr Trp Leu Glu Ser Arg Glu Tyr Thr Lys His<br>                230                      235                      240 | 836 |
| ctg att aga gtc gaa aat tgg ata ttc agg aac cct ggc ttc gcg tta<br>Leu Ile Arg Val Glu Asn Trp Ile Phe Arg Asn Pro Gly Phe Ala Leu<br>245                      250                      255 | 884 |
| gca gca gct gcc atc gct tgg ctt ttg gga agc tca acg agc caa aaa<br>Ala Ala Ala Ala Ile Ala Trp Leu Leu Gly Ser Ser Thr Ser Gln Lys<br>260                      265                      270                      275 | 932 |
| gtc ata tac ttg gtc atg ata ctg ctg att gcc ccg gca tac agc atc<br>Val Ile Tyr Leu Val Met Ile Leu Leu Ile Ala Pro Ala Tyr Ser Ile<br>                280                      285                      290 | 980 |
| agg tgc ata gga gtc agc aat agg gac ttt gtg gaa ggt atg tca ggt<br>Arg Cys Ile Gly Val Ser Asn Arg Asp Phe Val Glu Gly Met Ser Gly<br>            295                      300                      305 | 1028 |
| ggg act tgg gtt gat gtt gtc ttg gaa cat gga ggt tgt gtt acc gta<br>Gly Thr Trp Val Asp Val Val Leu Glu His Gly Gly Cys Val Thr Val<br>                310                      315                      320 | 1076 |
| atg gca cag gac aaa ccg act gtc gac ata gag ctg gtt aca aca aca<br>Met Ala Gln Asp Lys Pro Thr Val Asp Ile Glu Leu Val Thr Thr Thr<br>325                      330                      335 | 1124 |
| gtc agc aac atg gcg gag gta aga tcc tac tgc tat gag gca tca ata<br>Val Ser Asn Met Ala Glu Val Arg Ser Tyr Cys Tyr Glu Ala Ser Ile<br>340                      345                      350                      355 | 1172 |
| tcg gac atg gct tcg gac agc cgc tgc cca aca caa ggt gaa gcc tac<br>Ser Asp Met Ala Ser Asp Ser Arg Cys Pro Thr Gln Gly Glu Ala Tyr<br>                360                      365                      370 | 1220 |
| ctt gac aag caa tca gac act caa tat gtc tgc aaa aga acg tta gtg<br>Leu Asp Lys Gln Ser Asp Thr Gln Tyr Val Cys Lys Arg Thr Leu Val<br>            375                      380                      385 | 1268 |
| gac aga ggc tgg gga aat gga tgt gga ctt ttt ggc aaa ggg agc ctg<br>Asp Arg Gly Trp Gly Asn Gly Cys Gly Leu Phe Gly Lys Gly Ser Leu<br>                390                      395                      400 | 1316 |
| gtg aca tgc gct aag ttt gct tgc tct aag aaa atg acc ggg aag agc<br>Val Thr Cys Ala Lys Phe Ala Cys Ser Lys Lys Met Thr Gly Lys Ser<br>405                      410                      415 | 1364 |
| atc cag cca gag aat ctg gag tac cgg ata atg ctg tca gtt cat ggc<br>Ile Gln Pro Glu Asn Leu Glu Tyr Arg Ile Met Leu Ser Val His Gly<br>420                      425                      430                      435 | 1412 |
| tcc cag cac agt ggg atg atc gtt aat gat aca gga cat gaa act gat<br>Ser Gln His Ser Gly Met Ile Val Asn Asp Thr Gly His Glu Thr Asp<br>                440                      445                      450 | 1460 |
| gag aat aga gcg aag gtt gag ata acg ccc aat tca cca aga gcc gaa<br>Glu Asn Arg Ala Lys Val Glu Ile Thr Pro Asn Ser Pro Arg Ala Glu<br>            455                      460                      465 | 1508 |
| gcc acc ctg ggg ggt ttt gga agc cta gga ctt gat tgt gaa ccg agg<br>Ala Thr Leu Gly Gly Phe Gly Ser Leu Gly Leu Asp Cys Glu Pro Arg<br>                470                      475                      480 | 1556 |
| aca ggc ctt gac ttt tca gat ttg tat tac ttg act atg aat aac aag<br>Thr Gly Leu Asp Phe Ser Asp Leu Tyr Tyr Leu Thr Met Asn Asn Lys<br>485                      490                      495 | 1604 |
| cac tgg ttg gtt cac aag gag tgg ttc cac gac att cca tta cct tgg | 1652 |

```
                His Trp Leu Val His Lys Glu Trp Phe His Asp Ile Pro Leu Pro Trp
                500                 505                 510                 515 cat gct ggg gca gac acc gga act cca cac tgg aac aac aaa gaa gca              1700
His Ala Gly Ala Asp Thr Gly Thr Pro His Trp Asn Asn Lys Glu Ala
                    520                 525                 530 ctg gta gag ttc aag gac gca cat gcc aaa agg cag act gtc gtg gtt              1748
Leu Val Glu Phe Lys Asp Ala His Ala Lys Arg Gln Thr Val Val Val
                535                 540                 545 cta ggg agt caa gaa gga gca gtt cac acg gcc ctt gct gga gct ctg              1796
Leu Gly Ser Gln Glu Gly Ala Val His Thr Ala Leu Ala Gly Ala Leu
            550                 555                 560 gag gct gag atg gat ggt gca aag gga agg ctg tcc tct ggc cac ttg              1844
Glu Ala Glu Met Asp Gly Ala Lys Gly Arg Leu Ser Ser Gly His Leu
        565                 570                 575 aaa tgt cgc ctg aaa atg gat aaa ctt aga ttg aag ggc gtg tca tac              1892
Lys Cys Arg Leu Lys Met Asp Lys Leu Arg Leu Lys Gly Val Ser Tyr
580                 585                 590                 595 tcc ttg tgt acc gca gcg ttc aca ttc act aag atc ccg gct gaa aca              1940
Ser Leu Cys Thr Ala Ala Phe Thr Phe Thr Lys Ile Pro Ala Glu Thr
                600                 605                 610 ctg cac ggg aca gtc aca gtg gag gta cag tac gca ggg aca gat gga              1988
Leu His Gly Thr Val Thr Val Glu Val Gln Tyr Ala Gly Thr Asp Gly
            615                 620                 625 cct tgc aag gtt cca gct cag atg gcg gtg gac atg caa act ctg acc              2036
Pro Cys Lys Val Pro Ala Gln Met Ala Val Asp Met Gln Thr Leu Thr
        630                 635                 640 cca gtt ggg agg ttg ata acc gct aac cct gta atc act gaa agc act              2084
Pro Val Gly Arg Leu Ile Thr Ala Asn Pro Val Ile Thr Glu Ser Thr
645                 650                 655 gag aac tcc aag atg atg ctg gaa ctg gat cca cca ttt ggg gac tct              2132
Glu Asn Ser Lys Met Met Leu Glu Leu Asp Pro Pro Phe Gly Asp Ser
660                 665                 670                 675 tac att gtc ata gga gtc ggg gaa aag aag atc acc cac cac tgg cac              2180
Tyr Ile Val Ile Gly Val Gly Glu Lys Lys Ile Thr His His Trp His
                680                 685                 690 agg agt ggc agc acc att gga aaa gca ttt gaa gcc act gtg aga ggt              2228
Arg Ser Gly Ser Thr Ile Gly Lys Ala Phe Glu Ala Thr Val Arg Gly
            695                 700                 705 gcc aag aga atg gca gtc ttg gga gac aca gcc tgg gac ttt gga tca              2276
Ala Lys Arg Met Ala Val Leu Gly Asp Thr Ala Trp Asp Phe Gly Ser
        710                 715                 720 gtt ggg ggt gct ctc aac tca ctg ggc aag ggc atc cat caa att ttt              2324
Val Gly Gly Ala Leu Asn Ser Leu Gly Lys Gly Ile His Gln Ile Phe
725                 730                 735 gga gca gct ttc aaa tca ttg ttt gga gga atg tcc tgg ttc tca caa              2372
Gly Ala Ala Phe Lys Ser Leu Phe Gly Gly Met Ser Trp Phe Ser Gln
740                 745                 750                 755 att ctc att gga acg ttg ctg gtg tgg ttg ggt ctg aat aca aag aat              2420
Ile Leu Ile Gly Thr Leu Leu Val Trp Leu Gly Leu Asn Thr Lys Asn
                760                 765                 770 gga tct att tcc ctt atg tgc ttg gcc tta ggg gga gtg ttg atc ttc              2468
Gly Ser Ile Ser Leu Met Cys Leu Ala Leu Gly Gly Val Leu Ile Phe
            775                 780                 785 tta tcc aca gcc gtc tct gct gat gtg ggg tgc tcg gtg gac ttc tca              2516
Leu Ser Thr Ala Val Ser Ala Asp Val Gly Cys Ser Val Asp Phe Ser
        790                 795                 800 aag aag gaa acg aga tgc ggt aca ggg gtg ttc gtc tat aac gac gtt              2564
Lys Lys Glu Thr Arg Cys Gly Thr Gly Val Phe Val Tyr Asn Asp Val
805                 810                 815
```

```
gaa gct tgg agg gac agg tac aag tac cat cct gac tcc cct cgt aga    2612
Glu Ala Trp Arg Asp Arg Tyr Lys Tyr His Pro Asp Ser Pro Arg Arg
820                 825                 830                 835 ttg gca gca gca gtc aag caa gcc tgg gaa gat ggg atc tgt ggg atc    2660
Leu Ala Ala Ala Val Lys Gln Ala Trp Glu Asp Gly Ile Cys Gly Ile
                840                 845                 850 tcc tct gtt tca aga atg gaa aac atc atg tgg aga tca gta gaa ggg    2708
Ser Ser Val Ser Arg Met Glu Asn Ile Met Trp Arg Ser Val Glu Gly
            855                 860                 865 gag ctc aac gca atc ctg gaa gag aat gga gtt caa ctg acg gtc gtt    2756
Glu Leu Asn Ala Ile Leu Glu Glu Asn Gly Val Gln Leu Thr Val Val
        870                 875                 880 gtg gga tct gta aaa aac ccc atg tgg aga ggt cca cag aga ttg ccc    2804
Val Gly Ser Val Lys Asn Pro Met Trp Arg Gly Pro Gln Arg Leu Pro
    885                 890                 895 gtg cct gtg aac gag ctg ccc cat ggc tgg aag gct tgg ggg aaa tcg    2852
Val Pro Val Asn Glu Leu Pro His Gly Trp Lys Ala Trp Gly Lys Ser
900                 905                 910                 915 tac ttc gtc agg gca gca aag aca aat aac agc ttt gtc gtg gat ggt    2900
Tyr Phe Val Arg Ala Ala Lys Thr Asn Asn Ser Phe Val Val Asp Gly
                920                 925                 930 gac aca ctg aag gaa tgc cca ctc aaa cat aga gca tgg aac agc ttt    2948
Asp Thr Leu Lys Glu Cys Pro Leu Lys His Arg Ala Trp Asn Ser Phe
            935                 940                 945 ctt gtg gag gat cat ggg ttc ggg gta ttt cac act agt gtc tgg ctc    2996
Leu Val Glu Asp His Gly Phe Gly Val Phe His Thr Ser Val Trp Leu
        950                 955                 960 aag gtt aga gaa gat tat tca tta gag tgt gat cca gcc gtc att gga    3044
Lys Val Arg Glu Asp Tyr Ser Leu Glu Cys Asp Pro Ala Val Ile Gly
    965                 970                 975 aca gcc gct aag gga aag gag gct gtg cac agt gat cta ggc tac tgg    3092
Thr Ala Ala Lys Gly Lys Glu Ala Val His Ser Asp Leu Gly Tyr Trp
980                 985                 990                 995 att gag agt gag aag  aac gac aca tgg agg  ctg aag agg gcc cac      3137
Ile Glu Ser Glu Lys Asn Asp Thr Trp Arg Leu Lys Arg Ala His
                1000                1005                1010 ctg atc gag atg aaa  aca tgt gaa tgg cca  aag tcc cac aca ttg      3182
Leu Ile Glu Met Lys Thr Cys Glu Trp Pro Lys Ser His Thr Leu
                1015                1020                1025 tgg aca gat gga ata  gaa gaa agt gat ctg  atc ata ccc aag tct      3227
Trp Thr Asp Gly Ile Glu Glu Ser Asp Leu Ile Ile Pro Lys Ser
                1030                1035                1040 tta gct ggg cca ctc  agc cat cac aac acc  aga gag ggc tac agg      3272
Leu Ala Gly Pro Leu Ser His His Asn Thr Arg Glu Gly Tyr Arg
                1045                1050                1055 acc caa atg aaa ggg  cca tgg cat agt gaa  gag ctt gaa att cgg      3317
Thr Gln Met Lys Gly Pro Trp His Ser Glu Glu Leu Glu Ile Arg
                1060                1065                1070 ttt gag gaa tgc cca  ggc act aag gtc cac  gtg gag gaa aca tgt      3362
Phe Glu Glu Cys Pro Gly Thr Lys Val His Val Glu Glu Thr Cys
                1075                1080                1085 gga aca aga gga cca  tct ctg aga tca acc  act gca agc gga agg      3407
Gly Thr Arg Gly Pro Ser Leu Arg Ser Thr Thr Ala Ser Gly Arg
                1090                1095                1100 gtg atc gag gaa tgg  tgc tgc agg gag tgc  aca atg ccc cca ctg      3452
Val Ile Glu Glu Trp Cys Cys Arg Glu Cys Thr Met Pro Pro Leu
                1105                1110                1115 tcg ttc cgg gct aaa  gat ggt tgt tgg tat  gga atg gag ata agg      3497
Ser Phe Arg Ala Lys Asp Gly Cys Trp Tyr Gly Met Glu Ile Arg
                1120                1125                1130
```

-continued

| | |
|---|---|
| ccc agg aaa gaa cca gaa agt aac tta gta agg tca atg gtg act<br>Pro Arg Lys Glu Pro Glu Ser Asn Leu Val Arg Ser Met Val Thr<br>1135                         1140                      1145 | 3542 |
| gca gga tca act gat cac atg gat cac ttc tcc ctt gga gtg ctt<br>Ala Gly Ser Thr Asp His Met Asp His Phe Ser Leu Gly Val Leu<br>1150                         1155                      1160 | 3587 |
| gtg att ctg ctc atg gta cag gaa ggg cta aag aag aga atg acc<br>Val Ile Leu Leu Met Val Gln Glu Gly Leu Lys Lys Arg Met Thr<br>1165                         1170                      1175 | 3632 |
| aca aag atc atc ata agc aca tca atg gca gtg ctg gta gct atg<br>Thr Lys Ile Ile Ile Ser Thr Ser Met Ala Val Leu Val Ala Met<br>1180                         1185                      1190 | 3677 |
| atc ctg gga gga ttt tca atg agt gac ctg gct aag ctt gca att<br>Ile Leu Gly Gly Phe Ser Met Ser Asp Leu Ala Lys Leu Ala Ile<br>1195                         1200                      1205 | 3722 |
| ttg atg ggt gcc acc ttc gcg gaa atg aac act gga gga gat gtt<br>Leu Met Gly Ala Thr Phe Ala Glu Met Asn Thr Gly Gly Asp Val<br>1210                         1215                      1220 | 3767 |
| gct cat ctg gcg ctg ata gcg gca ttc aaa gtc aga cct gcg ttg<br>Ala His Leu Ala Leu Ile Ala Ala Phe Lys Val Arg Pro Ala Leu<br>1225                         1230                      1235 | 3812 |
| ctg gta tct ttc att ttc aga gct aat tgg aca ccc cgt gag agc<br>Leu Val Ser Phe Ile Phe Arg Ala Asn Trp Thr Pro Arg Glu Ser<br>1240                         1245                      1250 | 3857 |
| atg ctg ctg gcc ttg gcc tcg tgt ctt ctg caa act gcg atc tcc<br>Met Leu Leu Ala Leu Ala Ser Cys Leu Leu Gln Thr Ala Ile Ser<br>1255                         1260                      1265 | 3902 |
| gcc ttg gaa ggc gac ctg atg gtt ccc atc aat ggt ttt gct ttg<br>Ala Leu Glu Gly Asp Leu Met Val Pro Ile Asn Gly Phe Ala Leu<br>1270                         1275                      1280 | 3947 |
| gcc tgg ttg gca ata cga gcg atg gtt gtt cca cgc act gac aac<br>Ala Trp Leu Ala Ile Arg Ala Met Val Val Pro Arg Thr Asp Asn<br>1285                         1290                      1295 | 3992 |
| atc acc ttg gca atc ctg gct gct ctg aca cca ctg gcc cgg ggc<br>Ile Thr Leu Ala Ile Leu Ala Ala Leu Thr Pro Leu Ala Arg Gly<br>1300                         1305                      1310 | 4037 |
| aca ctg ctt gtg gcg tgg aga gca ggc ctt gct act tgc ggg ggg<br>Thr Leu Leu Val Ala Trp Arg Ala Gly Leu Ala Thr Cys Gly Gly<br>1315                         1320                      1325 | 4082 |
| ttc atg ctc ctt tct ctg aag ggg aaa ggc agt gtg aag aag aac<br>Phe Met Leu Leu Ser Leu Lys Gly Lys Gly Ser Val Lys Lys Asn<br>1330                         1335                      1340 | 4127 |
| tta cca ttt gtc atg gcc ctg gga cta acc gct gtg agg ctg gtc<br>Leu Pro Phe Val Met Ala Leu Gly Leu Thr Ala Val Arg Leu Val<br>1345                         1350                      1355 | 4172 |
| gac ccc atc aac gtg gtg gga ctg ctg ttg ctc aca agg agt ggg<br>Asp Pro Ile Asn Val Val Gly Leu Leu Leu Leu Thr Arg Ser Gly<br>1360                         1365                      1370 | 4217 |
| aag cgg agc tgg ccc cct agt gaa gta ctc aca gct gtt ggc ctg<br>Lys Arg Ser Trp Pro Pro Ser Glu Val Leu Thr Ala Val Gly Leu<br>1375                         1380                      1385 | 4262 |
| ata tgc gca ttg gct gga ggg ttc gcc aag gcg gat ata gag atg<br>Ile Cys Ala Leu Ala Gly Gly Phe Ala Lys Ala Asp Ile Glu Met<br>1390                         1395                      1400 | 4307 |
| gct ggg ccc atg gcc gcg gtc ggt ctg cta att gtc agt tac gtg<br>Ala Gly Pro Met Ala Ala Val Gly Leu Leu Ile Val Ser Tyr Val<br>1405                         1410                      1415 | 4352 |
| gtc tca gga aag agt gtg gac atg tac att gaa aga gca ggt gac<br>Val Ser Gly Lys Ser Val Asp Met Tyr Ile Glu Arg Ala Gly Asp | 4397 |

-continued

|  |  |  |  |
|---|---|---|---|
| 1420 | 1425 | 1430 | |

| atc aca tgg gaa aaa gat gcg gaa gtc act gga aac agt ccc cgg | 4442 |
| Ile Thr Trp Glu Lys Asp Ala Glu Val Thr Gly Asn Ser Pro Arg | |
| 1435 1440 1445 | |

| ctc gat gtg gca cta gat gag agt ggt gat ttc tcc cta gtg gag | 4487 |
| Leu Asp Val Ala Leu Asp Glu Ser Gly Asp Phe Ser Leu Val Glu | |
| 1450 1455 1460 | |

| gat gat ggt ccc ccc atg aga gag atc ata ctc aaa gtg gtc ctg | 4532 |
| Asp Asp Gly Pro Pro Met Arg Glu Ile Ile Leu Lys Val Val Leu | |
| 1465 1470 1475 | |

| atg gcc atc tgt ggc atg aac cca ata gcc ata ccc ttt gca gct | 4577 |
| Met Ala Ile Cys Gly Met Asn Pro Ile Ala Ile Pro Phe Ala Ala | |
| 1480 1485 1490 | |

| gga gcg tgg tac gtg tat gtg aag act gga aaa agg agt ggt gct | 4622 |
| Gly Ala Trp Tyr Val Tyr Val Lys Thr Gly Lys Arg Ser Gly Ala | |
| 1495 1500 1505 | |

| cta tgg gat gtg cct gct ccc aag gaa gta aaa aag ggg gag acc | 4667 |
| Leu Trp Asp Val Pro Ala Pro Lys Glu Val Lys Lys Gly Glu Thr | |
| 1510 1515 1520 | |

| aca gat gga gtg tac aga gta atg act cgt aga ctg cta ggt tca | 4712 |
| Thr Asp Gly Val Tyr Arg Val Met Thr Arg Arg Leu Leu Gly Ser | |
| 1525 1530 1535 | |

| aca caa gtt gga gtg gga gtc atg caa gag ggg gtc ttc cac act | 4757 |
| Thr Gln Val Gly Val Gly Val Met Gln Glu Gly Val Phe His Thr | |
| 1540 1545 1550 | |

| atg tgg cac gtc aca aaa gga tcc gcg ctg aga agc ggt gaa ggg | 4802 |
| Met Trp His Val Thr Lys Gly Ser Ala Leu Arg Ser Gly Glu Gly | |
| 1555 1560 1565 | |

| aga ctt gat cca tac tgg gga gat gtc aag cag gat ctg gtg tca | 4847 |
| Arg Leu Asp Pro Tyr Trp Gly Asp Val Lys Gln Asp Leu Val Ser | |
| 1570 1575 1580 | |

| tac tgt ggt cca tgg aag cta gat gcc gcc tgg gac ggg cac agc | 4892 |
| Tyr Cys Gly Pro Trp Lys Leu Asp Ala Ala Trp Asp Gly His Ser | |
| 1585 1590 1595 | |

| gag gtg cag ctc ttg gcc gtg ccc ccc gga gag aga gcg agg aac | 4937 |
| Glu Val Gln Leu Leu Ala Val Pro Pro Gly Glu Arg Ala Arg Asn | |
| 1600 1605 1610 | |

| atc cag act ctg ccc gga ata ttt aag aca aag gat ggg gac att | 4982 |
| Ile Gln Thr Leu Pro Gly Ile Phe Lys Thr Lys Asp Gly Asp Ile | |
| 1615 1620 1625 | |

| gga gca gtt gcg ctg gac tac cca gca gga act tca gga tct cca | 5027 |
| Gly Ala Val Ala Leu Asp Tyr Pro Ala Gly Thr Ser Gly Ser Pro | |
| 1630 1635 1640 | |

| atc cta gat aag tgt ggg aga gtg ata gga ctc tat ggt aat ggg | 5072 |
| Ile Leu Asp Lys Cys Gly Arg Val Ile Gly Leu Tyr Gly Asn Gly | |
| 1645 1650 1655 | |

| gtc gtg atc aaa aat ggg agt tac gtt agt gcc atc acc caa ggg | 5117 |
| Val Val Ile Lys Asn Gly Ser Tyr Val Ser Ala Ile Thr Gln Gly | |
| 1660 1665 1670 | |

| agg agg gag gaa gag act cct gtt gag tgc ttc gag cct tcg atg | 5162 |
| Arg Arg Glu Glu Glu Thr Pro Val Glu Cys Phe Glu Pro Ser Met | |
| 1675 1680 1685 | |

| ctg aag aag aag cag cta act gtc tta gac ttg cat cct gga gct | 5207 |
| Leu Lys Lys Lys Gln Leu Thr Val Leu Asp Leu His Pro Gly Ala | |
| 1690 1695 1700 | |

| ggg aaa acc agg aga gtt ctt cct gaa ata gtc cgt gaa gcc ata | 5252 |
| Gly Lys Thr Arg Arg Val Leu Pro Glu Ile Val Arg Glu Ala Ile | |
| 1705 1710 1715 | |

| aaa aca aga ctc cgc act gtg atc tta gct cca acc agg gtt gtc | 5297 |

```
                Lys Thr Arg Leu Arg   Thr Val Ile Leu Ala   Pro Thr Arg Val
                            1720                    1725                1730 gct gct gaa atg gag   gaa gcc ctt aga ggg   ctt cca gtg cgt tat              5342
Ala Ala Glu Met Glu   Glu Ala Leu Arg Gly   Leu Pro Val Arg Tyr
            1735                    1740                    1745 atg aca aca gca gtc   aat gtc acc cat tct   ggg aca gaa atc gtt              5387
Met Thr Thr Ala Val   Asn Val Thr His Ser   Gly Thr Glu Ile Val
            1750                    1755                    1760 gac tta atg tgc cat   gcc acc ttc act tca   cgt cta cta cag cca              5432
Asp Leu Met Cys His   Ala Thr Phe Thr Ser   Arg Leu Leu Gln Pro
            1765                    1770                    1775 atc aga gtc ccc aac   tat aat ctg tat att   atg gat gag gcc cac              5477
Ile Arg Val Pro Asn   Tyr Asn Leu Tyr Ile   Met Asp Glu Ala His
            1780                    1785                    1790 ttc aca gat ccc tca   agt ata gca gca aga   gga tac att tca aca              5522
Phe Thr Asp Pro Ser   Ser Ile Ala Ala Arg   Gly Tyr Ile Ser Thr
            1795                    1800                    1805 agg gtt gag atg ggc   gag gcg gct gcc atc   ttc atg act gcc acg              5567
Arg Val Glu Met Gly   Glu Ala Ala Ala Ile   Phe Met Thr Ala Thr
            1810                    1815                    1820 cca cca gga acc cgt   gac gca ttc ccg gac   tcc aac tca cca att              5612
Pro Pro Gly Thr Arg   Asp Ala Phe Pro Asp   Ser Asn Ser Pro Ile
            1825                    1830                    1835 atg gac acc gaa gtg   gaa gtc cca gag aga   gcc tgg agc tca ggc              5657
Met Asp Thr Glu Val   Glu Val Pro Glu Arg   Ala Trp Ser Ser Gly
            1840                    1845                    1850 ttt gat tgg gtg acg   gat cat tct gga aaa   aca gtt tgg ttt gtt              5702
Phe Asp Trp Val Thr   Asp His Ser Gly Lys   Thr Val Trp Phe Val
            1855                    1860                    1865 cca agc gtg agg aat   ggc aat gag atc gca   gct tgt ctg aca aag              5747
Pro Ser Val Arg Asn   Gly Asn Glu Ile Ala   Ala Cys Leu Thr Lys
            1870                    1875                    1880 gct gga aaa cgg gtc   ata cag ctc agc aga   aag act ttt gag aca              5792
Ala Gly Lys Arg Val   Ile Gln Leu Ser Arg   Lys Thr Phe Glu Thr
            1885                    1890                    1895 gag ttc cag aaa aca   aaa cat caa gag tgg   gac ttc gtc gtg aca              5837
Glu Phe Gln Lys Thr   Lys His Gln Glu Trp   Asp Phe Val Val Thr
            1900                    1905                    1910 act gac att tca gag   atg ggc gcc aac ttt   aaa gct gac cgt gtc              5882
Thr Asp Ile Ser Glu   Met Gly Ala Asn Phe   Lys Ala Asp Arg Val
            1915                    1920                    1925 ata gat tcc agg aga   tgc cta aag ccg gtc   ata ctt gat ggc gag              5927
Ile Asp Ser Arg Arg   Cys Leu Lys Pro Val   Ile Leu Asp Gly Glu
            1930                    1935                    1940 aga gtc att ctg gct   gga ccc atg cct gtc   aca cat gcc agc gct              5972
Arg Val Ile Leu Ala   Gly Pro Met Pro Val   Thr His Ala Ser Ala
            1945                    1950                    1955 gcc cag agg agg ggg   cgc ata ggc agg aac   ccc aac aaa cct gga              6017
Ala Gln Arg Arg Gly   Arg Ile Gly Arg Asn   Pro Asn Lys Pro Gly
            1960                    1965                    1970 gat gag tat ctg tat   gga ggt ggg tgc gca   gag act gat gaa gac              6062
Asp Glu Tyr Leu Tyr   Gly Gly Gly Cys Ala   Glu Thr Asp Glu Asp
            1975                    1980                    1985 cat gca cac tgg ctt   gaa gca aga atg ctt   ctt gac aac att tac              6107
His Ala His Trp Leu   Glu Ala Arg Met Leu   Leu Asp Asn Ile Tyr
            1990                    1995                    2000 ctc caa gat ggc ctc   ata gcc tcg ctc tat   cga cct gag gcc gac              6152
Leu Gln Asp Gly Leu   Ile Ala Ser Leu Tyr   Arg Pro Glu Ala Asp
            2005                    2010                    2015
```

-continued

| | | | | | | | | | | | | | | |
|---|---|---|---|---|---|---|---|---|---|---|---|---|---|---|
| aaa | gta | gca | gct | att | gag | gga | gag | ttc | aag | ctt | agg | acg | gag | caa | 6197 |
| Lys | Val | Ala | Ala | Ile | Glu | Gly | Glu | Phe | Lys | Leu | Arg | Thr | Glu | Gln | |
| | | | 2020 | | | | 2025 | | | | 2030 | | | | |

| agg | aag | acc | ttt | gtg | gaa | ctc | atg | aaa | aga | gga | gat | ctt | cct | gtt | 6242 |
| Arg | Lys | Thr | Phe | Val | Glu | Leu | Met | Lys | Arg | Gly | Asp | Leu | Pro | Val | |
| | | | 2035 | | | | 2040 | | | | 2045 | | | | |

| tgg | ctg | gcc | tat | cag | gtt | gca | tct | gcc | gga | ata | acc | tac | aca | gat | 6287 |
| Trp | Leu | Ala | Tyr | Gln | Val | Ala | Ser | Ala | Gly | Ile | Thr | Tyr | Thr | Asp | |
| | | 2050 | | | | 2055 | | | | 2060 | | | | | |

| aga | aga | tgg | tgc | ttt | gat | ggc | acg | acc | aac | aac | acc | ata | atg | gaa | 6332 |
| Arg | Arg | Trp | Cys | Phe | Asp | Gly | Thr | Thr | Asn | Asn | Thr | Ile | Met | Glu | |
| | | 2065 | | | | 2070 | | | | 2075 | | | | | |

| gac | agt | gtg | ccg | gca | gag | gtg | tgg | acc | aga | tac | gga | gag | aaa | aga | 6377 |
| Asp | Ser | Val | Pro | Ala | Glu | Val | Trp | Thr | Arg | Tyr | Gly | Glu | Lys | Arg | |
| | | 2080 | | | | 2085 | | | | 2090 | | | | | |

| gtg | ctc | aaa | ccg | agg | tgg | atg | gac | gcc | aga | gtt | tgt | tca | gat | cat | 6422 |
| Val | Leu | Lys | Pro | Arg | Trp | Met | Asp | Ala | Arg | Val | Cys | Ser | Asp | His | |
| | | 2095 | | | | 2100 | | | | 2105 | | | | | |

| gcg | gcc | ctg | aag | tca | ttc | aaa | gag | ttt | gcc | gct | ggg | aaa | aga | gga | 6467 |
| Ala | Ala | Leu | Lys | Ser | Phe | Lys | Glu | Phe | Ala | Ala | Gly | Lys | Arg | Gly | |
| | | 2110 | | | | 2115 | | | | 2120 | | | | | |

| gcg | gcc | ttt | gga | gtg | atg | gaa | gcc | ctg | gga | aca | ctg | cca | gga | cat | 6512 |
| Ala | Ala | Phe | Gly | Val | Met | Glu | Ala | Leu | Gly | Thr | Leu | Pro | Gly | His | |
| | | 2125 | | | | 2130 | | | | 2135 | | | | | |

| atg | aca | gag | aga | ttc | cag | gag | gcc | att | gac | aac | ctc | gct | gtg | ctc | 6557 |
| Met | Thr | Glu | Arg | Phe | Gln | Glu | Ala | Ile | Asp | Asn | Leu | Ala | Val | Leu | |
| | | 2140 | | | | 2145 | | | | 2150 | | | | | |

| atg | cgg | gca | gag | act | gga | agc | agg | ccc | tac | aaa | gcc | gcg | gcg | gcc | 6602 |
| Met | Arg | Ala | Glu | Thr | Gly | Ser | Arg | Pro | Tyr | Lys | Ala | Ala | Ala | Ala | |
| | | 2155 | | | | 2160 | | | | 2165 | | | | | |

| caa | tta | ccg | gag | acc | cta | gag | act | atc | atg | ctt | ttg | ggg | ttg | ctg | 6647 |
| Gln | Leu | Pro | Glu | Thr | Leu | Glu | Thr | Ile | Met | Leu | Leu | Gly | Leu | Leu | |
| | | 2170 | | | | 2175 | | | | 2180 | | | | | |

| gga | aca | gtc | tcg | ctg | gga | atc | ttt | ttc | gtc | ttg | atg | cgg | aac | aag | 6692 |
| Gly | Thr | Val | Ser | Leu | Gly | Ile | Phe | Phe | Val | Leu | Met | Arg | Asn | Lys | |
| | | 2185 | | | | 2190 | | | | 2195 | | | | | |

| ggc | ata | ggg | aag | atg | ggc | ttt | gga | atg | gtg | act | ctt | ggg | gcc | agc | 6737 |
| Gly | Ile | Gly | Lys | Met | Gly | Phe | Gly | Met | Val | Thr | Leu | Gly | Ala | Ser | |
| | | 2200 | | | | 2205 | | | | 2210 | | | | | |

| gca | tgg | ctt | atg | tgg | ctc | tcg | gaa | att | gag | cca | gcc | aga | att | gca | 6782 |
| Ala | Trp | Leu | Met | Trp | Leu | Ser | Glu | Ile | Glu | Pro | Ala | Arg | Ile | Ala | |
| | | 2215 | | | | 2220 | | | | 2225 | | | | | |

| tgt | gtc | ctc | att | gtt | gtg | ttc | cta | ttg | ctg | gtg | gtg | ctc | ata | cct | 6827 |
| Cys | Val | Leu | Ile | Val | Val | Phe | Leu | Leu | Leu | Val | Val | Leu | Ile | Pro | |
| | | 2230 | | | | 2235 | | | | 2240 | | | | | |

| gag | cca | gaa | aag | caa | aga | tct | ccc | cag | gac | aac | caa | atg | gca | atc | 6872 |
| Glu | Pro | Glu | Lys | Gln | Arg | Ser | Pro | Gln | Asp | Asn | Gln | Met | Ala | Ile | |
| | | 2245 | | | | 2250 | | | | 2255 | | | | | |

| atc | atc | atg | gta | gca | gtg | ggt | ctt | ctg | ggc | ttg | att | acc | gcc | aat | 6917 |
| Ile | Ile | Met | Val | Ala | Val | Gly | Leu | Leu | Gly | Leu | Ile | Thr | Ala | Asn | |
| | | 2260 | | | | 2265 | | | | 2270 | | | | | |

| gaa | ctc | gga | tgg | ttg | gag | aga | aca | aag | agt | gac | cta | agc | cat | cta | 6962 |
| Glu | Leu | Gly | Trp | Leu | Glu | Arg | Thr | Lys | Ser | Asp | Leu | Ser | His | Leu | |
| | | 2275 | | | | 2280 | | | | 2285 | | | | | |

| atg | gga | agg | aga | gag | gag | ggg | gca | act | ata | gga | ttc | tca | atg | gac | 7007 |
| Met | Gly | Arg | Arg | Glu | Glu | Gly | Ala | Thr | Ile | Gly | Phe | Ser | Met | Asp | |
| | | 2290 | | | | 2295 | | | | 2300 | | | | | |

| att | gac | ctg | cgg | cca | gcc | tca | gct | tgg | gct | atc | tat | gct | gct | ctg | 7052 |
| Ile | Asp | Leu | Arg | Pro | Ala | Ser | Ala | Trp | Ala | Ile | Tyr | Ala | Ala | Leu | |
| | | 2305 | | | | 2310 | | | | 2315 | | | | | |

```
aca act ttc att acc cca gcc gtc caa cat gca gtg acc act tca      7097
Thr Thr Phe Ile Thr Pro Ala Val Gln His Ala Val Thr Thr Ser
            2320                2325                2330 tac aac aac tac tcc tta atg gcg atg gcc acg caa gct gga gtg      7142
Tyr Asn Asn Tyr Ser Leu Met Ala Met Ala Thr Gln Ala Gly Val
            2335                2340                2345 ttg ttc ggt atg ggt aaa ggg atg cca ttc tat gca tgg gac ttt      7187
Leu Phe Gly Met Gly Lys Gly Met Pro Phe Tyr Ala Trp Asp Phe
            2350                2355                2360 gga gtc ccg ctg cta atg ata ggt tgc tac tca caa tta aca ccc      7232
Gly Val Pro Leu Leu Met Ile Gly Cys Tyr Ser Gln Leu Thr Pro
            2365                2370                2375 ctg acc cta ata gtg gcc atc att ttg ctc gtg gcg cac tac atg      7277
Leu Thr Leu Ile Val Ala Ile Ile Leu Leu Val Ala His Tyr Met
            2380                2385                2390 tac ttg atc cca ggg ctg cag gca gca gct gcg cgt gct gcc cag      7322
Tyr Leu Ile Pro Gly Leu Gln Ala Ala Ala Ala Arg Ala Ala Gln
            2395                2400                2405 aag aga acg gca gct ggc atc atg aag aac cct gtt gtg gat gga      7367
Lys Arg Thr Ala Ala Gly Ile Met Lys Asn Pro Val Val Asp Gly
            2410                2415                2420 ata gtg gtg act gac att gac aca atg aca att gac ccc caa gtg      7412
Ile Val Val Thr Asp Ile Asp Thr Met Thr Ile Asp Pro Gln Val
            2425                2430                2435 gag aaa aag atg gga cag gtg cta ctc ata gca gta gct gtc tcc      7457
Glu Lys Lys Met Gly Gln Val Leu Leu Ile Ala Val Ala Val Ser
            2440                2445                2450 agc gcc ata ctg tcg cgg acc gcc tgg ggg tgg ggt gag gct ggg      7502
Ser Ala Ile Leu Ser Arg Thr Ala Trp Gly Trp Gly Glu Ala Gly
            2455                2460                2465 gcc ctg atc aca gct gca act tcc act ttg tgg gag ggc tct ccg      7547
Ala Leu Ile Thr Ala Ala Thr Ser Thr Leu Trp Glu Gly Ser Pro
            2470                2475                2480 aac aag tac tgg aac tcc tcc aca gcc acc tca ctg tgt aac att      7592
Asn Lys Tyr Trp Asn Ser Ser Thr Ala Thr Ser Leu Cys Asn Ile
            2485                2490                2495 ttt agg gga agc tac ttg gct gga gct tct cta atc tac aca gta      7637
Phe Arg Gly Ser Tyr Leu Ala Gly Ala Ser Leu Ile Tyr Thr Val
            2500                2505                2510 aca aga aac gct ggc ttg gtc aag aga cgt ggg ggt gga acg gga      7682
Thr Arg Asn Ala Gly Leu Val Lys Arg Arg Gly Gly Gly Thr Gly
            2515                2520                2525 gag acc ctg gga gag aaa tgg aag gcc cgc ctg aac cag atg tcg      7727
Glu Thr Leu Gly Glu Lys Trp Lys Ala Arg Leu Asn Gln Met Ser
            2530                2535                2540 gcc ctg gag ttc tac tcc tac aaa aag tca ggc atc acc gag gtg      7772
Ala Leu Glu Phe Tyr Ser Tyr Lys Lys Ser Gly Ile Thr Glu Val
            2545                2550                2555 tgc aga gaa gag gcc cgc cgc gcc ctc aag gac ggt gtg gca acg      7817
Cys Arg Glu Glu Ala Arg Arg Ala Leu Lys Asp Gly Val Ala Thr
            2560                2565                2570 gga ggc cac gct gtg tcc cga gga agt gca aag ctg aga tgg ttg      7862
Gly Gly His Ala Val Ser Arg Gly Ser Ala Lys Leu Arg Trp Leu
            2575                2580                2585 gtg gag agg gga tac ctg cag ccc tat gga aag gtc att gat ctt      7907
Val Glu Arg Gly Tyr Leu Gln Pro Tyr Gly Lys Val Ile Asp Leu
            2590                2595                2600 gga tgt ggc aga ggg ggc tgg agt tac tat gcc gcc acc atc cgc      7952
Gly Cys Gly Arg Gly Gly Trp Ser Tyr Tyr Ala Ala Thr Ile Arg
```

```
                    2605                2610                2615
aaa gtt caa gaa gtg  aaa gga tac aca aaa  gga ggc cct ggt cat     7997
Lys Val Gln Glu Val  Lys Gly Tyr Thr Lys  Gly Gly Pro Gly His
            2620                2625                2630 gaa gaa ccc atg ttg  gtg caa agc tat ggg  tgg aac ata gtc cgt     8042
Glu Glu Pro Met Leu  Val Gln Ser Tyr Gly  Trp Asn Ile Val Arg
            2635                2640                2645 ctt aag agt ggg gtg  gac gtc ttt cat atg  gcg gct gag ccg tgt     8087
Leu Lys Ser Gly Val  Asp Val Phe His Met  Ala Ala Glu Pro Cys
            2650                2655                2660 gac acg ttg ctg tgt  gat ata ggt gag tca  tca tct agt cct gaa     8132
Asp Thr Leu Leu Cys  Asp Ile Gly Glu Ser  Ser Ser Ser Pro Glu
            2665                2670                2675 gtg gaa gaa gca cgg  acg ctc aga gtc ctc  tcc atg gtg ggg gat     8177
Val Glu Glu Ala Arg  Thr Leu Arg Val Leu  Ser Met Val Gly Asp
            2680                2685                2690 tgg ctt gaa aaa aga  cca gga gcc ttt tgt  ata aaa gtg ttg tgc     8222
Trp Leu Glu Lys Arg  Pro Gly Ala Phe Cys  Ile Lys Val Leu Cys
            2695                2700                2705 cca tac acc agc act  atg atg gaa acc ctg  gag cga ctg cag cgt     8267
Pro Tyr Thr Ser Thr  Met Met Glu Thr Leu  Glu Arg Leu Gln Arg
            2710                2715                2720 agg tat ggg gga gga  ctg gtc aga gtg cca  ctc tcc cgc aac tct     8312
Arg Tyr Gly Gly Gly  Leu Val Arg Val Pro  Leu Ser Arg Asn Ser
            2725                2730                2735 aca cat gag atg tac  tgg gtc tct gga gcg  aaa agc aac acc ata     8357
Thr His Glu Met Tyr  Trp Val Ser Gly Ala  Lys Ser Asn Thr Ile
            2740                2745                2750 aaa agt gtg tcc acc  acg agc cag ctc ctt  ttg ggg cgc atg gac     8402
Lys Ser Val Ser Thr  Thr Ser Gln Leu Leu  Leu Gly Arg Met Asp
            2755                2760                2765 ggg ccc agg agg cca  gtg aaa tat gaa gag  gat gtg aat ctc ggc     8447
Gly Pro Arg Arg Pro  Val Lys Tyr Glu Glu  Asp Val Asn Leu Gly
            2770                2775                2780 tct ggc acg cgg gct  gtg gta agc tgc gct  gaa gct ccc aac atg     8492
Ser Gly Thr Arg Ala  Val Val Ser Cys Ala  Glu Ala Pro Asn Met
            2785                2790                2795 aag atc att ggt aac  cgc att gag agg atc  cgc agt gag cac gcg     8537
Lys Ile Ile Gly Asn  Arg Ile Glu Arg Ile  Arg Ser Glu His Ala
            2800                2805                2810 gaa acg tgg ttc ttt  gac gag aac cac cca  tat agg aca tgg gct     8582
Glu Thr Trp Phe Phe  Asp Glu Asn His Pro  Tyr Arg Thr Trp Ala
            2815                2820                2825 tac cat gga agc tac  gag gcc ccc aca caa  ggg tca gcg tcc tct     8627
Tyr His Gly Ser Tyr  Glu Ala Pro Thr Gln  Gly Ser Ala Ser Ser
            2830                2835                2840 cta ata aac ggg gtt  gtc agg ctc ctg tca  aaa ccc tgg gat gtg     8672
Leu Ile Asn Gly Val  Val Arg Leu Leu Ser  Lys Pro Trp Asp Val
            2845                2850                2855 gtg act gga gtc aca  gga ata gcc atg acc  gac acc aca ccg tat     8717
Val Thr Gly Val Thr  Gly Ile Ala Met Thr  Asp Thr Thr Pro Tyr
            2860                2865                2870 ggt cag caa aga gtt  ttc aag gaa aaa gtg  gac act agg gtg cca     8762
Gly Gln Gln Arg Val  Phe Lys Glu Lys Val  Asp Thr Arg Val Pro
            2875                2880                2885 gac ccc caa gaa ggc  act cgt cag gtt atg  agc atg gtc tct tcc     8807
Asp Pro Gln Glu Gly  Thr Arg Gln Val Met  Ser Met Val Ser Ser
            2890                2895                2900 tgg ttg tgg aaa gag  tta ggc aaa cac aaa  cgg cca cga gtc tgt     8852
```

|  |  |  |  |  |  |  |  |  |  |  |  |  |
|---|---|---|---|---|---|---|---|---|---|---|---|---|
| Trp | Leu | Trp | Lys | Glu<br>2905 | Leu | Gly | Lys | His | Lys<br>2910 | Arg | Pro | Arg | Val | Cys<br>2915 |

| acc | aaa | gaa | gag | ttc | atc | aac | aag | gtt | cgt | agc | aac | gca | gca | tta | 8897 |
| Thr | Lys | Glu | Glu | Phe<br>2920 | Ile | Asn | Lys | Val | Arg<br>2925 | Ser | Asn | Ala | Ala | Leu<br>2930 |

| ggg | gca | ata | ttt | gaa | gag | gaa | aaa | gag | tgg | aag | act | gca | gtg | gaa | 8942 |
| Gly | Ala | Ile | Phe | Glu<br>2935 | Glu | Glu | Lys | Glu | Trp<br>2940 | Lys | Thr | Ala | Val | Glu<br>2945 |

| gct | gtg | aac | gat | cca | agg | ttc | tgg | gct | cta | gtg | gac | aag | gaa | aga | 8987 |
| Ala | Val | Asn | Asp | Pro<br>2950 | Arg | Phe | Trp | Ala | Leu<br>2955 | Val | Asp | Lys | Glu | Arg<br>2960 |

| gag | cac | cac | ctg | aga | gga | gag | tgc | cag | agc | tgt | gtg | tac | aac | atg | 9032 |
| Glu | His | His | Leu | Arg<br>2965 | Gly | Glu | Cys | Gln | Ser<br>2970 | Cys | Val | Tyr | Asn | Met<br>2975 |

| atg | gga | aaa | aga | gaa | aag | aaa | caa | ggg | gaa | ttt | gga | aag | gcc | aag | 9077 |
| Met | Gly | Lys | Arg | Glu<br>2980 | Lys | Lys | Gln | Gly | Glu<br>2985 | Phe | Gly | Lys | Ala | Lys<br>2990 |

| ggc | agc | cgc | gcc | atc | tgg | tac | atg | tgg | cta | ggg | gct | aga | ttt | cta | 9122 |
| Gly | Ser | Arg | Ala | Ile<br>2995 | Trp | Tyr | Met | Trp | Leu<br>3000 | Gly | Ala | Arg | Phe | Leu<br>3005 |

| gag | ttc | gaa | gcc | ctt | gga | ttc | ttg | aac | gag | gat | cac | tgg | atg | ggg | 9167 |
| Glu | Phe | Glu | Ala | Leu<br>3010 | Gly | Phe | Leu | Asn | Glu<br>3015 | Asp | His | Trp | Met | Gly<br>3020 |

| aga | gag | aat | tca | gga | ggt | ggt | gtt | gaa | ggg | cta | gga | tta | caa | aga | 9212 |
| Arg | Glu | Asn | Ser | Gly<br>3025 | Gly | Gly | Val | Glu | Gly<br>3030 | Leu | Gly | Leu | Gln | Arg<br>3035 |

| ctc | gga | tat | gtc | tta | gaa | gag | atg | agt | cgc | ata | cca | gga | gga | agg | 9257 |
| Leu | Gly | Tyr | Val | Leu<br>3040 | Glu | Glu | Met | Ser | Arg<br>3045 | Ile | Pro | Gly | Gly | Arg<br>3050 |

| atg | tat | gca | gat | gat | act | gct | ggc | tgg | gac | acc | cgc | atc | agc | agg | 9302 |
| Met | Tyr | Ala | Asp | Asp<br>3055 | Thr | Ala | Gly | Trp | Asp<br>3060 | Thr | Arg | Ile | Ser | Arg<br>3065 |

| ttt | gat | ctg | gag | aat | gaa | gct | cta | atc | acc | aac | caa | atg | gag | aaa | 9347 |
| Phe | Asp | Leu | Glu | Asn<br>3070 | Glu | Ala | Leu | Ile | Thr<br>3075 | Asn | Gln | Met | Glu | Lys<br>3080 |

| ggg | cac | agg | gcc | ttg | gca | ttg | gcc | ata | atc | aag | tac | aca | tac | caa | 9392 |
| Gly | His | Arg | Ala | Leu<br>3085 | Ala | Leu | Ala | Ile | Ile<br>3090 | Lys | Tyr | Thr | Tyr | Gln<br>3095 |

| aac | aaa | gtg | gta | aag | gtc | ctt | aga | cca | gct | gaa | aaa | ggg | aag | aca | 9437 |
| Asn | Lys | Val | Val | Lys<br>3100 | Val | Leu | Arg | Pro | Ala<br>3105 | Glu | Lys | Gly | Lys | Thr<br>3110 |

| gtt | atg | gac | att | att | tca | aga | caa | gac | caa | agg | ggg | agc | gga | caa | 9482 |
| Val | Met | Asp | Ile | Ile<br>3115 | Ser | Arg | Gln | Asp | Gln<br>3120 | Arg | Gly | Ser | Gly | Gln<br>3125 |

| gtt | gtc | act | tac | gct | ctt | aat | aca | ttt | acc | aac | cta | gtg | gtg | cag | 9527 |
| Val | Val | Thr | Tyr | Ala<br>3130 | Leu | Asn | Thr | Phe | Thr<br>3135 | Asn | Leu | Val | Val | Gln<br>3140 |

| ctc | att | cgg | aat | atg | gag | gct | gag | gaa | gtt | cta | gag | atg | caa | gac | 9572 |
| Leu | Ile | Arg | Asn | Met<br>3145 | Glu | Ala | Glu | Glu | Val<br>3150 | Leu | Glu | Met | Gln | Asp<br>3155 |

| ttg | tgg | ctg | ctg | cgg | agg | tca | gag | aaa | gtg | acc | aac | tgg | ttg | cag | 9617 |
| Leu | Trp | Leu | Leu | Arg<br>3160 | Arg | Ser | Glu | Lys | Val<br>3165 | Thr | Asn | Trp | Leu | Gln<br>3170 |

| agc | aat | gga | tgg | gat | agg | ctc | aaa | cga | atg | gca | gtc | agt | gga | gat | 9662 |
| Ser | Asn | Gly | Trp | Asp<br>3175 | Arg | Leu | Lys | Arg | Met<br>3180 | Ala | Val | Ser | Gly | Asp<br>3185 |

| gat | tgc | gtt | gtg | aaa | cca | att | gat | gat | agg | ttt | gca | cat | gct | ctc | 9707 |
| Asp | Cys | Val | Val | Lys<br>3190 | Pro | Ile | Asp | Asp | Arg<br>3195 | Phe | Ala | His | Ala | Leu<br>3200 |

| | |
|---|---|
| agg ttc ttg aat gat atg gga aaa gtt agg aag gac aca caa gag<br>Arg Phe Leu Asn Asp Met Gly Lys Val Arg Lys Asp Thr Gln Glu<br>3205 3210 3215 | 9752 |
| tgg aag ccc tca act gga tgg gac aac tgg gaa gaa gtt ccg ttt<br>Trp Lys Pro Ser Thr Gly Trp Asp Asn Trp Glu Glu Val Pro Phe<br>3220 3225 3230 | 9797 |
| tgc tcc cac cac ttc aac aag ctc cat ctc aag gac ggg agg tcc<br>Cys Ser His His Phe Asn Lys Leu His Leu Lys Asp Gly Arg Ser<br>3235 3240 3245 | 9842 |
| att gtg gtt ccc tgc cgc cac caa gat gaa ctg att ggc cga gct<br>Ile Val Val Pro Cys Arg His Gln Asp Glu Leu Ile Gly Arg Ala<br>3250 3255 3260 | 9887 |
| cgc gtc tca ccg ggg gcg gga tgg agc atc cgg gag act gct tgc<br>Arg Val Ser Pro Gly Ala Gly Trp Ser Ile Arg Glu Thr Ala Cys<br>3265 3270 3275 | 9932 |
| cta gca aaa tca tat gcg caa atg tgg cag ctc ctt tat ttc cac<br>Leu Ala Lys Ser Tyr Ala Gln Met Trp Gln Leu Leu Tyr Phe His<br>3280 3285 3290 | 9977 |
| aga agg gac ctc cga ctg atg gcc aat gcc att tgt tca tct gtg<br>Arg Arg Asp Leu Arg Leu Met Ala Asn Ala Ile Cys Ser Ser Val<br>3295 3300 3305 | 10022 |
| cca gtt gac tgg gtt cca act ggg aga act acc tgg tca atc cat<br>Pro Val Asp Trp Val Pro Thr Gly Arg Thr Thr Trp Ser Ile His<br>3310 3315 3320 | 10067 |
| gga aag gga gaa tgg atg acc act gaa gac atg ctt gtg gtg tgg<br>Gly Lys Gly Glu Trp Met Thr Thr Glu Asp Met Leu Val Val Trp<br>3325 3330 3335 | 10112 |
| aac aga gtg tgg att gag gag aac gac cac atg gaa gac aag acc<br>Asn Arg Val Trp Ile Glu Glu Asn Asp His Met Glu Asp Lys Thr<br>3340 3345 3350 | 10157 |
| cca gtt acg aaa tgg aca gac att ccc tat ttg gga aaa agg gaa<br>Pro Val Thr Lys Trp Thr Asp Ile Pro Tyr Leu Gly Lys Arg Glu<br>3355 3360 3365 | 10202 |
| gac ttg tgg tgt ggg tct ctc ata ggg cac aga ccg cgc acc acc<br>Asp Leu Trp Cys Gly Ser Leu Ile Gly His Arg Pro Arg Thr Thr<br>3370 3375 3380 | 10247 |
| tgg gct gag aac att aaa aac aca gtc aac atg atg cgt agg atc<br>Trp Ala Glu Asn Ile Lys Asn Thr Val Asn Met Met Arg Arg Ile<br>3385 3390 3395 | 10292 |
| ata ggt gat gaa gaa aag tac gtg gac tac cta tcc acc caa gtt<br>Ile Gly Asp Glu Glu Lys Tyr Val Asp Tyr Leu Ser Thr Gln Val<br>3400 3405 3410 | 10337 |
| cgc tac ttg ggc gaa gaa ggg tcc aca cct gga gtg cta taa<br>Arg Tyr Leu Gly Glu Glu Gly Ser Thr Pro Gly Val Leu<br>3415 3420 | 10379 |
| gcaccaatct tagtgttgtc aggcctgcta gtcagccaca gcttgggaa agctgtgcag | 10439 |
| cctgtgaccc ccccaggaga agctgggaaa ccaagcccat agtcaggccg agaacgccat | 10499 |
| ggcacggaag aagccatgct gcctgtgagc ccctcagagg acactgagtc aaaaaacccc | 10559 |
| acgcgcttgg aggcgcagga tgggaaaaga aggtggcgac cttccccacc ctttaatctg | 10619 |
| gggcctgaac tggagatcag ctgtggatct ccagaagagg gactagtggt tagaggagac | 10679 |
| cccccgaaa acgcaaaaca gcatattgac gctgggaaag accagagact ccatgagttt | 10739 |
| ccaccacgct ggccgccagg cacagatcgc cgaatagcgg cggccggtgt ggggaaatcc | 10799 |
| atgggtct | 10807 |

<210> SEQ ID NO 11
<211> LENGTH: 3423

```
<212> TYPE: PRT
<213> ORGANISM: Zika virus
<300> PUBLICATION INFORMATION:
<308> DATABASE ACCESSION NUMBER: KU955593.1
<309> DATABASE ENTRY DATE: 2016-05-24
<313> RELEVANT RESIDUES IN SEQ ID NO: (1)..(3423)

<400> SEQUENCE: 11
```

| | | | | | | | | | | | | | | |
|---|---|---|---|---|---|---|---|---|---|---|---|---|---|---|
| Met | Lys | Asn | Pro | Lys | Lys | Lys | Ser | Gly | Gly | Phe | Arg | Ile | Val | Asn | Met |
| 1 | | | | 5 | | | | | 10 | | | | | 15 | |
| Leu | Lys | Arg | Gly | Val | Ala | Arg | Val | Ser | Pro | Phe | Gly | Gly | Leu | Lys | Arg |
| | | | 20 | | | | | 25 | | | | | 30 | | |
| Leu | Pro | Ala | Gly | Leu | Leu | Leu | Gly | His | Gly | Pro | Ile | Arg | Met | Val | Leu |
| | | 35 | | | | | 40 | | | | | 45 | | | |
| Ala | Ile | Leu | Ala | Phe | Leu | Arg | Phe | Thr | Ala | Ile | Lys | Pro | Ser | Leu | Gly |
| 50 | | | | | 55 | | | | | 60 | | | | | |
| Leu | Ile | Asn | Arg | Trp | Gly | Ser | Val | Gly | Lys | Lys | Glu | Ala | Met | Glu | Ile |
| 65 | | | | 70 | | | | | 75 | | | | | 80 | |
| Ile | Lys | Lys | Phe | Lys | Lys | Asp | Leu | Ala | Ala | Met | Leu | Arg | Ile | Ile | Asn |
| | | | | 85 | | | | | 90 | | | | | 95 | |
| Ala | Arg | Lys | Glu | Lys | Lys | Arg | Arg | Gly | Thr | Asp | Thr | Ser | Val | Gly | Ile |
| | | | 100 | | | | | 105 | | | | | 110 | | |
| Val | Gly | Leu | Leu | Leu | Thr | Thr | Ala | Met | Ala | Val | Glu | Val | Thr | Arg | Arg |
| | | 115 | | | | | 120 | | | | | 125 | | | |
| Gly | Asn | Ala | Tyr | Tyr | Met | Tyr | Leu | Asp | Arg | Ser | Asp | Ala | Gly | Glu | Ala |
| | 130 | | | | | 135 | | | | | 140 | | | | |
| Ile | Ser | Phe | Pro | Thr | Thr | Met | Gly | Met | Asn | Lys | Cys | Tyr | Ile | Gln | Ile |
| 145 | | | | | 150 | | | | | 155 | | | | | 160 |
| Met | Asp | Leu | Gly | His | Met | Cys | Asp | Ala | Thr | Met | Ser | Tyr | Glu | Cys | Pro |
| | | | | 165 | | | | | 170 | | | | | 175 | |
| Met | Leu | Asp | Glu | Gly | Val | Glu | Pro | Asp | Asp | Val | Asp | Cys | Trp | Cys | Asn |
| | | | 180 | | | | | 185 | | | | | 190 | | |
| Thr | Thr | Ser | Thr | Trp | Val | Val | Tyr | Gly | Thr | Cys | His | His | Lys | Lys | Gly |
| | | 195 | | | | | 200 | | | | | 205 | | | |
| Glu | Ala | Arg | Arg | Ser | Arg | Arg | Ala | Val | Thr | Leu | Pro | Ser | His | Ser | Thr |
| | 210 | | | | | 215 | | | | | 220 | | | | |
| Arg | Lys | Leu | Gln | Thr | Arg | Ser | Gln | Thr | Trp | Leu | Glu | Ser | Arg | Glu | Tyr |
| 225 | | | | | 230 | | | | | 235 | | | | | 240 |
| Thr | Lys | His | Leu | Ile | Arg | Val | Glu | Asn | Trp | Ile | Phe | Arg | Asn | Pro | Gly |
| | | | | 245 | | | | | 250 | | | | | 255 | |
| Phe | Ala | Leu | Ala | Ala | Ala | Ala | Ile | Ala | Trp | Leu | Leu | Gly | Ser | Ser | Thr |
| | | | 260 | | | | | 265 | | | | | 270 | | |
| Ser | Gln | Lys | Val | Ile | Tyr | Leu | Val | Met | Ile | Leu | Leu | Ile | Ala | Pro | Ala |
| | | 275 | | | | | 280 | | | | | 285 | | | |
| Tyr | Ser | Ile | Arg | Cys | Ile | Gly | Val | Ser | Asn | Arg | Asp | Phe | Val | Glu | Gly |
| | 290 | | | | | 295 | | | | | 300 | | | | |
| Met | Ser | Gly | Gly | Thr | Trp | Val | Asp | Val | Leu | Glu | His | Gly | Gly | Cys |
| 305 | | | | | 310 | | | | | 315 | | | | | 320 |
| Val | Thr | Val | Met | Ala | Gln | Asp | Lys | Pro | Thr | Val | Asp | Ile | Glu | Leu | Val |
| | | | | 325 | | | | | 330 | | | | | 335 | |
| Thr | Thr | Thr | Val | Ser | Asn | Met | Ala | Glu | Val | Arg | Ser | Tyr | Cys | Tyr | Glu |
| | | | 340 | | | | | 345 | | | | | 350 | | |
| Ala | Ser | Ile | Ser | Asp | Met | Ala | Ser | Asp | Ser | Arg | Cys | Pro | Thr | Gln | Gly |
| | | 355 | | | | | 360 | | | | | 365 | | | |
| Glu | Ala | Tyr | Leu | Asp | Lys | Gln | Ser | Asp | Thr | Gln | Tyr | Val | Cys | Lys | Arg |

-continued

```
            370                 375                 380
Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
                420                 425                 430

Val His Gly Ser Gln His Ser Gly Met Ile Val Asn Asp Thr Gly His
                435                 440                 445

Glu Thr Asp Glu Asn Arg Ala Lys Val Glu Ile Thr Pro Asn Ser Pro
450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
                500                 505                 510

Leu Pro Trp His Ala Gly Ala Asp Thr Gly Thr Pro His Trp Asn Asn
                515                 520                 525

Lys Glu Ala Leu Val Glu Phe Lys Asp Ala His Ala Lys Arg Gln Thr
                530                 535                 540

Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
                580                 585                 590

Val Ser Tyr Ser Leu Cys Thr Ala Ala Phe Thr Phe Thr Lys Ile Pro
                595                 600                 605

Ala Glu Thr Leu His Gly Thr Val Thr Val Glu Val Gln Tyr Ala Gly
                610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
                660                 665                 670

Gly Asp Ser Tyr Ile Val Ile Gly Val Gly Glu Lys Lys Ile Thr His
                675                 680                 685

His Trp His Arg Ser Gly Ser Thr Ile Gly Lys Ala Phe Glu Ala Thr
                690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
                740                 745                 750

Phe Ser Gln Ile Leu Ile Gly Thr Leu Leu Val Trp Leu Gly Leu Asn
                755                 760                 765

Thr Lys Asn Gly Ser Ile Ser Leu Met Cys Leu Ala Leu Gly Gly Val
                770                 775                 780

Leu Ile Phe Leu Ser Thr Ala Val Ser Ala Asp Val Gly Cys Ser Val
785                 790                 795                 800
```

```
Asp Phe Ser Lys Lys Glu Thr Arg Cys Gly Thr Gly Val Phe Val Tyr
            805                 810                 815

Asn Asp Val Glu Ala Trp Arg Asp Arg Tyr Lys Tyr His Pro Asp Ser
            820                 825                 830

Pro Arg Arg Leu Ala Ala Val Lys Gln Ala Trp Glu Asp Gly Ile
            835                 840                 845

Cys Gly Ile Ser Ser Val Ser Arg Met Glu Asn Ile Met Trp Arg Ser
            850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                    885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
            915                 920                 925

Val Asp Gly Asp Thr Leu Lys Glu Cys Pro Leu Lys His Arg Ala Trp
930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Ala Lys Gly Lys Glu Ala Val His Ser Asp Leu
            980                 985                 990

Gly Tyr Trp Ile Glu Ser Glu Lys Asn Asp Thr Trp Arg Leu Lys Arg
            995                 1000                1005

Ala His Leu Ile Glu Met Lys Thr Cys Glu Trp Pro Lys Ser His
    1010                1015                1020

Thr Leu Trp Thr Asp Gly Ile Glu Glu Ser Asp Leu Ile Ile Pro
    1025                1030                1035

Lys Ser Leu Ala Gly Pro Leu Ser His His Asn Thr Arg Glu Gly
    1040                1045                1050

Tyr Arg Thr Gln Met Lys Gly Pro Trp His Ser Glu Glu Leu Glu
    1055                1060                1065

Ile Arg Phe Glu Glu Cys Pro Gly Thr Lys Val His Val Glu Glu
    1070                1075                1080

Thr Cys Gly Thr Arg Gly Pro Ser Leu Arg Ser Thr Thr Ala Ser
    1085                1090                1095

Gly Arg Val Ile Glu Glu Trp Cys Cys Arg Glu Cys Thr Met Pro
    1100                1105                1110

Pro Leu Ser Phe Arg Ala Lys Asp Gly Cys Trp Tyr Gly Met Glu
    1115                1120                1125

Ile Arg Pro Arg Lys Glu Pro Glu Ser Asn Leu Val Arg Ser Met
    1130                1135                1140

Val Thr Ala Gly Ser Thr Asp His Met Asp His Phe Ser Leu Gly
    1145                1150                1155

Val Leu Val Ile Leu Leu Met Val Gln Glu Gly Leu Lys Lys Arg
    1160                1165                1170

Met Thr Thr Lys Ile Ile Ile Ser Thr Ser Met Ala Val Leu Val
    1175                1180                1185

Ala Met Ile Leu Gly Gly Phe Ser Met Ser Asp Leu Ala Lys Leu
    1190                1195                1200
```

```
Ala Ile Leu Met Gly Ala Thr Phe Ala Glu Met Asn Thr Gly Gly
1205                    1210                    1215

Asp Val Ala His Leu Ala Leu Ile Ala Ala Phe Lys Val Arg Pro
1220                    1225                    1230

Ala Leu Leu Val Ser Phe Ile Phe Arg Ala Asn Trp Thr Pro Arg
1235                    1240                    1245

Glu Ser Met Leu Leu Ala Leu Ala Ser Cys Leu Leu Gln Thr Ala
1250                    1255                    1260

Ile Ser Ala Leu Glu Gly Asp Leu Met Val Pro Ile Asn Gly Phe
1265                    1270                    1275

Ala Leu Ala Trp Leu Ala Ile Arg Ala Met Val Val Pro Arg Thr
1280                    1285                    1290

Asp Asn Ile Thr Leu Ala Ile Leu Ala Ala Leu Thr Pro Leu Ala
1295                    1300                    1305

Arg Gly Thr Leu Leu Val Ala Trp Arg Ala Gly Leu Ala Thr Cys
1310                    1315                    1320

Gly Gly Phe Met Leu Leu Ser Leu Lys Gly Lys Gly Ser Val Lys
1325                    1330                    1335

Lys Asn Leu Pro Phe Val Met Ala Leu Gly Leu Thr Ala Val Arg
1340                    1345                    1350

Leu Val Asp Pro Ile Asn Val Val Gly Leu Leu Leu Leu Thr Arg
1355                    1360                    1365

Ser Gly Lys Arg Ser Trp Pro Pro Ser Glu Val Leu Thr Ala Val
1370                    1375                    1380

Gly Leu Ile Cys Ala Leu Ala Gly Gly Phe Ala Lys Ala Asp Ile
1385                    1390                    1395

Glu Met Ala Gly Pro Met Ala Ala Val Gly Leu Leu Ile Val Ser
1400                    1405                    1410

Tyr Val Val Ser Gly Lys Ser Val Asp Met Tyr Ile Glu Arg Ala
1415                    1420                    1425

Gly Asp Ile Thr Trp Glu Lys Asp Ala Glu Val Thr Gly Asn Ser
1430                    1435                    1440

Pro Arg Leu Asp Val Ala Leu Asp Glu Ser Gly Asp Phe Ser Leu
1445                    1450                    1455

Val Glu Asp Asp Gly Pro Pro Met Arg Glu Ile Ile Leu Lys Val
1460                    1465                    1470

Val Leu Met Ala Ile Cys Gly Met Asn Pro Ile Ala Ile Pro Phe
1475                    1480                    1485

Ala Ala Gly Ala Trp Tyr Val Tyr Val Lys Thr Gly Lys Arg Ser
1490                    1495                    1500

Gly Ala Leu Trp Asp Val Pro Ala Pro Lys Glu Val Lys Lys Gly
1505                    1510                    1515

Glu Thr Thr Asp Gly Val Tyr Arg Val Met Thr Arg Arg Leu Leu
1520                    1525                    1530

Gly Ser Thr Gln Val Gly Val Gly Val Met Gln Glu Gly Val Phe
1535                    1540                    1545

His Thr Met Trp His Val Thr Lys Gly Ser Ala Leu Arg Ser Gly
1550                    1555                    1560

Glu Gly Arg Leu Asp Pro Tyr Trp Gly Asp Val Lys Gln Asp Leu
1565                    1570                    1575

Val Ser Tyr Cys Gly Pro Trp Lys Leu Asp Ala Ala Trp Asp Gly
1580                    1585                    1590

His Ser Glu Val Gln Leu Leu Ala Val Pro Pro Gly Glu Arg Ala
```

-continued

```
            1595                1600                1605
Arg  Asn  Ile  Gln  Thr  Leu  Pro  Gly  Ile  Phe  Lys  Thr  Lys  Asp  Gly
            1610                1615                1620
Asp  Ile  Gly  Ala  Val  Ala  Leu  Asp  Tyr  Pro  Ala  Gly  Thr  Ser  Gly
            1625                1630                1635
Ser  Pro  Ile  Leu  Asp  Lys  Cys  Gly  Arg  Val  Ile  Gly  Leu  Tyr  Gly
            1640                1645                1650
Asn  Gly  Val  Val  Ile  Lys  Asn  Gly  Ser  Tyr  Val  Ser  Ala  Ile  Thr
            1655                1660                1665
Gln  Gly  Arg  Arg  Glu  Glu  Glu  Thr  Pro  Val  Glu  Cys  Phe  Glu  Pro
            1670                1675                1680
Ser  Met  Leu  Lys  Lys  Lys  Gln  Leu  Thr  Val  Leu  Asp  Leu  His  Pro
            1685                1690                1695
Gly  Ala  Gly  Lys  Thr  Arg  Arg  Val  Leu  Pro  Glu  Ile  Val  Arg  Glu
            1700                1705                1710
Ala  Ile  Lys  Thr  Arg  Leu  Arg  Thr  Val  Ile  Leu  Ala  Pro  Thr  Arg
            1715                1720                1725
Val  Val  Ala  Ala  Glu  Met  Glu  Glu  Ala  Leu  Arg  Gly  Leu  Pro  Val
            1730                1735                1740
Arg  Tyr  Met  Thr  Thr  Ala  Val  Asn  Val  Thr  His  Ser  Gly  Thr  Glu
            1745                1750                1755
Ile  Val  Asp  Leu  Met  Cys  His  Ala  Thr  Phe  Thr  Ser  Arg  Leu  Leu
            1760                1765                1770
Gln  Pro  Ile  Arg  Val  Pro  Asn  Tyr  Asn  Leu  Tyr  Ile  Met  Asp  Glu
            1775                1780                1785
Ala  His  Phe  Thr  Asp  Pro  Ser  Ser  Ile  Ala  Ala  Arg  Gly  Tyr  Ile
            1790                1795                1800
Ser  Thr  Arg  Val  Glu  Met  Gly  Glu  Ala  Ala  Ala  Ile  Phe  Met  Thr
            1805                1810                1815
Ala  Thr  Pro  Pro  Gly  Thr  Arg  Asp  Ala  Phe  Pro  Asp  Ser  Asn  Ser
            1820                1825                1830
Pro  Ile  Met  Asp  Thr  Glu  Val  Glu  Val  Pro  Glu  Arg  Ala  Trp  Ser
            1835                1840                1845
Ser  Gly  Phe  Asp  Trp  Val  Thr  Asp  His  Ser  Gly  Lys  Thr  Val  Trp
            1850                1855                1860
Phe  Val  Pro  Ser  Val  Arg  Asn  Gly  Asn  Glu  Ile  Ala  Ala  Cys  Leu
            1865                1870                1875
Thr  Lys  Ala  Gly  Lys  Arg  Val  Ile  Gln  Leu  Ser  Arg  Lys  Thr  Phe
            1880                1885                1890
Glu  Thr  Glu  Phe  Gln  Lys  Thr  Lys  His  Gln  Glu  Trp  Asp  Phe  Val
            1895                1900                1905
Val  Thr  Thr  Asp  Ile  Ser  Glu  Met  Gly  Ala  Asn  Phe  Lys  Ala  Asp
            1910                1915                1920
Arg  Val  Ile  Asp  Ser  Arg  Arg  Cys  Leu  Lys  Pro  Val  Ile  Leu  Asp
            1925                1930                1935
Gly  Glu  Arg  Val  Ile  Leu  Ala  Gly  Pro  Met  Pro  Val  Thr  His  Ala
            1940                1945                1950
Ser  Ala  Ala  Gln  Arg  Arg  Gly  Arg  Ile  Gly  Arg  Asn  Pro  Asn  Lys
            1955                1960                1965
Pro  Gly  Asp  Glu  Tyr  Leu  Tyr  Gly  Gly  Gly  Cys  Ala  Glu  Thr  Asp
            1970                1975                1980
Glu  Asp  His  Ala  His  Trp  Leu  Glu  Ala  Arg  Met  Leu  Leu  Asp  Asn
            1985                1990                1995
```

```
Ile Tyr Leu Gln Asp Gly Leu Ile Ala Ser Leu Tyr Arg Pro Glu
2000           2005              2010

Ala Asp Lys Val Ala Ala Ile Glu Gly Glu Phe Lys Leu Arg Thr
2015           2020              2025

Glu Gln Arg Lys Thr Phe Val Glu Leu Met Lys Arg Gly Asp Leu
2030           2035              2040

Pro Val Trp Leu Ala Tyr Gln Val Ala Ser Ala Gly Ile Thr Tyr
2045           2050              2055

Thr Asp Arg Arg Trp Cys Phe Asp Gly Thr Thr Asn Asn Thr Ile
2060           2065              2070

Met Glu Asp Ser Val Pro Ala Glu Val Trp Thr Arg Tyr Gly Glu
2075           2080              2085

Lys Arg Val Leu Lys Pro Arg Trp Met Asp Ala Arg Val Cys Ser
2090           2095              2100

Asp His Ala Ala Leu Lys Ser Phe Lys Glu Phe Ala Ala Gly Lys
2105           2110              2115

Arg Gly Ala Ala Phe Gly Val Met Glu Ala Leu Gly Thr Leu Pro
2120           2125              2130

Gly His Met Thr Glu Arg Phe Gln Glu Ala Ile Asp Asn Leu Ala
2135           2140              2145

Val Leu Met Arg Ala Glu Thr Gly Ser Arg Pro Tyr Lys Ala Ala
2150           2155              2160

Ala Ala Gln Leu Pro Glu Thr Leu Glu Thr Ile Met Leu Leu Gly
2165           2170              2175

Leu Leu Gly Thr Val Ser Leu Gly Ile Phe Phe Val Leu Met Arg
2180           2185              2190

Asn Lys Gly Ile Gly Lys Met Gly Phe Gly Met Val Thr Leu Gly
2195           2200              2205

Ala Ser Ala Trp Leu Met Trp Leu Ser Glu Ile Glu Pro Ala Arg
2210           2215              2220

Ile Ala Cys Val Leu Ile Val Val Phe Leu Leu Leu Val Val Leu
2225           2230              2235

Ile Pro Glu Pro Glu Lys Gln Arg Ser Pro Gln Asp Asn Gln Met
2240           2245              2250

Ala Ile Ile Ile Met Val Ala Val Gly Leu Leu Gly Leu Ile Thr
2255           2260              2265

Ala Asn Glu Leu Gly Trp Leu Glu Arg Thr Lys Ser Asp Leu Ser
2270           2275              2280

His Leu Met Gly Arg Arg Glu Glu Gly Ala Thr Ile Gly Phe Ser
2285           2290              2295

Met Asp Ile Asp Leu Arg Pro Ala Ser Ala Trp Ala Ile Tyr Ala
2300           2305              2310

Ala Leu Thr Thr Phe Ile Thr Pro Ala Val Gln His Ala Val Thr
2315           2320              2325

Thr Ser Tyr Asn Asn Tyr Ser Leu Met Ala Met Ala Thr Gln Ala
2330           2335              2340

Gly Val Leu Phe Gly Met Gly Lys Gly Met Pro Phe Tyr Ala Trp
2345           2350              2355

Asp Phe Gly Val Pro Leu Leu Met Ile Gly Cys Tyr Ser Gln Leu
2360           2365              2370

Thr Pro Leu Thr Leu Ile Val Ala Ile Ile Leu Leu Val Ala His
2375           2380              2385
```

-continued

| | | | | | | | | | | | |
|---|---|---|---|---|---|---|---|---|---|---|---|
|Tyr|Met|Tyr|Leu|Ile|Pro|Gly|Leu|Gln|Ala|Ala|Ala Arg Ala|
| |2390| | | |2395| | | |2400| | |
|Ala|Gln|Lys|Arg|Thr|Ala|Ala|Gly|Ile|Met|Lys|Asn Pro Val Val|
|2405| | | | |2410| | | |2415| | |
|Asp|Gly|Ile|Val|Val|Thr|Asp|Ile|Asp|Thr|Met|Thr Ile Asp Pro|
|2420| | | | |2425| | | |2430| | |
|Gln|Val|Glu|Lys|Lys|Met|Gly|Gln|Val|Leu|Leu|Ile Ala Val Ala|
|2435| | | | |2440| | | |2445| | |
|Val|Ser|Ser|Ala|Ile|Leu|Ser|Arg|Thr|Ala|Trp|Gly Trp Gly Glu|
|2450| | | | |2455| | | |2460| | |
|Ala|Gly|Ala|Leu|Ile|Thr|Ala|Ala|Thr|Ser|Thr|Leu Trp Glu Gly|
|2465| | | | |2470| | | |2475| | |
|Ser|Pro|Asn|Lys|Tyr|Trp|Asn|Ser|Ser|Thr|Ala|Thr Ser Leu Cys|
|2480| | | | |2485| | | |2490| | |
|Asn|Ile|Phe|Arg|Gly|Ser|Tyr|Leu|Ala|Gly|Ala|Ser Leu Ile Tyr|
|2495| | | | |2500| | | |2505| | |
|Thr|Val|Thr|Arg|Asn|Ala|Gly|Leu|Val|Lys|Arg|Arg Gly Gly Gly|
|2510| | | | |2515| | | |2520| | |
|Thr|Gly|Glu|Thr|Leu|Gly|Glu|Lys|Trp|Lys|Ala|Arg Leu Asn Gln|
|2525| | | | |2530| | | |2535| | |
|Met|Ser|Ala|Leu|Glu|Phe|Tyr|Ser|Tyr|Lys|Lys|Ser Gly Ile Thr|
|2540| | | | |2545| | | |2550| | |
|Glu|Val|Cys|Arg|Glu|Glu|Ala|Arg|Arg|Ala|Leu|Lys Asp Gly Val|
|2555| | | | |2560| | | |2565| | |
|Ala|Thr|Gly|Gly|His|Ala|Val|Ser|Arg|Gly|Ser|Ala Lys Leu Arg|
|2570| | | | |2575| | | |2580| | |
|Trp|Leu|Val|Glu|Arg|Gly|Tyr|Leu|Gln|Pro|Tyr|Gly Lys Val Ile|
|2585| | | | |2590| | | |2595| | |
|Asp|Leu|Gly|Cys|Gly|Arg|Gly|Gly|Trp|Ser|Tyr|Tyr Ala Ala Thr|
|2600| | | | |2605| | | |2610| | |
|Ile|Arg|Lys|Val|Gln|Glu|Val|Lys|Gly|Tyr|Thr|Lys Gly Gly Pro|
|2615| | | | |2620| | | |2625| | |
|Gly|His|Glu|Glu|Pro|Met|Leu|Val|Gln|Ser|Tyr|Gly Trp Asn Ile|
|2630| | | | |2635| | | |2640| | |
|Val|Arg|Leu|Lys|Ser|Gly|Val|Asp|Val|Phe|His|Met Ala Ala Glu|
|2645| | | | |2650| | | |2655| | |
|Pro|Cys|Asp|Thr|Leu|Leu|Cys|Asp|Ile|Gly|Glu|Ser Ser Ser Ser|
|2660| | | | |2665| | | |2670| | |
|Pro|Glu|Val|Glu|Glu|Ala|Arg|Thr|Leu|Arg|Val|Leu Ser Met Val|
|2675| | | | |2680| | | |2685| | |
|Gly|Asp|Trp|Leu|Glu|Lys|Arg|Pro|Gly|Ala|Phe|Cys Ile Lys Val|
|2690| | | | |2695| | | |2700| | |
|Leu|Cys|Pro|Tyr|Thr|Ser|Thr|Met|Met|Glu|Thr|Leu Glu Arg Leu|
|2705| | | | |2710| | | |2715| | |
|Gln|Arg|Arg|Tyr|Gly|Gly|Gly|Leu|Val|Arg|Val|Pro Leu Ser Arg|
|2720| | | | |2725| | | |2730| | |
|Asn|Ser|Thr|His|Glu|Met|Tyr|Trp|Val|Ser|Gly|Ala Lys Ser Asn|
|2735| | | | |2740| | | |2745| | |
|Thr|Ile|Lys|Ser|Val|Ser|Thr|Thr|Ser|Gln|Leu|Leu Leu Gly Arg|
|2750| | | | |2755| | | |2760| | |
|Met|Asp|Gly|Pro|Arg|Arg|Pro|Val|Lys|Tyr|Glu|Glu Asp Val Asn|
|2765| | | | |2770| | | |2775| | |
|Leu|Gly|Ser|Gly|Thr|Arg|Ala|Val|Val|Ser|Cys|Ala Glu Ala Pro|

```
                    2780              2785              2790
Asn Met Lys Ile Ile Gly Asn Arg Ile Glu Arg Ile Arg Ser Glu
    2795              2800              2805
His Ala Glu Thr Trp Phe Phe Asp Glu Asn His Pro Tyr Arg Thr
    2810              2815              2820
Trp Ala Tyr His Gly Ser Tyr Glu Ala Pro Thr Gln Gly Ser Ala
    2825              2830              2835
Ser Ser Leu Ile Asn Gly Val Val Arg Leu Leu Ser Lys Pro Trp
    2840              2845              2850
Asp Val Val Thr Gly Val Thr Gly Ile Ala Met Thr Asp Thr Thr
    2855              2860              2865
Pro Tyr Gly Gln Gln Arg Val Phe Lys Glu Lys Val Asp Thr Arg
    2870              2875              2880
Val Pro Asp Pro Gln Glu Gly Thr Arg Gln Val Met Ser Met Val
    2885              2890              2895
Ser Ser Trp Leu Trp Lys Glu Leu Gly Lys His Lys Arg Pro Arg
    2900              2905              2910
Val Cys Thr Lys Glu Glu Phe Ile Asn Lys Val Arg Ser Asn Ala
    2915              2920              2925
Ala Leu Gly Ala Ile Phe Glu Glu Lys Glu Trp Lys Thr Ala
    2930              2935              2940
Val Glu Ala Val Asn Asp Pro Arg Phe Trp Ala Leu Val Asp Lys
    2945              2950              2955
Glu Arg Glu His His Leu Arg Gly Glu Cys Gln Ser Cys Val Tyr
    2960              2965              2970
Asn Met Met Gly Lys Arg Glu Lys Lys Gln Gly Glu Phe Gly Lys
    2975              2980              2985
Ala Lys Gly Ser Arg Ala Ile Trp Tyr Met Trp Leu Gly Ala Arg
    2990              2995              3000
Phe Leu Glu Phe Glu Ala Leu Gly Phe Leu Asn Glu Asp His Trp
    3005              3010              3015
Met Gly Arg Glu Asn Ser Gly Gly Gly Val Glu Gly Leu Gly Leu
    3020              3025              3030
Gln Arg Leu Gly Tyr Val Leu Glu Glu Met Ser Arg Ile Pro Gly
    3035              3040              3045
Gly Arg Met Tyr Ala Asp Asp Thr Ala Gly Trp Asp Thr Arg Ile
    3050              3055              3060
Ser Arg Phe Asp Leu Glu Asn Glu Ala Leu Ile Thr Asn Gln Met
    3065              3070              3075
Glu Lys Gly His Arg Ala Leu Ala Leu Ala Ile Ile Lys Tyr Thr
    3080              3085              3090
Tyr Gln Asn Lys Val Val Lys Val Leu Arg Pro Ala Glu Lys Gly
    3095              3100              3105
Lys Thr Val Met Asp Ile Ile Ser Arg Gln Asp Gln Arg Gly Ser
    3110              3115              3120
Gly Gln Val Val Thr Tyr Ala Leu Asn Thr Phe Thr Asn Leu Val
    3125              3130              3135
Val Gln Leu Ile Arg Asn Met Glu Ala Glu Glu Val Leu Glu Met
    3140              3145              3150
Gln Asp Leu Trp Leu Leu Arg Arg Ser Glu Lys Val Thr Asn Trp
    3155              3160              3165
Leu Gln Ser Asn Gly Trp Asp Arg Leu Lys Arg Met Ala Val Ser
    3170              3175              3180
```

```
Gly Asp Asp Cys Val Val Lys Pro Ile Asp Arg Phe Ala His
    3185            3190            3195

Ala Leu Arg Phe Leu Asn Asp Met Gly Lys Val Arg Lys Asp Thr
    3200            3205            3210

Gln Glu Trp Lys Pro Ser Thr Gly Trp Asp Asn Trp Glu Glu Val
    3215            3220            3225

Pro Phe Cys Ser His His Phe Asn Lys Leu His Leu Lys Asp Gly
    3230            3235            3240

Arg Ser Ile Val Val Pro Cys Arg His Gln Asp Glu Leu Ile Gly
    3245            3250            3255

Arg Ala Arg Val Ser Pro Gly Ala Gly Trp Ser Ile Arg Glu Thr
    3260            3265            3270

Ala Cys Leu Ala Lys Ser Tyr Ala Gln Met Trp Gln Leu Leu Tyr
    3275            3280            3285

Phe His Arg Arg Asp Leu Arg Leu Met Ala Asn Ala Ile Cys Ser
    3290            3295            3300

Ser Val Pro Val Asp Trp Val Pro Thr Gly Arg Thr Thr Trp Ser
    3305            3310            3315

Ile His Gly Lys Gly Glu Trp Met Thr Thr Glu Asp Met Leu Val
    3320            3325            3330

Val Trp Asn Arg Val Trp Ile Glu Glu Asn Asp His Met Glu Asp
    3335            3340            3345

Lys Thr Pro Val Thr Lys Trp Thr Asp Ile Pro Tyr Leu Gly Lys
    3350            3355            3360

Arg Glu Asp Leu Trp Cys Gly Ser Leu Ile Gly His Arg Pro Arg
    3365            3370            3375

Thr Thr Trp Ala Glu Asn Ile Lys Asn Thr Val Asn Met Met Arg
    3380            3385            3390

Arg Ile Ile Gly Asp Glu Glu Lys Tyr Val Asp Tyr Leu Ser Thr
    3395            3400            3405

Gln Val Arg Tyr Leu Gly Glu Glu Gly Ser Thr Pro Gly Val Leu
    3410            3415            3420
```

CDNA CLONE-LAUNCHED PLATFORM FOR HIGH-YIELD PRODUCTION OF INACTIVATED ZIKA VIRUS

RELATED APPLICATIONS

This application claims priority to U.S. Provisional Application No. 62/459,367 filed on Feb. 15, 2017, the contents of which are incorporated by reference in their entirety herein.

STATEMENT REGARDING FEDERALLY SPONSORED RESEARCH OR DEVELOPMENT

The invention was funded by NIH grant R01AI087856, Pan American Health Organization grant SCON2016-01353, and NIH grant AI120942.

SEQUENCE LISTING

This application includes a sequence listing which has been submitted via EFS-Web in a file named "4956101205.txt" created Jun. 6, 2018 and having a size of 85,243 bytes, which is hereby incorporated by reference in its entirety.

FIELD OF THE INVENTION

The invention generally relates to the development of variant Zika virus (ZIKV) strains, variant Zika genomes (cDNA clones) and Zika RNA transcripts that contain specific substitution mutations, and methods for producing high yields of ZIKV using these variant cDNA clones, RNA transcripts and Zika strains. These variant cDNA clones, RNA transcripts and Zika strains can be used for the manufacture of purified inactivated vaccines (NV), which may be useful for treating ZIKV related diseases and providing immunoprotection against ZIKV.

BACKGROUND OF THE INVENTION

Zika virus (ZIKV) has recently caused explosive outbreaks in the Americas and is unexpectedly associated with congenital microcephaly and other fetal abnormalities as well as Guillain Barrê syndrome (Schuler-Faccini et al., 2016). ZIKV was first isolated from a sentinel rhesus macaque in 1947 in the Zika Forest of Uganda (Dick et al., 1952). Human ZIKV infections have only sporadically been detected for decades. However, since 2007, ZIKV has rapidly spread across islands in the South Pacific and into the Americas, causing the outbreak on Yap Island in Micronesia, a subsequent outbreak in French Polynesia, and explosive, widespread epidemics in the Americas (Petersen et al., 2016). The World Health organization (http://www.who.int/emergencies/zika-virus/situation-report/6-october-2016/en/) has reported over 73 countries and territories with active ZIKV outbreaks/epidemics. Despite urgent medical needs, neither clinically approved vaccine nor antiviral is available for prevention and treatment.

ZIKV is a mosquito-borne member from the genus flavivirus within the family Flaviviridae. Besides ZIKV, many other flaviviruses are significant human pathogens, including the four serotypes of dengue (DENV-1 to -4), yellow fever (YFV), West Nile (WNV), Japanese encephalitis (JEV), and tick-borne encephalitis (TBEV) viruses. Flaviviruses have a positive-sense single-stranded RNA genome approximately 11,000 nucleotides in length. The genome contains a 5' untranslated region (UTR), single open-reading frame (ORF), and 3' UTR. The ORF encodes three structural (capsid [C], precursor membrane [prM], and envelope [E]) and seven non-structural (NS1, NS2A, NS2B, NS3, NS4A, NS4B, and NS5) proteins. The structural proteins form virus particles and function in virus entry into cells. The nonstructural proteins participate in viral replication, virion assembly, and evasion of host innate immune responses (Lindenbach, 2013). Like other flaviviruses, ZIKV enters cells through the receptor-mediated endocytosis. After low pH-induced fusion with the endosome membrane, flaviviruses release and translate their genomic RNA in the endoplasmic reticulum (ER). Viral RNA replication occurs in the virus-induced replication complexes formed in the ER membrane. Progeny viruses form on the ER-derived membrane as immature virus particles, in which prM/E heterodimers form trimeric spikes with icosahedral symmetry. After removal of the pr from the prM by host furin protease during the transit through the Golgi network, the immature, non-infectious virions become mature infectious viruses. Finally, progeny virions are released through an exocytosis pathway (Lindenbach, 2013). Rapid progress has been made on ZIKV research in the past two years, including the high-resolution structures of virus (Kostyuchenko et al., 2016; Sirohi et al., 2016), reverse genetic systems (Atieh et al., 2016; Schwarz et al., 2016; Shan et al., 2016b; Tsetsarkin et al., 2016; Weger-Lucarelli et al., 2017; Xie et al., 2016), animal models (Lazear et al., 2016; Rossi et al., 2016), and vaccine development (Abbink et al., 2016; Dowd et al., 2016; Larocca et al., 2016).

Development of an effective and affordable ZIKV vaccine is a public health priority. Multiple strategies have been taken, including DNA- or viral vector-expressing subunit, chimeric, and live-attenuated vaccines (Dawes et al., 2016). Three frontrunner candidates, including two DNA vaccines expressing viral structural proteins prM and E (Dowd et al., 2016; Larocca et al., 2016) and one purified inactivated ZIKV vaccine (PIV) based on Puerto Rico strain PRV-ABC59 (Abbink et al., 2016), protect monkeys from ZIKV challenge. These frontrunners are currently in phase I clinical trials.

The present invention addresses the need for technologies that can increase the yield of virus production to improve accessibility of inactivated vaccines and reduce costs without compromising vaccine immunogenicity.

BRIEF SUMMARY OF THE INVENTION

The invention in general relates to variant Zika virus (ZIKV) cDNA clones, RNA transcripts of these cDNA clones, and variant ZIKV strains which have been mutated to introduce at least one substitution mutation in at least one of the encoded ZIKV proteins, wherein said at least one substitution mutation comprises one or more of the following: NS1 K265E, prM H83R and NS3 S356F.

In some exemplary embodiments the cDNA clone, RNA transcript, or strain will comprise an NS1 K265E substitution mutation.

In some exemplary embodiments the encoded ZIKV proteins in the variant Zika virus (ZIKV) cDNA clone, RNA transcript of the cDNA clone, or variant ZIKV strain will comprise one of the following combinations of substitution mutations: (a) NS1 K265E, prM H83R and NS3 S356F; (b) NS1 K265E and prM H83R; or (c) NS1 K265E and NS3 S356F.

In some exemplary embodiments the encoded ZIKV proteins in the variant Zika virus (ZIKV) cDNA clone, RNA transcript of the cDNA clone, or variant ZIKV strain comprising any of the afore-mentioned substitutions may further comprise one or more other substitution mutations such as prM H83R, NS3 S356F, E R283W, E H219L, E L441L, E K443N, E T315I, E H401Y, E A501T, NS1 R103K and NS1 W98L.

In some embodiments the variant Zika virus (ZIKV) cDNA clone, RNA transcript of the cDNA clone, or variant ZIKV strain comprising any of the afore-mentioned substitutions may comprise a variant of one of the following: a cDNA clone of a North or South American ZIKV strain, an RNA transcript of the cDNA clone of a North or South American ZIKV strain, or a North or South American ZIKV strain.

In some embodiments the variant Zika virus (ZIKV) cDNA clone, RNA transcript of the cDNA clone, or variant ZIKV strain may comprise a variant of one of the following:

a cDNA clone of a strain selected from the group consisting of MR766-NIID, P6-740, ArD7117, IbH_30656, ArB1362, ARB13565, ARB7701, ARB15076, ArD_41519, ArD128000, ArD158084, ArD157995, FSM, FSS13025, PHL/2012/CPC-0740-Asian, H/PF/2013, PLCal_ZV, Haiti/1225/2014, SV0127_14 Asian, Natal_RGN_Asian, Brazil_ZKV2015 Asian, ZikaSPH2015, BeH815744, BeH819015, BeH819966, BeH823339, BeH828305, SSABR1-Asian, FLR, 103344, 8375, PRVABC59, Z1106033, MRS_OPY_Martinique, VE_Ganxian_Asian, GD01_Asian, GDZ16001, ZJO3, Rio-U1 and Rio-S1;

an RNA transcript of the cDNA clone of a strain selected from the group consisting of MR766-NIID, P6-740, ArD7117, IbH_30656, ArB1362, ARB13565, ARB7701, ARB15076, ArD_41519, ArD128000, ArD158084, ArD157995, FSM, FSS13025, PHL/2012/CPC-0740-Asian, H/PF/2013, PLCal_ZV, Haiti/1225/2014, SV0127_14_Asian, Natal_RGN_Asian, Brazil_ZKV2015_Asian, ZikaSPH2015, BeH815744, BeH819015, BeH819966, BeH823339, BeH828305, SSABR1-Asian, FLR, 103344, 8375, PRVABC59, Z1106033, MRS_OPY_Martinique, VE_Ganxian_Asian, GD01_Asian, GDZ16001, ZJO3, Rio-U1 and Rio-S1; or a strain selected from the group consisting of MR766-NIID, P6-740, ArD7117, IbH_30656, ArB1362, ARB13565, ARB7701, ARB15076, ArD_41519, ArD128000, ArD158084, ArD157995, FSM, FSS13025, PHL/2012/CPC-0740-Asian, H/PF/2013, PLCal_ZV, Haiti/1225/2014, SV0127_14_Asian, Natal_RGN_Asian, Brazil_ZKV2015_Asian, ZikaSPH2015, BeH815744, BeH819015, BeH819966, BeH823339, BeH828305, SSABR1-Asian, FLR, 103344, 8375, PRVABC59, Z1106033, MRS_OPY_Martinique, VE_Ganxian_Asian, GD01_Asian, GDZ16001, ZJO3, Rio-U1 and Rio-S1.

In some exemplary embodiments the variant Zika virus (ZIKV) cDNA clone, RNA transcript of the cDNA clone, or variant ZIKV strain comprising any of the afore-mentioned substitutions will comprise a variant of PRVABC59 or FSS13025.

In some exemplary embodiments the variant Zika virus (ZIKV) cDNA clone, RNA transcript of the cDNA clone, or variant ZIKV strain comprising any of the afore-mentioned substitutions may provide for increased yield of ZIKV production in cells as compared to the corresponding wildtype ZIKV cDNA clone, RNA transcript, or strain lacking these substitution mutations; and/or may provide for enhanced ZIKV assembly as compared to a corresponding wildtype ZIKV cDNA clone, RNA transcript, or strain lacking these substitution mutations, e.g., wherein the cells used to produce said variant ZIKV may be selected from any one of the following types of cells: (i) eukaryotic cells; (ii) mammalian cells; (iii) mouse or human cells; (iv) Vero cells, Huh7 cells, LLC-MK-2 cells, Hep-2 cells, LF 1043 (HEL) cells, MRC-5 cells, WI-38 cells, tMK cells, 293 T cells, QT 6 cells, QT 35 cells, or chicken embryo fibroblasts (CEF); and (v) Vero cells or Huh7 cells.

In some exemplary embodiments the variant Zika virus (ZIKV) cDNA clone, RNA transcript of the cDNA clone, or variant ZIKV strain comprising any of the afore-mentioned substitutions will comprise an infectious cDNA clone, RNA transcript, or strain.

In some exemplary embodiments the variant Zika virus (ZIKV) cDNA clone, RNA transcript of the cDNA clone, or variant ZIKV strain comprising any of the afore-mentioned substitutions will be further modified to include at least one additional mutation which results in a substitution, addition or deletion mutation in at least one Zika protein, preferably NS1, NS3 or prm, wherein said additional modification does not adversely impact the efficacy of the resultant cDNA clone, RNA transcript, or strain for use in vaccines.

In some exemplary embodiments the invention provides methods for producing ZIKV variants for use in vaccine manufacture, such methods in general comprising producing additional copies of any of the afore-mentioned variant Zika virus (ZIKV) cDNA clone, RNA transcript of the cDNA clone, or variant ZIKV strain comprising any of the afore-mentioned substitutions in a suitable system thereby obtaining additional ZIKV variants suitable for use in the manufacture of ZIKV vaccines. In preferred exemplary embodiments the suitable system will comprise producing the ZIKV variants in suitable cells, e.g., cells selected from one of the following groups: (i) eukaryotic cells; (ii) mammalian cells; (iii) mouse or human cells; (iv) Vero cells, Huh7 cells, LLC-MK-2 cells, Hep-2 cells, LF 1043 (HEL) cells, MRC-5 cells, WI-38 cells, tMK cells, 293 T cells, QT 6 cells, QT 35 cells, or chicken embryo fibroblasts (CEF); and (v) Vero cells or Huh7 cells, optionally wherein the produced ZIKV variants are attenuated or inactivated.

In some exemplary embodiments the invention provides a variant ZIKV cDNA clone, RNA transcript of the cDNA clone, or variant ZIKV strain comprising a substitution mutation corresponding to A3282G in the ZIKV genome, wherein the A3282G substitution results in a K265E substitution in the NS1 protein expressed from the cDNA clone, RNA transcript or strain.

In some exemplary embodiments the invention provides immunogenic compositions comprising a variant ZIKV strain containing any of the afore-mentioned substitutions and at least one pharmaceutically acceptable carrier or excipient, optionally wherein the strain is attenuated or inactivated, and further optionally which is suitable for parenteral or enteral administration.

In some exemplary embodiments the invention provides methods for eliciting an immune response in a subject in need thereof by administering a composition comprising a prophylactically or therapeutically effective amount of a variant ZIKV strain containing any of the afore-mentioned substitutions, or an immunogenic composition containing same as above-described, wherein the ZIKV strain is attenuated or inactivated. In some exemplary embodiments the immune response elicited may include one or more of the following: (i) a CD8$^+$ T cell response, an antibody response, and/or a cellular immune response against ZIKV; (ii) a neutralizing antibody titer equivalent to that of wildtype ZIKV infection; (iii) prevention of congenital ZIKV syndrome and/or microcephaly; and/or (iv) prevention of viremia in a subject after subsequent challenge with a wildtype ZIKV strain, optionally a human subject, further optionally a pregnant female.

BRIEF DESCRIPTION OF THE DRAWINGS

FIG. 1A-G contains identification and characterization of NS1 K265E mutant ZIKV strain FSS13025. (A) Plaque morphologies after plaque purification. Plaques were developed on day 4 post-infection. (B) Sequence comparison of the isolates S1-6 with parental ZIKV strain FSS13025 (GenBank number KU955593.1). The nucleotide acid and amino acid changes in associated ZIKV proteins are shown. The NS1 K265E mutation is shadowed in gray. (C) cDNA sequence chromatogram of positions 3280 to 3287 in ZIKV. The A3283G mutation is highlighted. (D) Examination of E protein expression by immunofluorescence analysis (IFA). Vero cells were electroporated with in vitro-transcribed genome-length ZIKV FSS13025 (WT or K265E mutant) RNA. Intracellular E protein expression was monitored by IFA using 4G2 antibody. (E) Plaque morphologies of recombinant WT or NS1 K265E ZIKV strain FSS13025. Plaques were developed on day 4 post-infection. (F) RNA copy/PFU ratios at 72 h post-transfection. (G) Virus yields post-transfection. The extracellular virions were determined by plaque assay. Each data represents the average and standard deviation from triplicates. The multiple t test was applied to examine the statistical significance between K265E and WT at indicated time points. *p<0.05, significant; *p<0.01, very significant; ***p<0.001, extremely significant.

FIG. 3A-F contains characterization of NS1 K265E in ZIKV strain PRVABC59. (A) Construction of the infectious clone of ZIKV strain PRVABC59. Six RT-PCR products (indicated as fragments A to G) were assembled to cover the complete cDNA of ZIKV genome. A T7 promoter and a hepatitis delta virus ribozyme (HDVr) sequence were engineered at the 5' and 3' end of the viral cDNA, respectively. Restriction enzyme sites and their nucleotide positions in ZIKV genome are indicated. (B) Sequence comparison of recombinant and parental ZIKV strain PRVABC59. (C) IFA of Vero cells transfected with in vitro transcribed WT or NS1 K265E mutant genome-length RNAs of ZIKV strain PRVABC59. (D) Plaque morphologies of recombinant WT or NS1 K265E ZIKV-PRV. Plaques were developed after 4 days of infection. (E) Virus yields from WT or NS1 K265E ZIKV-PRV RNA-transfected cells post-transfection. Virus titers were determined by plaque assay. (F) Growth kinetics of WT and NS1 K265E ZIKV-PRV on Vero cells. Cells were infected with WT and NS1 K265E mutant ZIKV-PRV (MOI 0.01). The multiple t test was performed to analyze the statistical significance at each time point.

FIG. 4A-F shows effects of NS1 K265E mutation on ZIKV life cycle. (A) Replicon transient transfection assay. The top panel shows the schematic diagram of ZIKV replicon with Renilla luciferase reporter. Luciferase signals of transfected cells were normalized to those of non-transfected cells. Each data point represents the average and standard deviation from three independent experiments. (B) Flowchart of monitoring single cycle of ZIKV infection. After 1-hour infection, virus inoculums were removed and cells were washed three times with PBS. To quantify intracellular viral RNAs at 1, 14 and 20 h post-infection, cells were further stringently washed. Intracellular viral RNAs were measured by qRT-PCR and normalized using the cellular GAPDH RNA levels. Extracellular viral RNA were determined by qRT-PCR; and extracellular/intracellular infectivity were quantified by plaque assay. (C) Intracellular/extracellular RNA and infectivity obtained from (B). Each data point represents the average and standard deviations of three independent experiments. The multiple t test was applied to analyze the statistical significances. (D) Flowchart of examining virus attachment and entry. At given time points, intracellular viral RNAs and GAPDH RNAs were quantified by qRT-PCR accordingly. (E) Intracellular viral RNAs quantified from (D). The relative viral RNA levels were calculated by normalizing the viral RNAs at each time point to that of 1 h post-infection (set at 100%). Each data point represents the averaged relative RNA of three independent experiments. The multiple t test was applied to analyze the statistical significances. (F) Carton of K265E mutation's effect on virus life cycle.

FIG. 5A-G illustrates co-immunoprecipitation assays (Co-IP). (A) Location of residue K265 in the 3D crystal structure of ZIKV NS1. (B) Flowchart of Co-IP experiments from ZIKV infected cells. Rabbit IgG anti-NS1 or control IgGs were used for pull down ZIKV NS1 and its associated complexes. (C) Co-IP results from (B). NS1 in both eluates and cell lysates were probed using rabbit anti-NS1 and protein A-HRP. E proteins were detected by mouse IgG anti-ZIKV and goat anti-mouse IgG-HRP. prM was examined by rabbit IgG anti-ZIKV prM and goat anti-rabbit IgG-HRP. (D) Densitometry analysis of Western blot results from (C). The band intensities of prM and E proteins in (C) were quantified and normalized to those of NS1 proteins from corresponding eluates. The efficiencies of prM and E pulled-down by WT NS1 were set as 100%. The averaged relative intensities from three independent experiments were shown. An unpaired Student t test was used to estimate the statistical significance. (E) Flowchart of Co-IP from HEK293T cells transiently expressing NS1 and NS2A-HA. Cell lysates was subjected to Co-IP using mouse IgG anti-HA or mouse control IgG. (F) Western blot results from (E). NS2A-HA in the eluates and cell lysates were examined by rabbit IgG anti-HA and goat anti-rabbit IgG-HRP respectively. NS1 proteins were detected by rabbit anti-ZIKV NS1 and goat anti-rabbit IgG-HRP. (G) Densitometry analysis of Western blot results from (F). The band intensities of NS1 proteins in (F) were quantified and normalized to those of NS2A-HA proteins from corresponding eluates. An unpaired Student t test was used to evaluate the statistical significance.

FIG. 9A-C shows a stability analysis of 3'UTR deletion ZIKVs in cell culture. P0 viruses (derived from the culture fluids of RNA-transfected) were continuously cultured on Vero cells for five rounds (5 days for each round of culture), resulting in P5 viruses. The P5 viruses were subjected to the following characterization. (A) Immunostaining focus assay. WT and P5 mutant viruses were analyzed using an immunostaining focus assay on Vero cells. For each mutant virus, three independent selections were performed on Vero cells. Representative images of infectious foci for each P5 mutant virus are presented. (B) Replication kinetics. Vero cells in 24-well plates ($2*10^5$ cells per well) were infected with WT and P5 mutant viruses at an MOI of 0.01. Culture fluids were quantified for infectious viruses on days 1 to 5 using the immunostaining focus assay on Vero cells. (C) Adaptive mutations in P5 mutant viruses. The complete genomes of P5 mutant viruses were sequenced for each of the three independent selections. The adaptive mutations are indicated by their amino acid positions of indicated genes based ZIKV FSS13025 strain (GenBank number KU955593.1).

DETAILED DESCRIPTION OF THE INVENTION

Figure 2A:
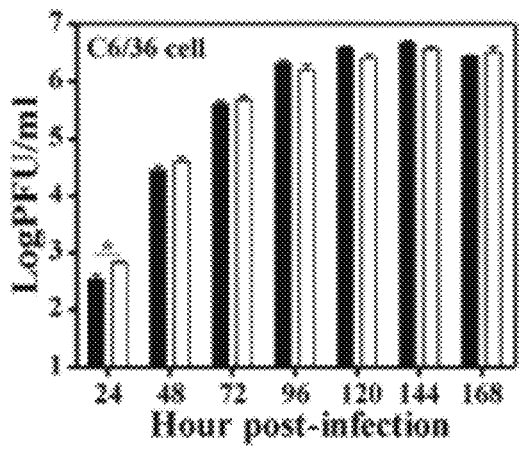
FIG. 2A-D contains comparisons of growth kinetics of NS1 K265E mutant and WT ZIKV strain FSS13025 on four different cell lines. (A) C6/36 cells. (B) BHK-21 cells. (C) Vero cells. (D) Huh7 cells. Each data represents the average and standard deviation from two independent experiments performed in triplicates. The multiple t test was performed to analyze the statistical significance at each time point. Only significant differences are shown.

The present invention in general relates to the construction and characterization of variant Zika strains having advantageous properties and the use and manufacture thereof, especially in making immunogenic compositions for use in providing immunity against Zika. However, before further describing the invention in detail the following definitions are provided.

Definitions

An "adjuvant" refers to a substance that enhances an immune response, e.g., an antibody or cell-mediated immune response against a specific agent, e.g., an antigen, or an infectious agent.

An "attenuated" or "live-attenuated" virus strain refers to a mutated, modified and/or recombinant virus having reduced or no virulence or propensity to cause a disease or infection normally associated with the wildtype or unmodified, non-mutated virus.

Complementary DNA ("cDNA") is DNA that is complementary to a given RNA which serves as a template for synthesis of the cDNA in a reaction that is catalyzed by reverse transcriptase. cDNA is synthesized from a single stranded RNA and may be artificially produced or naturally produced by retroviruses.

A viral "cDNA clone" is a double-stranded DNA copy of all or a portion of a viral genome, in this case the ZIKV RNA genome. A cDNA clone is generally carried in a plasmid vector. An "infectious cDNA clone" can be used for production of in vitro RNA transcripts with a polymerase such as the T7 RNA polymerase. An infectious cDNA clone (or the RNA transcript produced from the infectious cDNA clone) generates recombinant cDNA clone-derived virus when transfected into cells.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter. The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

In general, "identity" or "sequence identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, introducing gaps if necessary to achieve the maximum percent identity, counting the exact number of matches between the two aligned sequences, dividing by the length of the reference sequence, and multiplying the result by 100. The determination of percent identity between any two sequences can be accomplished using a mathematical algorithm. Alignment for purposes of determining percent sequence identity can be achieved in various ways that are within the skill in the art, for instance, using publicly available computer software such as BLAST, BLAST-2, BLASTN, BLASTP, ALIGN, ALIGN-2 or Megalign (DNASTAR) software. Appropriate parameters for measuring alignment, including any algorithms needed to achieve maximal alignment over the full-length of the sequences being compared can be determined by known methods. Depending on the application, the "percent identity" can exist over a region of the sequence being compared, e.g., over the ORF of the variant ZIKV cDNA clone, RNA transcript, or strain, or, alternatively, exist over the full length of the two sequences to be compared. A skilled artisan would understand that for purposes of determining sequence identity when comparing a DNA to an RNA sequence, a thymidine nucleotide is equivalent to a uracil nucleotide.

An "immunogenic composition" herein refers to a composition containing an attenuated or inactivated ZIKV strain according to the invention which elicits an immune response in a susceptible host, e.g., an antibody, Th1 or cellular (e.g., T cell-mediated) immune response.

An "isolated" biological component (such as an isolated virus, bacterium or nucleic acid) refers to a component that has been substantially separated or purified away from its environment or other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "nucleic acid" and "polynucleotide" refer to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism. The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

A "pharmaceutically acceptable carrier" or "excipient" refers to compounds or materials conventionally used in immunogenic or vaccine compositions during formulation and/or to permit storage.

"Prophylactically effective amount" of a ZIKV strain according to the invention refers to an amount sufficient to prevent or reduce the incidence of infection in a susceptible host.

The term "recombinant" as used herein to describe a nucleic acid molecule means a polynucleotide of genomic, cDNA, viral, semisynthetic, or synthetic origin which does not occur in nature or by virtue of its origin or manipulation is associated with or linked to another polynucleotide in an arrangement not found in nature. The term "recombinant" as used with respect to a protein or polypeptide means a polypeptide produced by expression of a recombinant polynucleotide.

A "susceptible host" herein refers to a host or animal that may be infected by ZIKV. Such hosts include humans or animals, e.g., a human, nonhuman primate, ape, monkey, horse, cow, carabao, goat, duck, bat, or other suitable non-human host.

"Therapeutically effective amount" of a ZIKV strain according to the invention refers to an amount sufficient to treat ZIKV infection or a disease associated therewith in a susceptible host.

A "vaccine" composition herein refers to a composition containing a ZIKV strain according to the invention which elicits a therapeutic or prophylactic immune response against ZIKV.

The terms "variant" and "mutant" refer to biologically active derivatives of the reference molecule that retain or enhance the desired activity, such as the ability to increase ZIKV replication and production as discussed herein. In the present invention, a variant ZIKV cDNA clone or strain contains one or more naturally occurring or genetically engineered mutations that result in high-yield manufacture of ZIKV in cells, particularly monkey or human cell lines, such as Vero or Huh7 cells.

The terms "variant" and "mutant" in reference to a polynucleotide (e.g. the variant ZIKV cDNA clone, RNA transcript, strain, or ORF) or polypeptide (e.g., one of the three structural (capsid [C], precursor membrane [prM], and envelope [E]) or seven non-structural (NS1, NS2A, NS2B, NS3, NS4A, NS4B, and NS5) proteins of the ZIKAV) refers to a polynucleotide or polypeptide that differs from the corresponding wildtype polynucleotide sequence and structure by one or more nucleic acid additions, substitutions and/or deletions, or differs from the corresponding wildtype polypeptide sequence and structure by one or more amino acid additions, substitutions and/or deletions, so long as the modifications do not destroy the desired biological activity (e.g. the ability to replicate). In general, the sequences of such variants and mutants of the invention will have a high degree of sequence identity to the reference or corresponding wildtype sequence, e.g., a nucleic acid or amino acid sequence identity of at least 40, 50, 60, 70, 80 or 85%, more particularly at least 86, 87, 88, 89, 90, 91, 92, 93, 94, 95, 96, 97, 98 or 99%, when the two sequences are aligned. For example, the nucleic acid sequence of the open reading frame (ORF) of a ZIKV cDNA clone, RNA transcript, or strain that is a variant of the PRVABC59 strain will generally have at least 40, 50, 60, 70, 80 or 85%, more particularly at least 86, 87, 88, 89, 90, 91, 92, 93, 94, 95, 96, 97, 98 or 99% sequence identity to the nucleic acid sequence of the ORF of PRVABC59.

Often, the "variant" or "mutant" polypeptide sequence will include the same number of amino acids as the wildtype polypeptide but will include particular substitutions, as explained herein.

It will be appreciated by those of ordinary skill in the art that, as a result of the degeneracy of the genetic code, there are many nucleotide sequences that encode a particular polypeptide of interest as described herein. Some of these polynucleotides bear minimal homology to the nucleotide sequence of any native gene. Nonetheless, "variant" or "mutant" polynucleotides that vary due to differences in codon usage are specifically contemplated by the present invention.

The "variant" or "mutant" polypeptide sequence can include amino acid substitutions that are conservative in nature, i.e., those substitutions that take place within a family of amino acids that are related in their side chains. Specifically, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cysteine, serine, threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. Further one of skill in the art may readily determine regions of the molecule of interest that can tolerate change by reference to Hopp/Woods and Kyte-Doolittle plots, well known in the art.

"ZIKV infection" or "infection elicted by ZIKV" herein refers to the infection of a susceptible host with ZIKV and diseases associated therewith, including congenital ZIKV syndrome and Guillan-Barrē syndrome (GB S).

As has been mentioned above the present invention provides novel Zika variant strains for potential use in making Zika vaccines. In general the invention relates to the construction and characterization of a DNA copy of the Zika virus (ZIKV) genome (a cDNA clone) or a ZIKV strain encoding ZIKA proteins having specific mutations or combinations thereof, e.g., mutations in the NS1, NS3, prM and/or E proteins. These variant ZIKV cDNA clones, RNA transcripts of the cDNA clones, or variant ZIKV strains encoding the mutations, may possess increased ZIKV replication in cells, and thus can be used to produce higher yields of ZIKV, with shortened manufacture time, and minimized chance of contamination as compared to methods using existing ZIKV cDNA clones, RNA transcripts and strains that do not include these mutations. The ZIKV produced using the subject variant cDNA clones, RNA transcripts or strains may be used to produce ZIKV vaccines, in particular inactivated ZIKV vaccines, for treating diseases related to ZIKV or providing immunoprotection against infections elicited by ZIKV, including congenital ZIKV syndrome, microcephaly, and Guillan-Barrē syndrome (GBS). The vaccine may also prevent viremia in pregnant women and travelers to epidemic/endemic regions, avert congenital ZIKV syndrome and/or may also be useful to suppress epidemic transmission.

The variant ZIKV cDNA clones, RNA transcripts or strains of the invention contain one or more mutations in the ZIKV open reading frame (ORF). These mutations in particular may include the following amino acid substitutions: NS1 K265E, prM H83R, NS3 S356F, E R283W, E H219L, E L441L, E K443N, E T315I, E H401Y, E A501T, NS1 R103K, and NS1 W98L. In some preferred embodiments a variant ZIKV cDNA clone, RNA transcript thereof, or ZIKV strain according to the invention encodes ZIKV proteins comprising an NS1 K265E substitution; NS1 K265E, prM H83R and NS3 S356F substitutions; NS1 K265E and prM H83R substitutions; or NS1 K265E and NS3 S356F substitutions. It has been observed that the NS1 K265E mutation enhances the replication and viral yield of ZIKV in cells, but does not affect ZIKV virulence. In addition, both the prM H83R and the NS3 S356F mutations have been found to further increase viral yield, with the triple mutant (NS1 K265E, prM H83R and NS3 S356F) producing a peak viral titer.

The variant ZIKV cDNA clones, RNA transcripts and strains of the invention may comprise cDNA or RNA corresponding to the complete (full-length) or less than the complete ZIKV genomic RNA, such as one or several fragments of the ZIKV genome. In addition they may be derived from different Zika strains other than those embodied herein, e.g., using Zika strains which are known and available in the art, i.e., by introducing the afore-mentioned substitution mutations or corresponding mutations in the ORF of these or other Zika strains. Generally, the ZIKV cDNA clones, RNA transcripts and strains will comprise sequences encoding all or substantially all the proteins of a ZIKV or will comprise the entire open reading frame (ORF) of a ZIKV genome (modified to include any or all of the afore-mentioned substitution mutations). In some embodiments, the sequences will have at least 40, 50, 60, 70, 80 or 85%, more particularly at least 86, 87, 88, 89, 90, 91, 92, 93, 94, 95, 96, 97, 98 or 99%, sequence identity to a wildtype sequence of ZIKV. In a preferred embodiment, a cDNA clone, RNA transcript or strain containing any combination of the afore-identified substitution mutations can be transfected into cells or used to infect cells to produce Zika virus containing any combination of the afore-identified substitution mutations. In certain embodiments the produced virus may be an infectious, attenuated, replication defective or inactivated virus containing any combination of the afore-identified substitution mutations.

The variant ZIKV cDNA clones, RNA transcripts and strains of the invention may be derived from any ZIKV and thus may be variants of any strain of ZIKV. For example, the source of the variant ZIKV cDNA clone or strain can be any one of the following strains: MR766-NIID, P6-740, ArD7117, IbH_30656, ArB1362, ARB13565, ARB7701, ARB15076, ArD_41519, ArD128000, ArD158084, ArD157995, FSM, FSS13025, PHL/2012/CPC-0740-Asian, H/PF/2013, PLCal_ZV, Haiti/1225/2014, SV0127_14_Asian, Natal_RGN_Asian, Brazil_ZKV2015_Asian, ZikaSPH2015, BeH815744, BeH819015, BeH819966, BeH823339, BeH828305, SSABR1-Asian, FLR, 103344, 8375, PRVABC59, Z1106033, MRS_OPY_Martinique, VE_Ganxian_Asian, GD01_Asian, GDZ16001, ZJO3, Rio-U1 or Rio-S1 ZIKV strains (see Wang L, et al. Cell Host Microbe. 2016 May 11; 19(5):561-5). In certain embodiments, the strain is a North American strain or a South American strain. Preferred ZIKV strains used to produce Zika variant according to the invention are PRVABC59 or FSS13025.

In some embodiments, the variant ZIKV cDNA clone is contained in a plasmid, which optionally comprises a promoter and/or a ribozyme sequence. For example the promoter may comprise a viral promoter or a mammalian promoter. The promoter can be at the 5' end of the cDNA clone, and is optionally a T7 promoter or a cytomegalovirus (CMV) promoter. The ribozyme sequence can be at the 3' end of the cDNA clone, and is optionally a hepatitis delta virus ribozyme (HDVr) sequence. In some embodiments, the plasmid is an expression vector, optionally a mammalian expression vector.

The ZIKV cDNA clones and strains of the present invention, and plasmids or vectors encoding the same, may be further modified, engineered, optimized, or appended in order to provide or select for further increased yield and/or other various features. In particular, other mutations (e.g. missense, additions, substitutions, deletions, or combinations thereof) may be introduced into the cDNA clones or strains in any one or more of the genes encoding the C, prM, E, NS1, NS2A, NS2B, NS3, NS4A, NS4B, or NS5 proteins. For example, a missense mutation may be introduced which results in a cold-sensitive mutation or a heat-sensitive mutation. In some embodiments, major phosphorylation sites of viral protein(s) may be removed.

In addition to mutations within the genes of the ORF, the intergenic region of the cDNA clone or strain may be altered. In one embodiment, the length of the intergenic region is altered. In another embodiment, the intergenic regions may be shuffled from the 5' to the 3' end of the cDNA clone or genome. In other embodiments, the genome position of a gene or genes of the cDNA clone or strain can be changed.

The variant ZIKV cDNA clone, RNA transcript or strain of the present invention may further comprise a sequence encoding one or several heterologous genes or other non-gene sequences that are not derived from the ZIKV which was used as a source for the variant ZIKV cDNA clone or strain. Any heterologous gene of interest can be inserted into the nucleic acids of the present invention. In certain embodiments the heterologous genes encode peptides or proteins which are recognized as an antigen from an infectious agent by the immune system of a mammal. The heterologous gene may thus encode at least one antigen suitable for inducing an immune response against an infectious agent, at least one molecule interfering with the replication of an infectious agent or an antibody providing protection against an infectious agent. Alternatively or additionally, the heterologous gene may encode an immune modulator, a cytokine, an immunoenhancer or an anti-inflammatory compound. The cDNA clones and strains may also contain other mutations including, but not limited to, replacing a ZIKV gene with the analogous gene of a virus of a different species, of a different subgroup, or of a different variant.

In certain embodiments, the variant ZIKV cDNA clone, RNA transcript or strain of the invention comprises additional mutations that result in an attenuated virus strain which is modified so that it has reduced or no virulence or propensity to cause any disease or infection normally associated with the wildtype or unmodified ZIKV. The cDNA clone or attenuated strain may in addition comprise deletions within the 3'UTR.

The enhanced replication phenotypes of a variant ZIKV cDNA clone or strain of the invention can be tested by any method known to the artisan. For example, cells can be transfected with a candidate variant ZIKV cDNA clone or RNA transcript thereof, or infected with the variant ZIKV strains. The replication rate of the ZIKV in cells can be determined by plotting the viral titer over the time post transfection or infection. The viral titer can be measured by any technique known to the skilled artisan. In certain embodiments, the yield of ZIKV production on cells can be measured using a one-step plaque-purification method. In certain embodiments, different cell lines can be used to evaluate the enhanced replication phenotype of the cDNA clone or strain. For example, the achievable virus titers may be different in different cell lines.

In a specific embodiment, the viral titre is determined by obtaining a sample from transfected or infected cells or an infected subject, preparing a serial dilution of the sample and infecting a monolayer of cells that are susceptible to infection with the virus at a dilution of the virus that allows for the emergence of single plaques. The plaques can then be counted and the viral titre expressed as plaque forming units per milliliter of sample. In another embodiment, the growth rate of a variant ZIKV strain of the invention in a subject can be estimated by the titer of antibodies against the virus in the subject. Without being bound by theory, the antibody titer in the subject reflects not only the viral titer in the subject but also the antigenicity. If the antigenicity of the virus is constant, the increase of the antibody titer in the subject can be used to determine the growth curve of the virus in the subject. In a preferred embodiment, the growth rate of the virus in animals or humans is tested by sampling biological fluids of a host at multiple time points post-infection and measuring viral titer.

The expression of ZIKV proteins from the variant ZIKV cDNA clone, RNA transcript thereof, or variant ZIKV strain in a cell culture system or in a subject can be determined by any technique known to the skilled artisan. In certain embodiments, expression is measured by quantifying the level of the transcript. The level of the transcript can be measured by Northern blot analysis or by RT-PCR using probes or primers, respectively that are specific for the transcript. The transcript can be distinguished from the genome of the virus because the virus is in the antisense orientation whereas the transcript is in the sense orientation. In certain embodiments, the expression of the gene is measured by quantifying the level of the protein product of the gene. The level of the protein can be measured by Western blot analysis using antibodies that are specific to the protein.

Additionally, the present invention provides methods of preparing a recombinant ZIKV, such as a viral RNA or a virion, using a variant ZIKV cDNA clone, RNA transcript of the cDNA, or strain of the invention by any method known to the artisan. For example, cells can be transfected with the cDNA clone or RNA transcript thereof, or infected with the strain, then grown in culture and monitored for viral protein expression, RNA synthesis, and virus production. Suitable host cells include any eukaryotic cells that support viral replication, for example monkey (e.g. Vero) or human (e.g. Huh7) cell lines as discussed herein. In some embodiments the cDNA can be expressed in a host cell and the ZIKV isolated from that host cell. Any of methods for isolating viruses from cell culture known in the art may be used. Alternatively, the nucleic acids of the present invention can be transcribed and/or translated using chemicals, biological reagents and/or cell extracts and the recombinant ZIKV subsequently isolated.

The recombinant virus produced from the variant ZIKV cDNA clone, RNA transcript of the cDNA, or strain of the invention can be attenuated, or can be inactivated by any known method, including with chemicals, heat or radiation. For example, common techniques known to one of skill in the art use formalin, beta-propiolactone, heat, and/or detergent for inactivation. An inactivated vaccine has a low residual infectivity following inactivation, e.g. <1 PFU/mL. The PFU's of a particular vaccine may be determined, for example, by using a plaque assay, an immunostaining assay, or other method known in the art for detecting viral infectivity. The virus can purified by any method known, including concentration by ultrafiltration followed by purification by zonal centrifugation or by chromatography, and may be purified before or after inactivation.

Inactivated vaccine types that can be used in the invention include whole-virus vaccines or subvirion (split) vaccines. The whole-virus vaccine contains intact, inactivated virus, while the subvirion vaccine contains purified virus disrupted with detergents that solubilize the lipid-containing viral envelope, followed by chemical inactivation of residual virus. Various assays, f or example sucrose gradients and neutralization assays, can be used to test the safety of a viral vaccine.

Inactivated or attenuated virus produced according to the invention can be used to confer prophylactic or therapeutic protection in susceptible hosts against ZIKV infection, e.g., to treat or prevent ZIKV infection and/or to prevent congenital ZIKV syndrome or GBS. The ZIKV vaccine produced according to the invention may be formulated using known techniques for formulating viral vaccines or immunogenic compositions of viral vaccines.

Administration

The immunogenic compositions of the present invention may be administered in a number of ways depending upon whether local or systemic treatment is desired.

For example, administration may be topical, parenteral, or enteral.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

The terms "oral", "enteral", "enterally", "orally", "non-parenteral", "non-parenterally", and the like, refer to administration of a compound or composition to an individual by a route or mode along the alimentary canal. Examples of "oral" routes of administration of a vaccine composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories for the lower intestinal tract of the alimentary canal.

Preferably, the formulated virus-containing composition is suitable for intranasal, injection, topical or oral administration, for example as a dried stabilized powder for reconstitution in a suitable buffer prior to administration or in an aerosol composition. In a preferred embodiment, the composition is intranasally administered.

Pharmaceutical compositions and formulations for topical administration may include transdermal patches, ointments, lotions, creams, gels, drops, suppositories, sprays, liquids, semisolids, monophasic compositions, multiphasic compositions (e.g., oil-in-water, water-in-oil), foams microsponges, liposomes, nanoemulsions, aerosol foams, polymers, fullerenes, and powders (see, e.g., Reference 35, Taglietti et al. (2008) Skin Ther. Lett. 13:6-8). Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal, or intraventricular administration may include sterile aqueous solutions that may also contain buffers, diluents and other suitable additives such as, but not limited to, penetration enhancers, carder compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, aerosols, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. Agents that enhance uptake of oligonucleotides at the cellular level may also be added to the pharmaceutical and other compositions of the present invention. For example, cationic lipids, such as lipofectin, cationic glycerol derivatives, and polycationic molecules, such as polylysine, also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

The compositions of the present invention may include excipients known in the art. Examples of excipients used for vaccine formulation such as adjuvants, stabilizers, preservatives, and trace products derived from vaccine manufacturing processes include but are not limited to: Aluminum Hydroxide, Amino Acids, Benzethonium Chloride, Formaldehyde or Formalin, Inorganic Salts and Sugars, Vitamins, Asparagine, Citric Acid, Lactose, Glycerin, Iron Ammonium Citrate, Magnesium Sulfate, Potassium Phosphate, Aluminum Phosphate, Ammonium Sulfate, Casamino Acid, Dimethyl-betacyclodextrin, 2-Phenoxyethanol, Bovine Extract, Polysorbate 80, Aluminum Potassium Sulfate, Gelatin, Sodium Phosphate, Thimerosal, Sucrose, Bovine Protein, Lactalbumin Hydrolysate, Formaldehyde or Formalin, Monkey Kidney Tissue, Neomycin, Polymyxin B, Yeast Protein, Aluminum Hydroxyphosphate Sulfate, Dextrose, Mineral Salts, Sodium Borate, Soy Peptone, MRC-5 Cellular Protein, Neomycin Sulfate, Phosphate Buffers, Polysorbate, Bovine Albumin or Serum, DNA, Potassium Aluminum Sulfate, Amorphous Aluminum Hydroxyphosphate Sulfate, Carbohydrates, L-histidine, Beta-Propiolactone, Calcium Chloride, Neomycin, Ovalbumin, Potassium Chloride, Potassium Phosphate, Sodium Phosphate, Sodium Taurodeoxycholate, Egg Protein, Gentamicin, Hydrocortisone, Octoxynol-10, α-Tocopheryl Hydrogen Succinate, Sodium Deoxycholate, Sodium Phosphate, Beta-Propiolactone, Polyoxyethylene 910, Nonyl Phenol (Triton N-101, Octoxynol 9), Octoxinol-9 (Triton X-100), Chick Kidney Cells, Egg Protein, Gentamicin Sulfate, Monosodium Glutamate, Sucrose Phosphate Glutamate Buffer Calf Serum Protein, Streptomycin, Mouse Serum Protein, Chick Embryo Fibroblasts, Human Albumin, Sorbitol, Sodium Phosphate Dibasic, Sodium Bicarbonate, Sorbitol, Sucrose, Potassium Phosphate Monobasic, Potassium Chloride, Potassium Phosphate Dibasic, Phenol, Phenol Red (Phenol sulfonphthalein), Amphotericin B, Chicken Protein, Chlortetracycline, Ethylenediamine-Tetraacetic Acid Sodium (EDTA), Potassium Glutamate, Cell Culture Media, Sodium Citrate, Sodium Phosphate Monobasic Monohydrate, Sodium Hydroxide, Calcium Carbonate, D-glucose, Dextran, Ferric (III) Nitrate, L-cystine, L-tyrosine, Magnesium Sulfate, Sodium Hydrogenocarbonate, Sodium Pyruvate, Xanthan, Peptone, Disodium Phosphate, Monosodium Phosphate, Polydimethylsilozone, Hexadecyltrimethylammonium Bromide Ascorbic Acid, Casein, Galactose, Magnesium Stearate, Mannitol, Hydrolyzed Porcine Gelatin, Freund's emulsified oil adjuvants (complete and incomplete), Arlacel A, Mineral oil, Emulsified peanut oil adjuvant (adjuvant 65), *Corynebacterium granulosum*-derived P40 component, Lipopolysaccharide, *Mycobacterium* and its components, Cholera toxin, Liposomes, Immunostimulating complexes (ISCOMs), Squalene, and Sodium Chloride.

The vaccine or immunogenic composition may be used in the vaccination of a mammalian host, particularly a human, nonhuman primate, ape, monkey, horse, cow, carabao, goat, duck, bat, or other suitable non-human host. In some instances the subject may be immunocompromised or may have another condition, e.g., may be pregnant.

The following examples are offered to illustrate, but not to limit, the claimed invention.

Examples

Materials and Methods

Cell Culture and Antibodies.

BHK-21 and Vero cells were purchased from the American Type Culture Collection (ATCC, Bethesda, Md.), and maintained in a high-glucose Dulbecco's modified Eagle's medium (DMEM) supplemented with 10% fetal bovine serum (FBS) (HyClone Laboratories, South Logan, Utah) and 1% penicillin/streptomycin at 37° C. with 5% $CO_2$. *A. albopictus* C6/36 cells were grown in RPMI1640 containing 10% FBS and 1% penicillin/streptomycin at 30° C. with 5% $CO_2$. Huh7 cells were maintained in a high-glucose Dulbecco's Modified Eagle Medium (DMEM) supplemented with 10% fetal bovine serum (FBS), 1% penicillin-streptomycin and 1% Non-Essential Amino Acids (NEAA) at 37° C. with 5% $CO_2$. HEK293T cells were grown in high-glucose DMEM containing 10% FBS and 1% penicillin/streptomycin. All culture medium, NEAA and antibiotics were purchased from ThermoFisher Scientific (Waltham, Mass.).

The following antibodies were used: a mouse monoclonal antibody (mAb) 4G2 cross-reactive with flavivirus E protein (ATCC); goat anti-mouse IgG conjugated with Alexa Fluor®488 (Thermo Fisher Scientific, Waltham, Mass.); goat anti-mouse or anti-rabbit IgGs conjugated with horseradish peroxidase (IgG-HRP), protein A conjugated with HRP (A-HRP; Sigma, St. Louis, Mo.); rabbit or mouse control IgGs (ThermoFisher Scientific); rabbit IgG against ZIKV NS1, mouse IgG anti-ZIKV E, rabbit IgG anti-ZIKV prM (Alpha Diagnostic Intl. Inc., San Antonio, Tex.); mouse anti-HA (Abcam, Cambridge, United Kingdom); and rabbit anti-HA (Sigma).

Plasmid Construction.

The NS1 K265E mutation was introduced into the ZIKV infectious clone pFLZIKV containing the cDNA sequence of Cambodian strain (FSS13025) (Shan et al., 2016b) through an overlap PCR approach. Briefly, a cDNA fragment flanked between restriction sites AvrII (positions 1532-1537 in ZIKV genome) and SphI (positions 3856-3861 in ZIKV genome) was amplified by overlap PCR. The A3282G (NS1 K265E) mutation was introduced into the overlap primers during primer synthesis. The overlap PCR product containing the A3282G mutation was digested with AvrII and SphI restriction enzymes and cloned into the pFLZIKV.

Prior to construction of the infectious clone of ZIKV strain PRVABC59 (ZIKV-PRV), the parental viruses were propagated on Vero cells for two passages and subjected to whole-genome sequencing. Specifically, viral RNA was extracted using QIAamp Viral RNA Kits (Qiagen, Hilden, Germany). cDNA fragments covering the complete genome were synthesized from genomic RNA using the SuperScript® III One-Step RT-PCR System with Platinum® Taq DNA Polymerase (Invitrogen) according to the manufacturer's instructions. Similar strategy as previously reported for making ZIKV FSS13025 infectious clone (Shan et al., 2016b) was used to construct the infectious clone of ZIKV-PRV. FIG. 3A depicts the scheme to clone and assemble the full genome of ZIKV-PRV. The genomic cDNA was assembled using a single-copy vector pCC1BAC (Epicentre, Madison, Wis.). *E. coli* strain TransforMax™ EPI300™ (Epicentre) was used to propagate the plasmids. The virus-specific sequence of each intermediate clone was validated by Sanger DNA sequencing before it was used in subsequent steps. The final plasmid containing full-length cDNA (pFL-ZIKV-PRV) was sequenced to ensure no undesired mutations. A T7 promoter and a hepatitis delta virus ribozyme (HDVr) sequence were engineered at the 5' and 3' ends of the complete viral cDNA for in vitro transcription and for generation of the authentic 3' end of the RNA transcript, respectively. All restriction endonucleases were purchased from New England Biolabs (Beverly, Mass.).

A mammalian expression vector, pXJ (Xie et al., 2013), driven by a cytomegalovirus (CMV) promoter was used to express the polyprotein E24-NS1-NS2A-HA of ZIKV strain FSS13025. The C-terminal 24 amino acids of the E protein were retained to ensure the correct targeting and processing of NS1 in the ER membrane. The gene cassette encoding E24-NS1-NS2A was amplified from pFLZIKV (Shan et al., 2016b) by PCR using primer pair P1 (5'-GATGCGGCCG-CACCATGAATGGATCTATTTCCCTTATGTGCTTG-3' SEQ ID NO: 1) and reverse primer P2 (5'-TAATCTG-GAACATCGTATGGGTAGGATCCCCGCTTCCCACTC-CTTGTGAGCA-3' SEQ ID NO: 2). The human influenza hemagglutinin (HA) tag (GSYPYDVPDYA SEQ ID NO: 3) sequence was in-frame fused to the C-terminus of NS2A through a second PCR using primer P1 and P3 (5'-GAC-CTCGAGCTAAGCGTAATCTGGAACATCGTATGGG-TAGGATCC-3' SEQ ID NO: 4). The purified PCR fragment was cloned into pXJ vector through restriction enzymes NotI and XhoI. All plasmids were validated by restriction enzyme digestion and DNA sequencing from GENEWIZ (South Plainfield, N.J.). Other primer sequences and the complete pFLZIKV-PRV sequence are available upon request.

RNA In Vitro Transcription, Electroporation and Immunofluorescence Assay.

Plasmid linearization, RNA in vitro transcription and Vero cell electroporation were performed according to previously described protocols (Shan et al., 2016b). After electroporation, cells were seeded in a T-175 flask for virus production or 8-well chamber slide for monitoring E protein expression by immunofluorescence assay (IFA). IFA was performed as described previously (Shan et al., 2016b). Antibody 4G2 and goat anti-mouse IgG conjugated with Alexa Fluor®488 were used as primary and secondary antibodies, respectively. Finally, the cells were mounted in a mounting medium with DAPI (4',6-diamidino-2-phenylindole; Vector Laboratories, Inc., Burlingame, Calif.). Fluorescence images were acquired by a fluorescence microscope equipped with a video documentation system (Olympus, Shinjuku, Tokyo, Japan).

Virus Replication Kinetics and Plaque Assay.

C6/36 cells ($1.2\times10^6$ cells/well), BHK-21 cells ($8\times10^5$ cells/well), Vero cells ($8\times10^5$ cells/well) or Huh7 cells ($8\times10^5$ cells/well) were seeded into a 6-well plate one day prior to infection. At 16-20 h post-seeding, cells were infected with WT or mutant ZIKV at an MOI 0.01. Infection was performed in triplicate at 30° C. (C6/36 cells) or 37° C. (BHK-21, Vero and Huh7 cells). After 1 h incubation, virus inoculum were removed and cells were washed extensively by PBS to eliminate unabsorbed viruses. Afterwards, 3 ml fresh medium was added to each well. From day 1 to 6 post-infection, supernatants were collected daily and clarified by centrifugation at 500 g for 5 min prior to storage at −80° C. Virus in the culture fluids were determined by standard cytopathogenic effect-based plaque assay on Vero cells (Shan et al., 2016b). Plaques formed on Vero monolayers were stained by crystal violet after 4 days of infection.

Replicon Transient Transfection Assay.

This assay was performed as described previously (Xie et al., 2016). WT or NS1 K265E (10 μg) ZIKV FSS13025 replicon RNAs were electroporated into Vero cells. At given time points, cells were washed twice with PBS and lysed in 100 μl 1× Renilla luciferase lysis buffer (Promega, Madison, Wis.). Luciferase signals were immediately measured by Cytation 5 (Biotek, Winooski, Vt.) according to the manufacturer's instructions.

Plaque Purification.

Vero cells ($8\times10^5$ per well) were seeded into a 6-well plate. At 18-24 hour post-seeding, 200 μl serial dilutions of ZIKV ($10^2$ to $10^5$ PFU/ml) were inoculated onto the monolayer for infection at 37° C. for 1 hour. Afterwards, virus inoculants were replaced with 3 ml of the first overlay (DMEM supplemented with 3.7 g/L NaHCO3, 2% FBS [v/v], 1% penicillin/streptomycin [v/v] and 1% Lonza Sea-Plaque™ agarose [w/v]). Plates were incubated at 37° C. with 5% CO2. After four days of incubation, 3 ml of the second overlay (first overlay supplemented with 1/50 0.33% neutral red solution [Sigma]) was added to the top of the first layer. Plates were incubated at 37° C. with 5% CO2 for another two days. Sequentially, individual plaques were harvested and transferred into a 24-well plate pre-seeded with $2\times10^5$ Vero cells. After 2-3 days of incubation, cytopathic effects occurred in 24-well plates. Immediately, supernatants were harvested, clarified by centrifugation at 500 g for 5 min and stored at −80° C. The titers and plaque morphologies of all isolates were determined by plaque assay (Shan et al., 2016b). The cDNA sequence of the viral genomes from three large and three small plaque isolates were determined by Sanger sequencing.

Quantitative Reverse Transcription PCR (qRT-PCR).

Viral RNAs in culture fluids were extracted using QIAamp viral RNA minikit (Qiagen), and intracellular total RNAs were isolated using an RNeasy minikit (Qiagen). Extracted RNAs were eluted in 50 μl RNase-free water. One specific probe (5'-FAM/AGCCTACCT/ZEN/TGACAAGCAATCAGACACTCAA/3IABkFQ-3' SEQ ID NO: 5) and a primer set (ZIKV 1193F: 5'-CCGCTGC-CCAACACAAG-3' SEQ ID NO: 6; ZIKV 1269R: 5'-CCACTAACGTTCTTTTGCAGACAT-3' SEQ ID NO: 7) were used to determine the ZIKV RNA copies. The probe contains a 5'-FAM reporter dye, 3' IBFQ quencher, and internal ZEN quencher. qRT-PCR assays were performed on the LightCycler® 480 System (Roche) following the manufacturer's protocol by using 15-0 reactions of the QuantiTect Probe RT-PCR Kit (QIAGEN) and 1.50 RNA templates. In vitro transcribed full-length ZIKV RNAs were used as RNA standard for RT-PCR quantification. The mRNA level of the housekeeping gene glyceraldehyde-3-phophate dehydrogenase (GAPDH) was measured using an iScript one-Step RT-PCR kit with SYBR green (Bio-Rad) and a primer pair M GAPDH-F (5'-AGGTCGGTGTGAACGGATTTG-3' SEQ ID NO: 8) and M GAPDH-R (5'-TGTAGACCATG-TAGTTGAGGTCA-3' SEQ ID NO: 9).

Quantification of Extra- and Intracellular Infectious Virions.

At selected time points, about 1 ml of culture fluids were harvested and centrifuged at 500 g for 5 min to remove cell debris prior to storage at −80° C. Infected cells were washed three times with cold PBS to remove unbound virions. As indicated in FIG. 4, a stringent wash in cold alkaline-high-salt solution (1 M NaCl and 50 mM sodium bicarbonate, pH 9.5) for 3 mins was applied to remove cell surface-associated virus. After twice cold-PBS washes, the cells were detached using 0.25% Trypsin-EDTA (ThermoFisher Scientific) and suspended in 3 ml DMEM medium containing 2% FBS. Total cells were collected by centrifugation at 1,000 g for 5 min. The cell pellets were resuspended in 250 µl DMEM medium with 2% FBS. One hundred microliters of the cell suspensions was centrifuged at 1,000 g for 5 min to pellet the cells; the pelleted cells were then used for intracellular viral RNA. The remaining 150 µl of cell suspensions was lysed using a single freeze-thaw cycle (frozen at −80° C. and thawed at 37° C.). Afterwards, cellular debris was removed by centrifugation at 3,200 g for 5 min at 4° C., and the supernatant was harvested for plaque assay to determine the intracellular infectivity.

Co-Immunoprecipitation (Co-IP).

Co-IPs were performed according to a previous described protocol (Zou et al., 2014) with some modifications. For infection samples, 3×10$^6$ Vero cells in 6-cm dishes were infected with recombinant WT or NS1 K265E ZIKV strain FSS13025 at MOI 1.0. At 32 h p.t., cells were washed three times with PBS and lysed in 1 ml Pierce™ IP lysis buffer at 4° C. for 30 min. For transfection samples, 3×10$^6$ HEK293T cells in 6-cm dishes were transfected with 5 µg of plasmids encoding WT or NS1 K265E mutated polyprotein E24-NS1-NS2A-HA using X-tremeGENE 9 DNA transfection reagent (Roche) according to the manufacturer's instructions. At 42 h p.t., cells were washed twice with cold PBS an lysed in 1 ml immunoprecipitation (IP) buffer (20 mM Tris, pH 7.5, 100 mM NaCl, 0.5% DDM, and EDTA-free protease inhibitor cocktail [Roche]) with rotation at 4° C. for 1 h. All cell lysates were clarified by centrifugation at 15,000 rpm at 4° C. for 30 min and subjected to co-IP using protein G-conjugated magnetic beads according to the manufacturer's instructions (Millipore). Briefly, immune complexes were formed at 4° C. overnight by mixing 400 µl of cell lysate with 2 µg corresponding antibodies (rabbit anti-NS1, mouse anti-HA, rabbit control IgGs or mouse control IgGs) in a 500 µl reaction system containing 300 mM sodium chloride. Subsequently, the complexes were precipitated with protein G-conjugated magnetic beads at 4° C. for 1 h with rotation, followed by washing extensively with phosphate-buffered saline (PBS) containing 0.1% Tween 20 (Sigma). Finally, proteins were eluted with 4× lithium dodecyl sulfate (LDS) sample buffer (ThermoFisher Scientific) supplemented with 100 mM DTT, heated at 70° C. for 10 min, and analyzed by Western blotting described as below.

SDS-PAGE and Western blotting. Proteins were resolved in 12% SDS-PAGE gels and transferred onto a polyvinylidene difluoride (PVDF) membrane by using a Trans-Blot Turbo transfer system (Bio-Rad Laboratories, Hercules, Calif.). The blots were blocked in TBST buffer (10 mM Tris-HCl, pH 7.5, 150 mM NaCl, and 0.1% Tween 20) supplemented with 5% skim milk for 1 h, followed by probing with primary antibodies (1:2,000 dilution) for 1 h at room temperature. After two washes with TBST buffer, the blots were incubated with a goat anti-mouse or goat anti-rabbit IgG conjugated to HRP (1:20,000 dilution) in TBST buffer with 5% milk for 1 h, followed by three washes with TBST buffer. The antibody-protein complexes were detected using Amersham ECL Prime Western blotting detection reagent (GE Healthcare, Chicago, Ill.).

Mouse Experiments.

A129 mice (interferon type I receptor-knockout) were used to examine the virulence of recombinant WT or NS1 K265E ZIKV FSS13025. Experiments were performed according to a previously described protocol with some modifications (Shan et al., 2016b). In brief, 6-week-old A129 mice were infected with 10$^4$ PFU via the intraperitoneal route. Eight mice were used for each group. Calcium and magnesium-free DPBS (ThermoFisher Scientific) was used to dilute the virus stocks to the desired concentration. DPBS injection was used as mock-infection. On day 1 to 4 post-infection, four mice from each cohort were bled via the retro-orbital sinus (RO) after being anesthetized. Serum was clarified by centrifugation at 6000 g for 5 min and immediately stored at −80° C. prior to plaque assay for viremia. All animal work was completed in compliance with the UTMB policy as approved by the Institutional Animal Care and Use Committee (IACUC).

Infection of Mosquitoes with ZIKV.

Aedes aegypti colony mosquitoes derived from Galveston, Tex., were fed for 30 min on blood meals. The blood meals consist of 1% (weight/vol) sucrose, 20% (vol/vol) FBS, 5 mM ATP, 33% (vol/vol) PBS-washed human blood cells (UTMB Blood Bank), and 33% (vol/vol) DMEM medium. The 1 ml-blood meals were combined with 1 ml virus offered in Hemotek 2-ml heated reservoirs (Discovery Workshops) covered with a mouse skin. Virus titer in the blood meals ranged from 6.0 to 6.5 log 10 PFU/ml. Infectious blood meals were loaded on cartons containing A. aegypti. Engorged mosquitoes were incubated at 28° C., 80% relative humidity on a 12:12 h light:dark cycle with ad libitum access to 10% sucrose for 14 days, then frozen at −20° C. overnight. To assess infection, whole bodies of individual mosquitoes were individually homogenized (Retsch MM300 homogenizer, Retsch Inc., Newton, Pa.) in DMEM with 20% FBS and 250 µg/ml amphotericin B. The samples were then centrifuged for 10 min at 5,000 rpm. Afterwards, 50 µl of supernatants were inoculated into 96-well plates containing Vero cells at 37° C. and 5% CO2 for 3 days. Cells were fixed with a mixture of ice-cold acetone and methanol (1:1) solution and immunostained as described previously (Shan et al., 2016b). The infection rate was calculated using the number of virus-positive mosquito bodies divided by the total number of engorged and incubated mosquitoes.

Results

Identification of NS1 K265E Mutation.

Figures 1A, 1B, 1C, 1D, 1E, 1F, 1G:
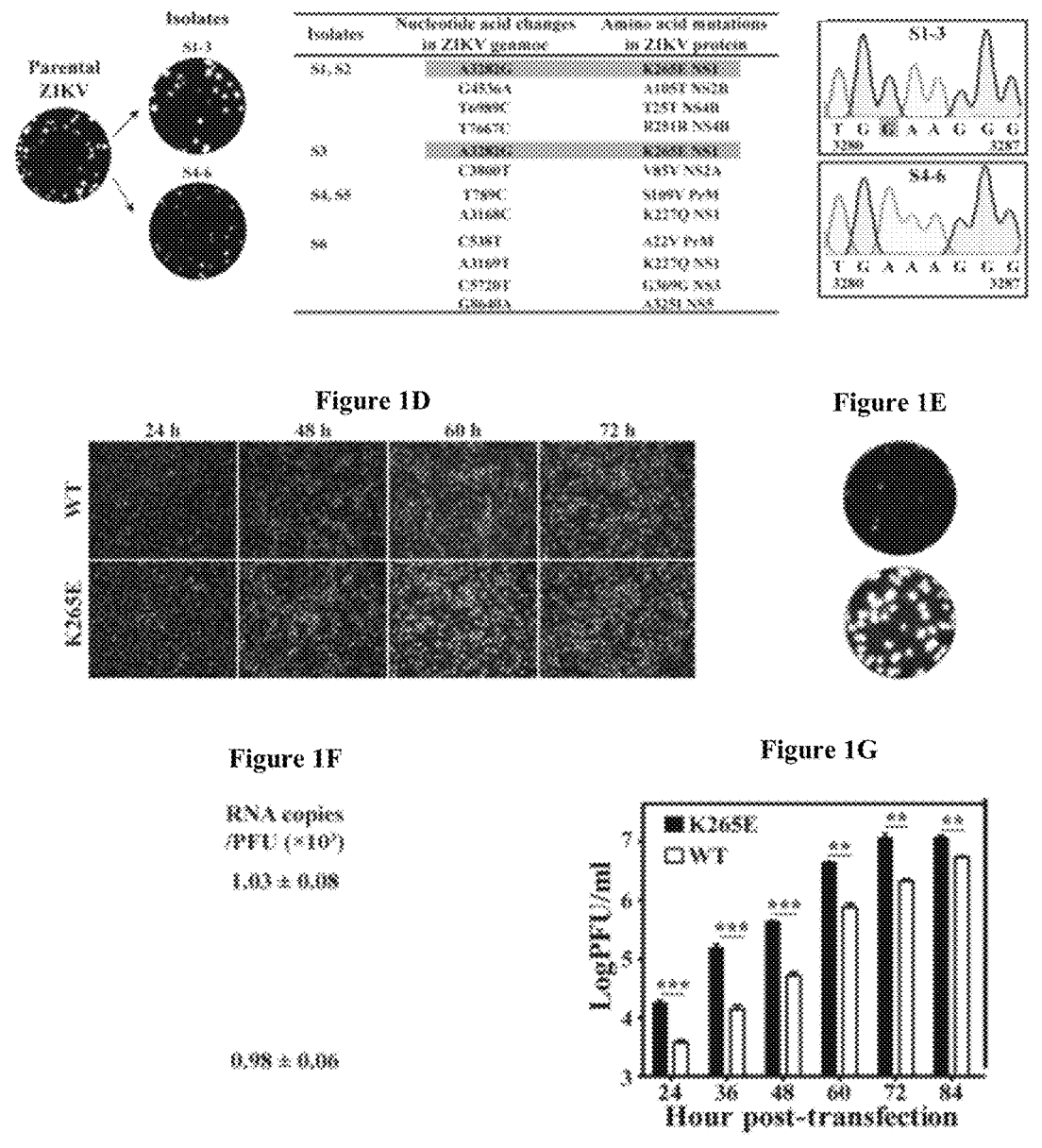

To identify cell-adaptive mutation(s) that can increase the yields of ZIKV production on Vero cells, we used a one-step plaque-purification approach to isolate virus clones with increased replication competency using Cambodian strain FSS13025. This ZIKV strain was isolated in 2010 from the blood of a three-year old patient from Cambodia (Heang et al., 2012), and had been cultured thrice on Vero cells. This parental isolate generated heterogeneous plaque sizes on Vero cells (FIG. 1A, left panel), from which we purified viruses three large (S1-3) and three small plaques (S4-6). Representative plaque morphologies of the purified viruses are shown in FIG. 1A (right panels). Complete-genome sequencing was performed for the purified S1-6 viruses (FIG. 1B). All three large plaque biological clones (S1-3) shared an adenine-to-guanine substitution at genomic position 3,282 (A3282G; GenBank KU955593.1), resulting in a Lys-to-Glu change at the position 265 in NS1 protein (K265E). The sequence chromatograph showed a highly homogeneous A3282G mutation for S1-3 viruses, whereas no such mutation was recovered in any of the S4-6 biologically cloned viruses exhibiting small plaques (FIG. 1C). The results suggested that NS1 K265E mutation may enhance ZIKV replication on Vero cells.

Characterization of Recombinant NS1 K265E ZIKV FSS13025.

Since mutations other than NS1 K265E were also recovered from S1-3 viruses, we engineered the NS1 K265E mutation into the ZIKV strain FSS13025 to verify its role in increased plaque morphology. Both WT and NS1 K265E mutant genomic RNAs were electroporated into Vero cells. An increasing number of the transfected cells expressed viral E protein from 24 to 72 h post-transfection (p.t.); interestingly, the K265E mutant RNA produced more E-positive cells than the WT at 48 and 72 h p.t. (FIG. 1D). In addition, this mutant produced larger plaques than the WT virus (FIG. 1E).

To examine the effect of NS1 K265E on viral infectivity, we determined the RNA copy/plaque-forming unit (PFU) ratio for both WT and NS1 K265E viruses. The extracellular viral RNA copies represented total virus (including both infectious and non-infectious) released into the culture fluids, while the PFU numbers indicated the amounts of infectious virions. Both the WT and mutant (collected at 72 h p.t.) showed similar RNA copy/PFU ratios (FIG. 1F), indicating that NS1 K265E did not affect viral infectivity. Corroborating the plaque assay and IFA results, the mutant RNA yielded significantly more infectious virus than the WT RNA after transfection of cells (FIG. 1G). Genomic sequencing of the recombinant mutant virus revealed no mutations other than the engineered NS1 K265E change (data not shown). Collectively, the results demonstrated that the NS1 K265E mutation was responsible for the enhanced ZIKV replication on Vero cells.

Figure 2B:
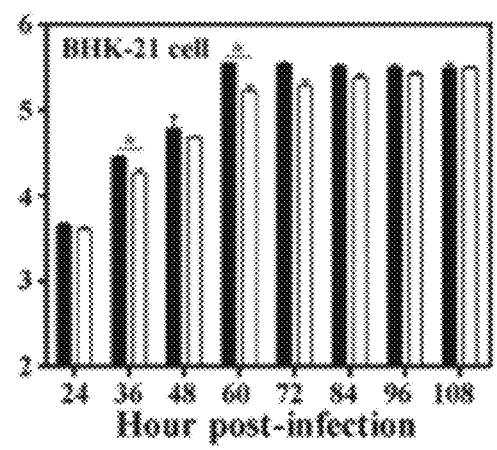
Figure 2C:
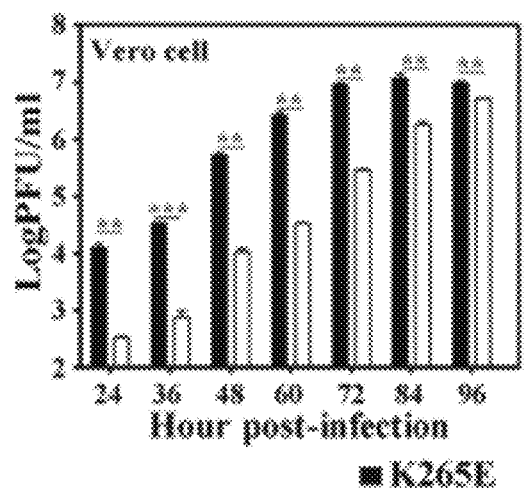
Figure 2D:
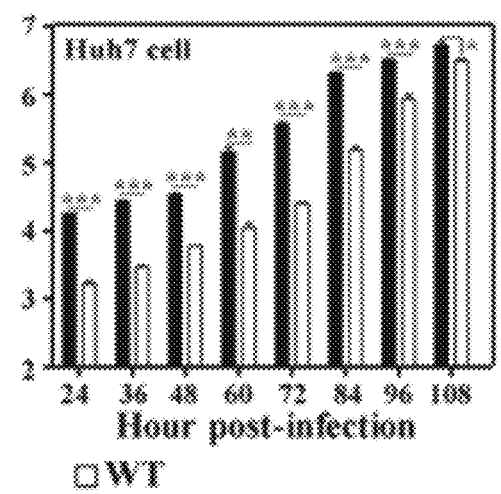

Comparison of viral replication of WT or NS1 mutant ZIKV FSS13025 in cell culture. We compared the replication kinetics of WT and NS1 K265E viruses in mosquito (C6/36), hamster (BHK-21), monkey (Vero), and human (Huh7) cell lines. Interestingly, the mutant and WT viruses showed comparable replication kinetics on C6/36 and BHK-21 cells (FIG. 2A-B). In contrast, the mutant virus replicated much faster than the WT virus on Vero and Huh7 cells (FIG. 2C-D). Specifically, the mutant virus peaked at 84 h p.i. with a titer up to $10^7$ PFU/ml on Vero cells. Overall, the data suggested that NS1 K265E improved viral replication in a cell type-dependent manner.

NS1 K265E mutation enhances the replication of ZIKV strain PRVABC59 in Vero cells. To examine whether the effects of NS1 K265E on viral replication is ZIKV strain-dependent, we engineered this mutation into a new infectious cDNA clone of ZIKV Puerto Rico strain PRVABC59 (GenBank number KU501215) isolated in 2015 (Lanciotti et al., 2016). We chose PRVABC59 because this strain was previously used to produce an inactivated vaccine [with monkey efficacy (Abbink et al., 2016)] that is currently in phase I clinical trials (https://clinicaltrials.gov). As depicted in FIG. 3A, six RT-PCR fragments spanning the complete viral genome were individually cloned and assembled into the full-length cDNA of ZIKV in a single-copy vector pCC1BAC, resulting in plasmid pFLZIKV-PRV. The plasmid could be induced to generate 10-20 copies/cell using L-arabinose in *E. coli* strain TransforMax™ EPI300™. Compared with the parental ZIKV isolate, the infectious cDNA clone had five nucleotide mutations (A1337G, A2768T, A2771G, T8408A and C9176T), none of which changed the amino acid sequence (FIG. 3B).

The RNA transcribed from pFLZIKV-PRV was infectious, as evidenced by increasing E-positive cells upon transfection into Vero cells (FIG. 3C). The culture fluids harvested from WT ZIKV-PRV RNA-transfected cells produced plaques on Vero cells on day 4 p.i. (FIG. 3D). More importantly, the NS1 K265E mutant RNA-transfected cells showed a faster increase in E-positive cell numbers (FIG. 3C) than the WT. The NS1 K265E virus produced larger plaques than the WT ZIKV-PRV (FIG. 3D). The mutant RNA and virus replicated significantly faster than the WT counterparts in transfected (FIG. 3E) and infected Vero cells (FIG. 3F), respectively. These data demonstrated that the replication enhancement of NS1 K265E was not ZIKV strain-dependent.

NS1 K265E mutation enhances virus assembly, but retards virus entry. To understand which step(s) of the viral infection cycle were affected by NS1 K265E mutation, we engineered the mutation into a luciferase reporter ZIKV replicon (Xie et al., 2016). After transfection of Vero cells with equal amounts of replicon RNAs, the WT and mutant produced comparable amounts of luciferase activity 2-46 h p.t. (FIG. 4A). The replicon results demonstrated that NS1 K265E mutation did not affect viral translation and RNA synthesis.

Next, we used recombinant Cambodian FSS13025 virus to examine the effect of the NS1 K265E mutation on a single infection cycle. FIG. 4B depicts the experimental flowchart. The total infection time was restricted to 20 h to avoid multiple rounds of infection. Vero cells were infected with equal amounts of WT and NS1 K265E mutant viruses at 37° C. After 1 h p.i., cells were washed with PBS to remove unattached viruses. Intracellular viral RNAs were quantified at 1, 14, and 20 h post-infection. Before extracting intracellular viral RNA, the cells were thoroughly washed with an alkaline high-salt solution to remove cell membrane-associated viruses. Besides intracellular viral RNA, we also measured intracellular and extracellular virions (using plaque assay) as well as extracellular viral RNAs at 14 and 20 h p.i. (FIG. 4C). Compared with the WT, the K265E mutant produced slightly more intracellular viral RNA, but generated >10-fold more extracellular viral RNA as well as >10-fold more intracellular and extracellular infectious viruses at 14 and 20 h p.i. (FIG. 4C). The data indicated that NS1 K265E mutation increased virus assembly in Vero cells.

Surprisingly, at 1 h p.i., the intracellular level of mutant viral RNA of was about half of the WT virus (FIG. 4C), suggesting that the mutation reduced virus attachment/entry. This observation prompted us to perform the experiment outlined in FIG. 4D to dissect the effect of NS1 K265E on virus attachment and/or entry. Vero cells were incubated with equal amounts of WT or mutant virus at 4° C. for 1 h. At this temperature, viruses could attach to the cell surface without entry. Both WT and mutant viruses bound to Vero cells with equal efficiencies (FIG. 4E, data set I). Further incubation at 37° C. initialized virus entry. After 0.5 h incubation at 37° C., the amount of intracellular mutant RNA was about 60% of the intracellular WT RNA (FIG. 4E, data set II); however, after additional 2.5 and 5.5 h incubation at 37° C., equal amounts of intracellular viral RNAs were detected for mutant and WT viruses (FIG. 4E, data set III&IV). Taken together, the results suggested that, besides enhancement of virion assembly, NS1 K265E may slow virus entry (FIG. 4F)

Mutation K265E increases NS1/NS2A interaction. The structure of ZIKV NS1 consists of an N-terminal β-roll, an epitope-rich wing domain, and a C-terminal β-ladder (Brown et al., 2016). Residue K265 is located at the C-terminal β-ladder, and is spatially clustered with two other positively charged residues (R294 and R347) on the surface of the NS1 molecule (FIG. 5A), suggesting that this region may participate in protein/protein interactions. Since NS1 was reported to interact with structural protein prM and E during virus assembly (Scaturro et al., 2015), we performed co-immunoprecipitation to examine whether mutation K265E affected those interactions (FIG. 5B). Western blotting of total cell lysates (collected at 32 h p.i.) showed higher levels of NS1, prM, and E protein expression in the mutant virus-infected cells than those in the WT-infected cells (FIG. 5C, right two lanes). This was expected because the mutant virus replicated more robustly than the WT. Interestingly, both prM and E proteins were co-immunoprecipitated by NS1 in the WT- and mutant-infected cells (FIG. 5C). Quantification (by normalizing the NS1 protein amounts) showed that WT and mutant K265E NS1 pulled down the prM or E protein at comparable efficiencies (FIG. 5D), indicating that the mutation did not affect the NS1/prM or NS1/E interactions.

Since NS2A is known to modulate flavivirus assembly (Kummerer and Rice, 2002; Leung et al., 2008; Xie et al., 2013), we tested whether K265E changed the NS1/NS2A interaction. Due to the lack of availability of specific antibodies against ZIKV NS2A, we performed the co-immunoprecipitation experiment using a plasmid co-expressing NS1 and HA-tagged NS2A proteins. As shown in FIG. 5E, a plasmid encoding the polyprotein E24-NS1-NS2A-HA (E24 representing the last 24 amino acids of E protein to keep the correct topology of NS1-NS2A-HA on the ER membrane) was transfected into HEK293T cells. Upon translation, the polyproteins would be processed into E24, NS1, and NS2A-HA by host signalases (Lindenbach, 2013). Cell lysates were immunoprecipitated by mouse anti-HA IgG or control IgG. NS1 could be pulled down together with NS2A-HA by the mouse anti-HA IgG, but not by the control IgG (FIG. 5F), demonstrating that NS1 interacted specifically with NS2A. Importantly, NS2A-HA pulled down significantly (1.2-fold) more K265E NS1 than the WT NS1 (FIG. 5G), suggesting that the mutation increased the binding of NS1 to NS2A. It should be noted that two species of NS2A-HA protein appeared in the denature SDS-PAGE (FIG. 5F), probably due to unknown modification(s) or degradation of NS2A-HA. The nature of the two NS2A-HA species remains to be determined.

Figure 6A:
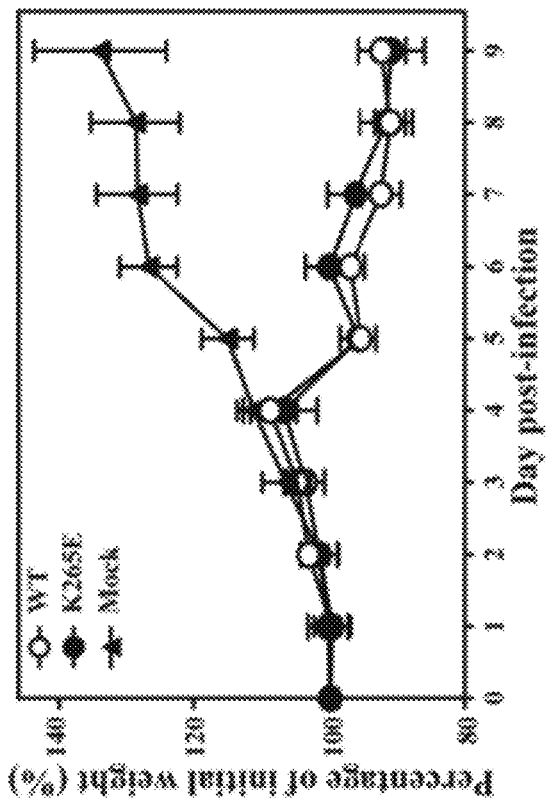
FIG. 6A-B contains a comparison of virulence between recombinant WT and NS1 K265E ZIKV strain FSS13025 in A129 mice. (A) Viremia from day 1 to 4 post-infection. Viremia were quantified using plaque assay. Limitation of detection (L.O.D.) is 100 PFU/ml. Each data point represents the averaged viremia from four mice. (B) Weight loss. The averaged percentages of initial weight from eight mice are presented. The two-way ANOVA multiple comparison was used to evaluate the statistical significance.
Figure 6B:
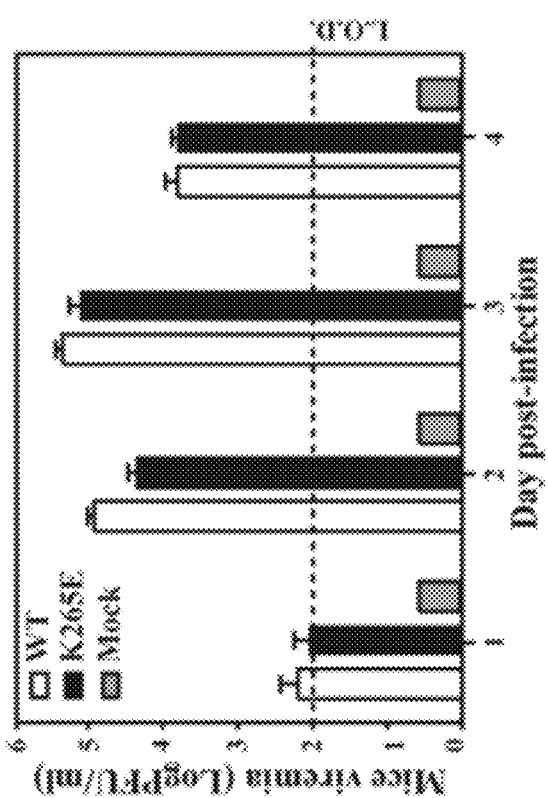

NS1 K265E mutation does not affect ZIKV virulence in the A129 mouse model. We evaluated the in vivo virulence of WT and mutant NS1 K265E ZIKVs in the A129 mice by monitoring the viremia and weight loss (Shan et al., 2016b). Equal amounts ($1 \times 10^4$ PFU) of each virus were inoculated into mice via the intraperitoneal (i.p.) route. Unexpectedly, the WT and mutant viruses produced statistically indistinguishable levels of viremia (FIG. 6A) and weight loss (FIG. 6B). These data indicated that K265E did not affect ZIKV virulence in the A129 mouse model.

NS1 K265E mutation decreases viral infection of *Ae. aegypti* mosquitoes. To understand whether the NS1 K265E mutation affects viral fitness in mosquitoes, we determined the oral susceptibility of *A. aegypti* using artificial human bloodmeals containing approximately $10^6$ PFU/ml of the K265E mutant or WT virus (Shan et al., 2016b). On day 14 post-feeding, engorged mosquitos were analyzed for the presence of virus in the bodies to estimate infection rates. As summarized in Table 1, NS1 K265E virus showed a significantly lower infection rate than the WT virus in mosquitoes, demonstrating that the mutation reduced virus fitness for infection of *A. aegypti* mosquitoes.

TABLE 1

Infection of WT or NS1 K265E ZIKV FSS13025 in *A. aegypti*.

| Virus | Blood-meal titer (LogPFU/ml) | Infection rate (%)* |
|---|---|---|
| WT | 6.0 | 20/37 (54) |
| K265E | 6.1 | 8/42 (19) |

<sup>a</sup>After blood meal, viral titers for both parental and recombinant viruses were measured by plaque assay to ensure the accuracy of virus amounts in the blood meal.
<sup>b</sup>Infection rate = (number of infected mosquitos/number of engorged mosquitos) × 100%.
*p = 0.002, Fisher's exact test, 2-tailed.

Figure 7A:
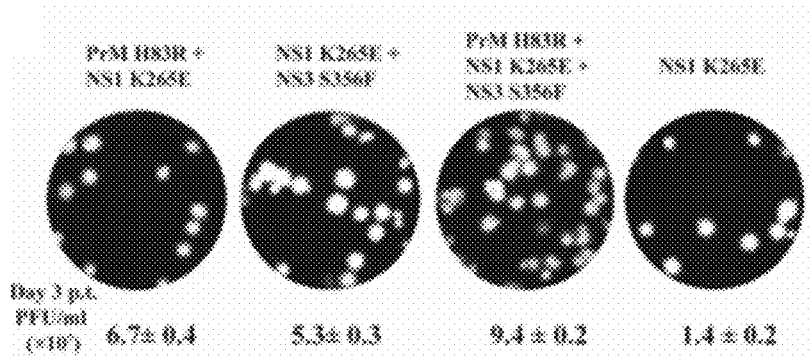
FIG. 7A-C shows that PrM H83R, NS1 K265E and NS3 S356F mutations further increase viral yield. (A) Plaque morphologies. Viruses harvested on day 3 post-transfection were assayed by plaque assay on Vero cells. Plaques were developed on day 4 post-infection. (B) Growth kinetics of ZIKV-PRV mutant viruses. Vero cells were infected with equal amounts of ZIKV-PRV mutant viruses (MOI 0.01). The multiple t test was performed to analyze the statistical significance at each time point. (C) Comparison of replication kinetics of the WT ZIKV PRVABC59 strain with its triple mutant. The fold differences in viral titers between the WT and triple mutant are indicated.
Figure 7B:
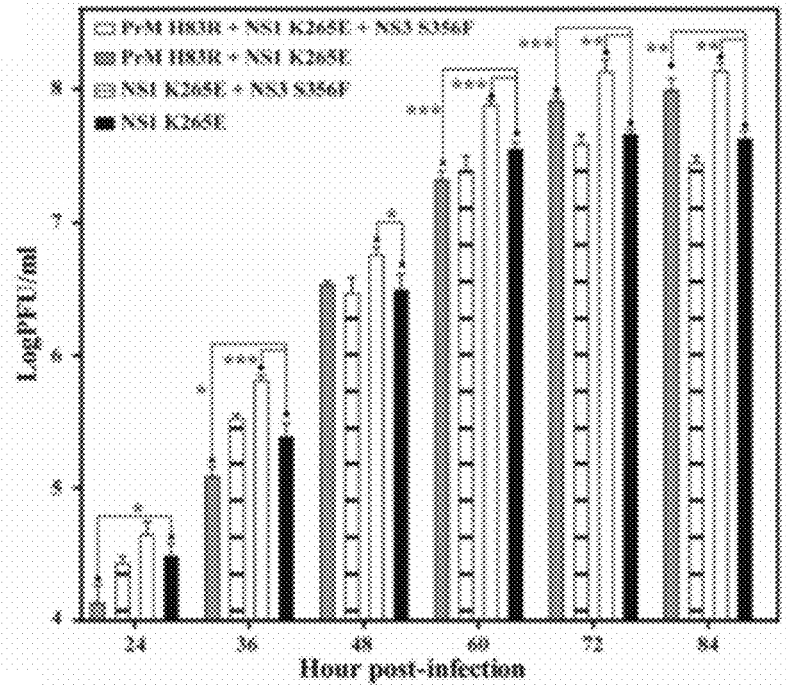
Figure 7C:
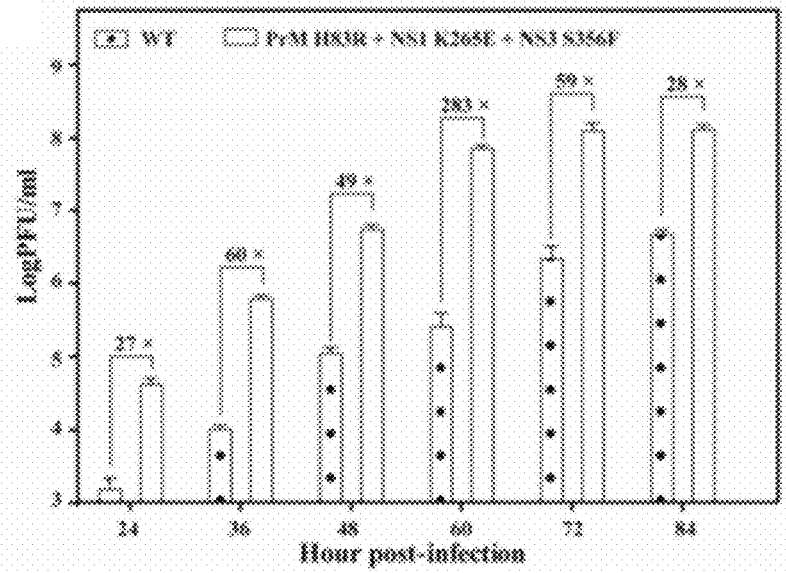

PrM H83R and NS3 S356F mutations further increase viral yield on Vero cells. Although the above results demonstrated that NS1 K265E enhanced viral yield, we asked whether other cell adaptive mutations could further increase virus production on Vero cells. To address this question, we engineered two additional cell-adaptive mutations (prM H83R and NS3 S356F) in the context of NS1 K265E pFLZIKV-PRV. PrM H83R mutation was identified from passaging of ZIKV FSS13025 on Vero cells (our unpublished data). NS3 S356F mutation was recently reported to increase ZIKV replication in cell culture (Tsetsarkin et al., 2016). In vitro transcribed genomic RNAs (prM H83R+NS1 K265E; NS1 K265E+NS3 S356F, and prM H83R+NS1 K265E+NS3 S356F) were electroporated into Vero cells. At 72 h p.t., about 4-, 3-, and 6-fold more viruses were produced from the prM H83R+NS1 K265E, NS1 K265E+NS3 S356F, and prM H83R+NS1 K265E+NS3 S356F RNA-transfected cells than the NS1 K265E RNA-transfected cells, respectively (FIG. 7A). All three mutants generated similar plaque morphologies as the NS1 K265E virus on Vero cells (FIG. 7A). Importantly, replication kinetics showed that the triple mutant virus (prM H83R+NS1 K265E+NS3 S356F) produced a peak viral titer of $1.6 \times 10^8$ PFU/ml that was significantly higher than the other mutants (FIG. 7B). FIG. 7C directly compares the replication kinetics of the WT ZIKV PRVABC59 strain with its triple mutant. Remarkably, the triple mutant generated ≥27-fold more virus than the WT at various time post-infection. The results clearly indicate that the triple mutant would be an ideal candidate for the manufacturing of inactivated vaccine.

Virus Thermostability Assay.

Figure 8:
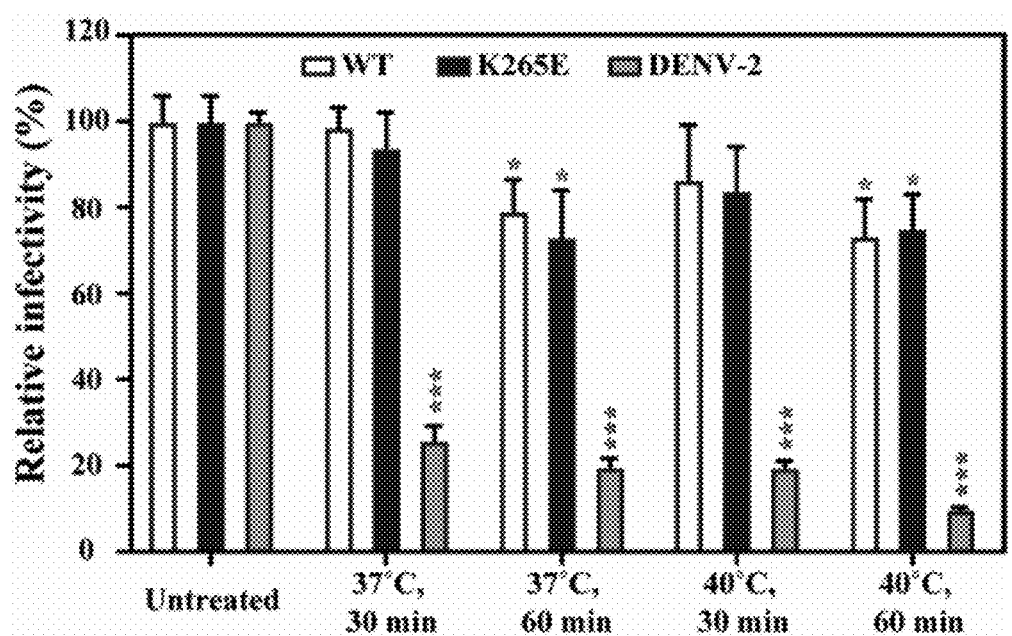
FIG. 8 shows a thermostability analysis of recombinant WT and NS1 K265E mutant ZIKV strain FSS13025. Data indicate the means from three independent experiments. A one-way ANOVA test was performed to analyze the statistic differences between each treatment group and corresponding un-treated group.

Equal amounts ($2 \times 10^5$ PFU/ml) of recombinant WT and NS1 K265E mutant ZIKV strain FSS13025, and DENV-2 New Guinea strain (as positive control) in DMEM medium containing 2% FBS were pre-incubated at 37° C. or 40° C. for 30 min or 60 min, respectively. After the treatment, virus titers in each sample were determined by plaque assay. For determining the initial input amount of viruses, untreated samples were immediately titrated for plaque assay. The relative infectivity was calculated by normalizing the virus titers of treatment groups to those of untreated groups. Experiments were performed three times in triplicate. See FIG. 8.

CONCLUSIONS

Purified inactivated vaccine (PIV) is one of the frontrunners in the rapidly evolving ZIKV vaccine pipeline. A PIV using ZIKV strain PRVABC59 completely protects rhesus macaques from ZIKV challenge (Abbink et al., 2016), and is currently undergoing a phase I clinical trial (https://clinicaltrials.gov). Licensed PIVs have been developed for TBEV and JEV (Shan et al., 2016a). Technologies that can increase the yield of virus production with shortened manufacture time will greatly reduce the cost and increase the vaccine accessibility. Here, we report a ZIKV with triple mutations (prM H83R+NS1 K265E+NS3 S356F) that greatly increased viral replication in Vero cells. Our findings will be useful for PIV manufacture because Vero cells are approved for vaccine production (Griffiths, 1987).

The NS1 K265E mutation was initially identified from plaque purification using the parental ZIKV strain FSS13025. This mutation was consistently recovered from viruses recovered from large plaques, but not from small plaques (FIG. 1A-C). Using an infectious clone of ZIKV FSS13025, we confirmed that mutation K265E in NS1 was responsible for the enhanced viral replication (FIGS. 1D-G & 2C). Interestingly, the K265E mutation increased viral replication in Vero and Huh7 cells, but not in C6/36 and BHK-21 cells (FIG. 2), suggesting that the enhancement was cell type-dependent. When the same mutation was introduced into a clone derived from epidemic strain of ZIKV PRVABC59, it also increased viral replication in Vero cells (FIG. 3), indicating that its effect on viral replication was not ZIKV strain-dependent.

Mechanistically, we provided five lines of evidence that NS1 K265E modulates the steps of viral entry and assembly during an infection cycle. (i) NS1 K265E did not affect virus attachment to the cell surface (FIG. 4E), but delayed virus entry. At 1 h post-attachment at 37° C., the mutation reduced entry by 40%; however, entry reached WT levels at 3 and 6 h post-attachment at 37° C. (FIG. 4E). (ii) The NS1 K265E had no effect on viral protein translation and RNA synthesis in a luciferase replicon assay (FIG. 4A). (iii) The NS1 K265E mutation increased virus assembly, leading to higher levels of intracellular and extracellular infectious viruses (FIG. 4C). (iv) The RNA copy/PFU ratios of WT and NS1 K265E mutant viruses were indistinguishable (FIG. 1F), suggesting that the mutation did not affect virus maturation (e.g., cellular furin-mediated cleavage of prM to pr and M proteins). (v) Both WT and NS1 K265E ZIKV FSS13025 showed similar thermostability when incubated at physiological temperatures of 37° C. or 42° C. for up to 1 h (FIG. 8), suggesting that the mutation did not affect viral thermostability.

Flavivirus entry and assembly are tightly controlled by the spatial and temporal interplays between host and viral factors. How does the NS1 K265E mutation affect both ZIKV entry and assembly? The flavivirus NS1 is a multi-functional protein involved in viral replication (Lindenbach and Rice, 1997, 1999; Youn et al., 2012), virion assembly (Scaturro et al., 2015), and evasion of host immune response (Avirutnan et al., 2011; Chung et al., 2006). The crystal structure of ZIKV NS1 shows an elongated hydrophobic surface for membrane association and a polar surface that varies substantially among different flaviviruses (Brown et al., 2016). Amino acid K265, together with two nearby positively charged residues (R294 and R347), could contribute to the positive surface of the β-ladder domain of NS1 (FIG. 5A). The K265E mutation might perturb the charge in the β-ladder domain, leading to change(s) in network interactions between viral-viral or viral-host factors. Indeed, our co-immunoprecipitation experiments revealed that the mutation increased the NS1/NS2A interaction (FIGS. 5F&G) without affecting the NS1/prM and NS1/E interactions. Since NS2A has been well documented to modulate flavivirus assembly (Kummerer and Rice, 2002; Leung et al., 2008; Xie et al., 2013), the increased NS1/NS2A interaction might be responsible for the enhanced virion assembly. On the other hand, because the NS1 K265E-mediated enhancement of virion production was cell type-dependent, cellular factors (e.g., proteins and/or lipids) must be involved in the process of enhanced virion assembly. Proteomic analysis of host proteins that bind to NS1 or NS2A in infected cells could be pursued to identify cellular factors important for flavivirus assembly.

The flavivirus E protein interacts with multiple cell surface receptors and attachment factors to facilitate virus entry. Many cell surface factors are reported to mediate flavivirus entry, including heat shock proteins, phosphatidylserine receptors [TIM (Tyro3, Ax1, and Mer) and TAM (T cell, immunoglobulin, and mucin)], claudin-1, heparan sulfate, dendritic cell-specific intracellular adhesion molecular-3 grabbing nonintegrin (DC-SIGN), mannose receptor, and C-type lectin domain family 5 member A (Perera-Lecoin et al., 2014). ZIKV selectively binds to TAM, but not TIM phosphatidylserine transmembrane receptor (Hamel et al., 2015). The ER membrane contains phosphatidylserine lipids in the luminal leaflet (Leventis and Grinstein, 2010), and NS1 is proposed to assist in virion morphogenesis via its lipid-remodeling activity, membrane association capability, and interactions with viral non-structural and structural proteins (Scaturro et al., 2015). It is thus tempting to speculate that mutation K265E alters NS1's ability to recruit specific lipids during virion budding. The altered lipid components in virion bilayer could consequently modulate the kinetics of viral entry.

In contrast to the enhanced viral replication on Vero cells, NS1 K265E did not significantly change the virulence of ZIKV in the A129 mice (FIG. 6). The in vitro and in vivo discrepancy could be due to cell type-specific enhancement of the mutant virus replication (FIG. 2). In agreement with the in vivo results, NS1 K265E virus showed a WT level of viral replication on rodent BHK-21 cells (FIG. 2B). Therefore, caution should be taken when extrapolating mouse virulence result to non-human primates and humans. This is particularly important when the NS1 K265E mutation is engineered into a live-attenuated ZIKV vaccine candidate (for the purpose of increase in vaccine production on Vero cells). In such case, the effect of NS1 K265E mutation on virulence should first be directly evaluated in non-human primates.

In mosquito hosts, NS1 K265E virus replicated to the WT level on C6/36 cells, but significantly reduced its ability to infect A. aegypti (Table 1). The reduced vector infectivity of NS1 K265E ZIKV could explain its rarity in clinical isolates. Only 3 out of 169 ZIKV full-length sequences in the GenBank exhibit the NS1 K265E mutation. Since Vero cells are routinely used to isolate ZIKV, it remains to be determined whether the NS1 265E sequence from the 3 clinical isolates (GenBank number ANN83272, AOX49265, and AMS00611) resulted from adaptation to Vero cells during virus isolation.

Our study has provided a new platform to reproducibly generate high yields of ZIKV for PIV manufacture. Specifically, the infectious ZIKV cDNA clone of PRVABC59 containing the triple mutations (prM H83R+NS1 K265E+NS3 S356F) could be used to launch ZIKV production on Vero cells. The mechanism of how prM H83R and NS3 S356F mutations increase viral replication remains to be understood. In addition, further studies are needed to investigate the effect of prM H83R and NS3 S356F mutations on ZIKV virulence and vector infection. Nevertheless, compared with the traditional method of virus amplification from seed viruses, the cDNA clone-launched PIV manufacture platform has the advantages of higher yields, shortened manufacture time, higher reproducibility (viruses directly produced from in vitro synthesized RNA), and a reduced risk of contamination (due to the elimination of isolation and multiple rounds of passaging of seed viruses in cell culture). Since ZIKV strain PRVABC59 was used for the current PIV clinical trial, our mutant cDNA plasmid could be readily used for this vaccine manufacture.

In summary, this invention provides an infectious cDNA clone-launched platform to maximize the yield of ZIKV. A single NS1 protein substitution (K265E) was identified to increase ZIKV replication on Vero cells (a cell line approved for vaccine production) for both Cambodian FSS13025 and Puerto Rico PRVABC59 strains. The NS1 mutation did not affect viral RNA synthesis, but significantly increased virion assembly, probably through an increased interaction between NS1 and NS2A (a known regulator of flavivirus assembly). The NS1 mutant virus retained wildtype virulence in the A129 mouse model, but decreased its competence to infect *Aedes aegypti* mosquitoes. To further increase virus yield, we constructed an infectious cDNA clone of the clinical trial PIV strain PRVABC59 containing three viral replication-enhancing mutations (NS1 K265E, prM H83R, and NS3 S356F) that could generate a viral titer of >10$^8$ PFU/ml on Vero cells, and produced >25-fold more ZIKV than the wildtype parent on Vero cells. Taken together, the results demonstrate that the infectious cDNA clone containing these triple mutations represents an attractive platform to reproducibly generate high yields of ZIKV, which could be readily used for manufacture of PIV for a vaccine clinical trial. This cDNA clone-launched manufacture platform has the advantages of higher virus yield, shortened manufacture time, and minimized chance of contamination. The enhancement of virus production by the cell-adaptive triple mutations and the reported reverse genetic system could be used to manufacture the ZIKV strain PRVABC59-derived purified inactivated vaccine (PIV) that showed efficacy in monkeys and is currently in phase I clinical trial. High-yield manufacture of this PIV is essential for its development and vaccine access.

One skilled in the art will readily appreciate that the present invention is adapted to carry out the objects and obtain the ends and advantages mentioned, as well as those inherent therein. The prior examples along with the methods, procedures, treatments, molecules, and specific compounds described herein are presently representative of preferred embodiments, are examples, and are not intended as limitations on the scope of the invention. Changes therein and other uses will occur to those skilled in the art which are encompassed within the spirit of the invention as defined by the scope of the claims.

In the following listing of claims, all sequence numbers are given with reference to the amino acid sequences of the ZIKV proteins encoded by ZIKV strain FSS13025 (GenBank Accession No. KU955593.1 (SEQ ID NO: 10 and SEQ ID NO: 11)) but are applicable to all homologous sequences, as would be appreciated by one of skill in the art. This includes, for example, ZIKV strain PRVABC59.

The contents of the following references and all other references which are cited in this application are incorporated by reference in their entirety.

REFERENCES

1. Abbink, P., Larocca, R. A., De La Barrera, R. A., Bricault, C. A., Moseley, E. T., Boyd, M., Kirilova, M., Li, Z., Ng'ang'a, D., Nanayakkara, O., et al. (2016). Protective efficacy of multiple vaccine platforms against Zika virus challenge in rhesus monkeys. *Science* 353, 1129-1132.
2. Atieh, T., Baronti, C., de Lamballerie, X., and Nougairede, A. (2016). Simple reverse genetics systems for Asian and African Zika viruses. Sci Rep 6, 39384.
3. Avirutnan, P., Hauhart, R. E., Somnuke, P., Blom, A. M., Diamond, M. S., and Atkinson, J. P. (2011). Binding of flavivirus nonstructural protein NS1 to C4b binding protein modulates complement activation. *J Immunol* 187, 424-433.
4. Brown, W. C., Akey, D. L., Konwerski, J. R., Tarrasch, J. T., Skiniotis, G., Kuhn, R. J., and Smith, J. L. (2016). Extended surface for membrane association in Zika virus NS1 structure. *Nat Struct Mol Biol* 23, 865-867.
5. Chung, K. M., Liszewski, M. K., Nybakken, G., Davis, A. E., Townsend, R. R., Fremont, D. H., Atkinson, J. P., and Diamond, M. S. (2006). West Nile virus nonstructural protein NS1 inhibits complement activation by binding the regulatory protein factor H. *Proc Natl Acad Sci USA* 103, 19111-19116.
6. Dawes, B. E., Smalley, C. A., Tiner, B. L., Beasley, D. W. C., Milligan, G. N., Reece, L. M., Hombach, J., and Barrett, A. D. T. (2016). Research and development of Zika virus vaccines. *Npj Vaccines* 1, 16007.
7. Dick, G. W., Kitchen, S. F., and Haddow, A. J. (1952). Zika virus. I. Isolations and serological specificity. *Trans R Soc Trop Med Hyg* 46, 509-520.
8. Dowd, K. A., Ko, S. Y., Morabito, K. M., Yang, E. S., Pelc, R. S., DeMaso, C. R., Castilho, L. R., Abbink, P., Boyd, M., Nityanandam, R., et al. (2016). Rapid development of a DNA vaccine for Zika virus. *Science* 354, 237-240.
9. Griffiths, E. (1987). Acceptability of cell substrates for production of biologicals. Report of a WHO Study Group on Biologicals. *World Health Organization Technical Report* 747.
10. Hamel, R., Dejarnac, O., Wichit, S., Ekchariyawat, P., Neyret, A., Luplertlop, N., Perera-Lecoin, M., Surasombatpattana, P., Talignani, L., Thomas, F., et al. (2015). Biology of Zika Virus Infection in Human Skin Cells. *J Virol* 89, 8880-8896.
11. Heang, V., Yasuda, C. Y., Sovann, L., Haddow, A. D., Travassos da Rosa, A. P., Tesh, R. B., and Kasper, M. R. (2012). Zika virus infection, Cambodia, 2010. *Emerg Infect Dis* 18, 349-351.
12. Kostyuchenko, V. A., Lim, E. X., Zhang, S., Fibriansah, G., Ng, T. S., Ooi, J. S., Shi, J., and Lok, S. M. (2016). Structure of the thermally stable Zika virus. *Nature* 533, 425-428.
13. Kummerer, B. M., and Rice, C. M. (2002). Mutations in the yellow fever virus nonstructural protein NS2A selectively block production of infectious particles. *J Virol* 76, 4773-4784.
14. Lanciotti, R. S., Lambert, A. J., Holodniy, M., Saavedra, S., and Signor Ldel, C. (2016). Phylogeny of Zika Virus in Western Hemisphere, 2015. Emerg Infect Dis 22, 933-935.
15. Larocca, R. A., Abbink, P., Peron, J. P., Zanotto, P. M., Iampietro, M. J., Badamchi-Zadeh, A., Boyd, M., Ng'ang'a, D., Kirilova, M., Nityanandam, R., et al. (2016). Vaccine protection against Zika virus from Brazil. *Nature* 536, 474-478.
16. Lazear, H. M., Govero, J., Smith, A. M., Platt, D. J., Fernandez, E., Miner, J. J., and Diamond, M. S. (2016). A Mouse Model of Zika Virus Pathogenesis. *Cell Host Microbe* 19, 720-730.
17. Leung, J. Y., Pijlman, G. P., Kondratieva, N., Hyde, J., Mackenzie, J. M., and Khromykh, A. A. (2008). Role of nonstructural protein NS2A in flavivirus assembly. *J Virol* 82, 4731-4741.
18. Leventis, P. A., and Grinstein, S. (2010). The distribution and function of phosphatidylserine in cellular membranes. *Annu Rev Biophys* 39, 407-427.
19. Lindenbach, B. D., Murray, C. L., Thiel, H. J., Rice, C. M. (2013). Flaviviridae. In Fields Virology, 6th, Vol. 1, D. M. Knipe and P. M. Howley, eds. ((Philadelphia: Lippincott William & Wilkins), pp. 712-746).
20. Lindenbach, B. D., and Rice, C. M. (1997). trans-Complementation of yellow fever virus NS1 reveals a role in early RNA replication. *J Virol* 71, 9608-9617.
21. Lindenbach, B. D., and Rice, C. M. (1999). Genetic interaction of flavivirus nonstructural proteins NS1 and NS4A as a determinant of replicase function. *J Virol* 73, 4611-4621.

22. Perera-Lecoin, M., Meertens, L., Carnec, X., and Amara, A. (2014). Flavivirus Entry Receptors: An Update. *Viruses Basel* 6, 69-88.
23. Petersen, L. R., Jamieson, D. J., Powers, A. M., and Honein, M. A. (2016). Zika Virus. *N Engl J Med* 374, 1552-1563.
24. Rossi, S. L., Tesh, R. B., Azar, S. R., Muruato, A. E., Hanley, K. A., Auguste, A. J., Langsjoen, R. M., Paessler, S., Vasilakis, N., and Weaver, S. C. (2016). Characterization of a Novel Murine Model to Study Zika Virus. *Am J Trop Med Hyg* 94, 1362-1369.
25. Scaturro, P., Cortese, M., Chatel-Chaix, L., Fischl, W., and Bartenschlager, R. (2015). Dengue Virus Non-structural Protein 1 Modulates Infectious Particle Production via Interaction with the Structural Proteins. *PLoS Pathog* 11, e1005277.
26. Schuler-Faccini, L., Ribeiro, E. M., Feitosa, I. M. L., Horovitz, D. D. G., Cavalcanti, D. P., Pessoa, A., Doriqui, M. J. R., Neri, J. I., Neto, J. M. D., Wanderley, H. Y. C., et al. (2016). Possible Association Between Zika Virus Infection and Microcephaly—Brazil, 2015. *Mmwr-Morbid Mortal W* 65, 59-62.
27. Schwarz, M. C., Sourisseau, M., Espino, M. M., Gray, E. S., Chambers, M. T., Tortorella, D., and Evans, M. J. (2016). Rescue of the 1947 Zika Virus Prototype Strain with a Cytomegalovirus Promoter-Driven cDNA Clone. *mSphere* 1.
28. Shan, C., Xie, X., Barrett, A. D., Garcia-Blanco, M. A., Tesh, R. B., Vasconcelos, P. F., Vasilakis, N., Weaver, S. C., and Shi, P. Y. (2016a). Zika Virus: Diagnosis, Therapeutics, and Vaccine. *ACS Infect Dis* 2, 170-172.
29. Shan, C., Xie, X., Muruato, A. E., Rossi, S. L., Roundy, C. M., Azar, S. R., Yang, Y., Tesh, R. B., Bourne, N., Barrett, A. D., et al. (2016b). An Infectious cDNA Clone of Zika Virus to Study Viral Virulence, Mosquito Transmission, and Antiviral Inhibitors. *Cell Host Microbe* 19, 891-900.
30. Sirohi, D., Chen, Z., Sun, L., Klose, T., Pierson, T. C., Rossmann, M. G., and Kuhn, R. J. (2016). The 3.8 A resolution cryo-EM structure of Zika virus. *Science* 352, 467-470.
31. Tsetsarkin, K. A., Kenney, H., Chen, R., Liu, G., Manukyan, H., Whitehead, S. S., Laassri, M., Chumakov, K., and Pletnev, A. G. (2016). A Full-Length Infectious cDNA Clone of Zika Virus from the 2015 Epidemic in Brazil as a Genetic Platform for Studies of Virus-Host Interactions and Vaccine Development. *MBio* 7.
32. Weger-Lucarelli, J Duggal, N. K., Bullard-Feibelman, K., Veselinovic, M., Romo, H., Nguyen, C., Ruckert, C., Brault, A. C., Bowen, R. A., Stenglein, M., et al. (2017). Development and Characterization of Recombinant Virus Generated from a New World Zika Virus Infectious Clone. *J Virol* 91.
33. Xie, X., Gayen, S., Kang, C., Yuan, Z., and Shi, P. Y. (2013). Membrane topology and function of dengue virus NS2A protein. *J Virol* 87, 4609-4622.
34. Xie, X., Zou, J., Shan, C., Yang, Y., Kum, D. B., Dallmeier, K., Neyts, J., and Shi, P. Y. (2016). Zika Virus Replicons for Drug Discovery. *EBioMedicine* 12, 156-160.
35. Youn, S., Li, T., McCune, B. T., Edeling, M. A., Fremont, D. H., Cristea, I. M., and Diamond, M. S. (2012). Evidence for a genetic and physical interaction between nonstructural proteins NS1 and NS4B that modulates replication of West Nile virus. *J Virol* 86, 7360-7371.
36. Zou, J Xie, X., Lee le, T., Chandrasekaran, R., Reynaud, A., Yap, L., Wang, Q. Y., Dong, H., Kang, C., Yuan, Z., et al. (2014). Dimerization of flavivirus NS4B protein. *J Virol* 88, 3379-3391.

In the preceding procedures, various steps have been described. It will, however, be evident that various modifications and changes may be made thereto, and additional procedures may be implemented, without departing from the broader scope of the exemplary procedures as set forth in the claims that follow.

The invention claimed is:

1. A variant Zika virus (ZIKV) cDNA clone, RNA transcript of the cDNA clone, or variant ZIKV strain which has been mutated to introduce at least one substitution mutation in at least one of the encoded ZIKV proteins, wherein said at least one substitution mutation comprises one or more of the following: NS1 K265E, prM H83R and NS3 S356F.

2. The cDNA clone, RNA transcript, or strain of claim 1, wherein the encoded ZIKV NS1 protein comprises a K265E substitution mutation.

3. The cDNA clone, RNA transcript, or strain of claim 1, wherein the encoded ZIKV proteins in the variant comprise one of the following combinations of substitution mutations: (a) NS1 K265E, prM H83R and NS3 S356F; (b) NS1 K265E and prM H83R; or (c) NS1 K265E and NS3 S356F.

4. The cDNA clone, RNA transcript, or strain of claim 1 wherein the encoded ZIKV proteins in the variant further comprises one or more of the following substitution mutations: prM H83R, NS3 S356F, E R283W, E H219L, E L441L, E K443N, E T315I, E H401Y, E A501T, NS1 R103K, and NS1 W98L.

5. The cDNA clone, RNA transcript, or strain of claim 1, which is a variant of one of the following: a cDNA clone of a North or South American ZIKV strain, an RNA transcript of the cDNA clone of a North or South American ZIKV strain, or a North or South American ZIKV strain.

6. The cDNA clone, RNA transcript, or strain of claim 1, which is a variant of one of the following:
(i) a cDNA clone of a strain selected from the group consisting of MR766-NIID, P6-740, ArD7117, IbH_30656, ArB1362, ARB13565, ARB7701, ARB15076, ArD_41519, ArD128000, ArD158084, ArD157995, FSM, FSS13025, PHL/2012/CPC-0740-Asian, H/PF/2013, PLCal_ZV, Haiti/1225/2014, SV0127_14_Asian, Natal_RGN_Asian, Brazil_ZKV2015_Asian, ZikaSPH2015, BeH815744, BeH819015, BeH819966, BeH823339, BeH828305, SSABR1-Asian, FLR, 103344, 8375, PRVABC59, Z1106033, MRS_OPY_Martinique, VE_Ganxian_Asian, GD01_Asian, GDZ16001, ZJO3, Rio-U1 and Rio-S1;
(ii) an RNA transcript of the cDNA clone of a strain selected from the group consisting of MR766-NIID, P6-740, ArD7117, IbH_30656, ArB1362, ARB13565, ARB7701, ARB15076, ArD_41519, ArD128000, ArD158084, ArD157995, FSM, FSS13025, PHL/2012/CPC-0740-Asian, H/PF/2013, PLCal_ZV, Haiti/1225/2014, SV0127_14_Asian, Natal_RGN_Asian, Brazil_ZKV2015_Asian, ZikaSPH2015, BeH815744, BeH819015, BeH819966, BeH823339, BeH828305, SSABR1-Asian, FLR, 103344, 8375, PRVABC59, Z1106033, MRS_OPY_Martinique, VE_Ganxian_Asian, GD01_Asian, GDZ16001, ZJO3, Rio-U1 and Rio-S1; or (iii) a strain selected from the group consisting of MR766-NIID, P6-740, ArD7117, IbH_30656, ArB1362, ARB13565, ARB7701, ARB15076, ArD_41519, ArD128000, ArD158084, ArD157995, FSM, FSS13025, PHL/2012/CPC-0740-Asian, H/PF/2013, PLCal_ZV, Haiti/1225/2014, SV0127_14_Asian, Natal_RGN_Asian, Brazil_ZKV2015_Asian, ZikaSPH2015, BeH815744, BeH819015, BeH819966, BeH823339, BeH828305, SSABR1-Asian, FLR, 103344, 8375, PRVABC59, Z1106033, MRS_OPY_Martinique, VE_Ganxian_Asian, GD01_Asian, GDZ16001, ZJO3, Rio-U1 and Rio-S1.

7. The cDNA clone, RNA transcript, or strain of claim 1, wherein the strain is a variant of PRVABC59 or FSS13025.

8. The cDNA clone, RNA transcript, or strain of claim 1, which (i) provides increased yield of ZIKV production in cells as compared to the corresponding wildtype ZIKV cDNA clone, RNA transcript, or strain lacking these substitution mutations; and/or (ii) provides enhanced ZIKV assembly as compared to a corresponding wildtype ZIKV cDNA clone, RNA transcript, or strain lacking these substitution mutations.

9. The cDNA clone, RNA transcript, or strain of claim 8, wherein the cells used to produce ZIKVs are selected from one of the following types of cells: (i) eukaryotic cells; (ii) mammalian cells; (iii) mouse or human cells; (iv) Vero cells, Huh7 cells, LLC-MK-2 cells, Hep-2 cells, LF 1043 (HEL) cells, MRC-5 cells, WI-38 cells, tMK cells, 293 T cells, QT 6 cells, QT 35 cells, or chicken embryo fibroblasts (CEF); and (v) Vero cells or Huh7 cells.

10. The cDNA clone, RNA transcript, or strain of claim 1 which is an infectious cDNA clone, RNA transcript, or strain.

11. The cDNA clone, RNA transcript, or strain of claim 1 which is further modified to include at least one additional mutation which results in a substitution, addition or deletion mutation in at least one Zika protein, preferably NS1, NS3 or prm, wherein said additional modification does not adversely impact the efficacy of the resultant cDNA clone, RNA transcript, or strain for use in vaccines.

12. A method for producing ZIKV for vaccine manufacture, comprising producing additional copies of the cDNA clone, RNA transcript, or strain of claim 1 in a suitable system thereby obtaining additional ZIKV variants suitable for use in the manufacture of ZIKV vaccines.

13. The method of claim 12, wherein the suitable system comprises producing the ZIKV in cells.

14. The method of claim 13, wherein the cells are selected from one of the following groups: (i) eukaryotic cells; (ii) mammalian cells; (iii) mouse or human cells; (iv) Vero cells, Huh7 cells, LLC-MK-2 cells, Hep-2 cells, LF 1043 (HEL) cells, MRC-5 cells, WI-38 cells, tMK cells, 293 T cells, QT 6 cells, QT 35 cells, or chicken embryo fibroblasts (CEF); and (v) Vero cells or Huh7 cells.

15. The method of claim 12, wherein the produced ZIKV variants are attenuated or inactivated.

16. A variant ZIKV cDNA clone, RNA transcript of the cDNA clone, or variant ZIKV strain comprising a substitution mutation corresponding to A3282G in the ZIKV genome, wherein the A3282G substitution results in a K265E substitution in the NS1 protein upon expression of the cDNA clone, RNA transcript or strain.

17. An immunogenic composition comprising at least one variant ZIKV strain according to claim 1, and at least one pharmaceutically acceptable carrier or excipient, wherein the strain is attenuated or inactivated.

18. The immunogenic composition of claim 17, which is suitable for parenteral or enteral administration.

19. A method of eliciting an immune response in a subject in need thereof by administering a composition comprising a prophylactically or therapeutically effective amount of a variant ZIKV strain according to claim 1, or an immunogenic composition containing, wherein the ZIKV strain is attenuated or inactivated.

20. The method of claim 19, which (i) induces a CD8$^+$ T cell response, an antibody response, and/or a cellular immune response against ZIKV; (ii) produces a neutralizing antibody titer equivalent to that of wildtype ZIKV infection; (iii) is used to prevent congenital ZIKV syndrome and/or microcephaly; (iv) prevents viremia in said subject after subsequent challenge with a wildtype ZIKV strain and/or the subject is a human and/or a pregnant female.

* * * * *